United States Patent
Vonwiller et al.

(10) Patent No.: US 7,470,315 B2
(45) Date of Patent: Dec. 30, 2008

(54) RED-SHIFTED WATER DISPERSIBLE NAPTHALOCYANINE DYES

(75) Inventors: Simone Charlotte Vonwiller, Balmain (AU); Damon Donald Ridley, Balmain (AU); Sutharsiny Indusegaram, Balmain (AU); Scott Matthew Starling, Balmain (AU); Graciel Gonzaga, Balmain (AU); Kia Silverbrook, Balmain (AU)

(73) Assignee: Silverbrook Research Pty Ltd, Balmain, New South Wales (AU)

( * ) Notice: Subject to any disclaimer, the term of this patent is extended or adjusted under 35 U.S.C. 154(b) by 511 days.

(21) Appl. No.: 11/172,815

(22) Filed: Jul. 5, 2005

(65) Prior Publication Data

US 2007/0008393 A1    Jan. 11, 2007

(51) Int. Cl.
C09D 11/02 (2006.01)
C09B 47/04 (2006.01)
C07D 487/22 (2006.01)

(52) U.S. Cl. ............... 106/31.49; 106/31.47; 540/122; 540/123; 540/124

(58) Field of Classification Search ............... 106/31.49, 106/31.47; 540/122, 123, 124
See application file for complete search history.

(56) References Cited

U.S. PATENT DOCUMENTS

| | | | | |
|---|---|---|---|---|
| 2,277,629 A * | 3/1942 | Flower et al. | | 540/124 |
| 4,854,676 A * | 8/1989 | Kalyanaraman et al. | | 359/243 |
| 4,864,618 A | 9/1989 | Wright et al. | | |
| 5,032,495 A * | 7/1991 | Albert et al. | | 540/123 |
| 5,051,736 A | 9/1991 | Bennet et al. | | |
| 5,282,894 A * | 2/1994 | Albert et al. | | 106/31.49 |
| 5,322,760 A * | 6/1994 | Itoh et al. | | 540/123 |
| 5,397,819 A * | 3/1995 | Krutak et al. | | 524/88 |
| 5,477,012 A | 12/1995 | Sekendur | | |
| 5,614,008 A * | 3/1997 | Escano et al. | | 106/31.49 |
| 5,652,412 A | 7/1997 | Lazzouni et al. | | |
| 5,661,506 A | 8/1997 | Lazzouni et al. | | |
| 5,692,073 A | 11/1997 | Cass | | |
| 5,788,914 A * | 8/1998 | Oi et al. | | 540/125 |
| 5,804,102 A | 9/1998 | Oi et al. | | |
| 5,852,434 A | 12/1998 | Sekendur | | |
| 5,953,857 A | 9/1999 | Aiga et al. | | |
| 6,076,734 A | 6/2000 | Dougherty et al. | | |
| 6,533,852 B2 * | 3/2003 | Hirose | | 106/31.49 |
| 6,726,755 B2 * | 4/2004 | Titterington et al. | | 106/31.49 |
| 6,964,374 B1 | 11/2005 | Djuknic et al. | | |

FOREIGN PATENT DOCUMENTS

| | | |
|---|---|---|
| GB | 2306669 | 5/1997 |
| JP | 01287175 A | 5/1988 |
| JP | 01108264 A | 4/1989 |
| JP | 05086300 A | 4/1993 |
| JP | 07082517 A | 3/1995 |
| WO | WO-99/18487 A2 | 4/1999 |
| WO | WO-99/50787 A1 | 10/1999 |

OTHER PUBLICATIONS

Dymetman, M., and Copperman, M., "Intelligent Paper in Electronic Publishing, Artist Imaging, and Digital Typography, Proceedings of EP '98", Mar./Apr. 1998, Springer Verlag LNCS 1375, pp. 392-406.

Kitahara et al "Synthesis of Octasubstituted Metal Napthalocyanines", Phosphorus, Sulfur, and Silicon, vol. 67, pp. 373-376 (1992) see compound No. 5, table I, p. 374 inter alia, no month available.

Yeung et al "Synthetic studies of substituted 2,3-naphthalocyanine", Tetrahedron, vol. 53, No. 27, pp. 9087-9096 (1997) see compound 24, p. 9089 and 9095 inter alia, no month available.

* cited by examiner

*Primary Examiner*—Helene Klemanski

(57) ABSTRACT

A naphthalocyanine dye of formula (I) is provided:

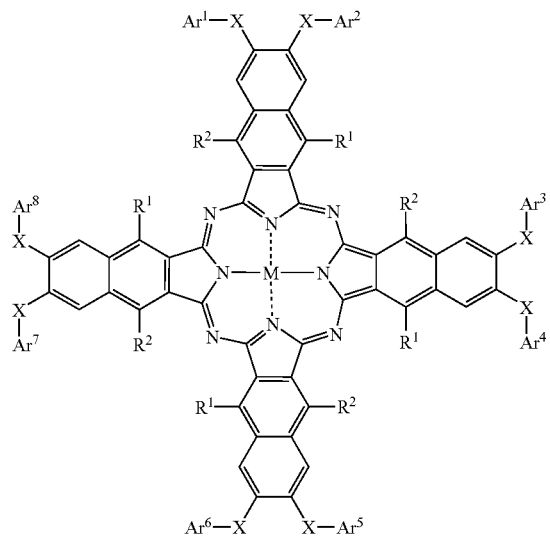

(I)

wherein

M is a metal group or is absent;

$R^1$ and $R^2$ are independently selected from hydrogen or $C_{1-12}$ alkoxy;

X is selected from O, S or —NH—;

$Ar^1$, $Ar^2$, $Ar^3$, $Ar^4$, $Ar^5$, $Ar^6$, $Ar^7$ and $Ar^8$ are selected from phenyl, naphthyl, pyridyl, furanyl, pyrollyl, thiophenyl, each of $Ar^1$, $Ar^2$, $Ar^3$, $Ar^4$, $Ar^5$, $Ar^6$, $Ar^7$ and $Ar^8$ being optionally substituted with 1, 2, 3, 4 or 5 groups, the or each group being independently selected from $C_{1-12}$ alkyl, $C_{1-12}$ alkoxy, $C_{1-12}$ arylalkyl, $C_{1-12}$ arylalkoxy, —$(OCH_2CH_2)_d$ $OR^d$, cyano, halogen, amino, hydroxyl, thiol, —$SR^v$, —$NR^uR^v$, nitro, phenyl, phenoxy, —$CO_2R^v$, —$C(O)R^v$, —$OCOR^v$, —$SO_2R^v$, —$OSO_2R^v$, —$NHC(O)R^v$, —$CONR^uR^v$, —$CONR^uR^v$, sulfonic acid, sulfonic acid salt and sulfonamide;

d is an integer from 2 to 5000;

$R^d$ is H, $C_{1-8}$ alkyl or $C(O)C_{1-8}$ alkyl; and $R^u$ and $R^v$ are independently selected from hydrogen, $C_{1-12}$ alkyl, phenyl or phenyl-$C_{1-8}$ alkyl.

9 Claims, 26 Drawing Sheets

RED-SHIFTED WATER DISPERSIBLE NAPTHALOCYANINE DYES

FIELD OF THE INVENTION

The present application relates to red-shifted near-IR dyes, which are synthetically accessible in high yield and which are dispersible in an aqueous ink base. It has been developed primarily to provide dyes with greater functionality, suitable for improving water-solubility or inhibiting intermolecular interactions.

CO-PENDING APPLICATIONS

Various methods, systems and apparatus relating to the present invention are disclosed in the following co-pending applications filed by the applicant or assignee of the present invention simultaneously with the present application:

| | | | | | |
|---|---|---|---|---|---|
| 7278727 | 10/913373 | 10/913374 | 10/913372 | 7138391 | 7153956 |
| 10/913380 | 10/913379 | 10/913376 | 7122076 | 7148345 | 11/172816 |
| 11/172814 | | | | | |

The disclosures of these co-pending applications are incorporated herein by cross-reference.

Where applications are temporarily identified by its docket number, these will be replaced by the corresponding USSN when available.

BACKGROUND OF THE INVENTION

IR absorbing dyes have numerous applications, such as optical recording systems, thermal writing displays, laser filters, infrared photography, medical applications and printing. Typically, it is desirable for the dyes used in these applications to have strong absorption in the near-IR at the emission wavelengths of semiconductor lasers (e.g. between about 700 and 2000 nm, preferably between about 700 and 1000 nm). In optical recording technology, for example, gallium aluminium arsenide (GaAlAs) and indium phosphide (InP) diode lasers are widely used as light sources.

Another important application of IR dyes is in inks, such as printing inks. The storage and retrieval of digital information in printed form is particularly important. A familiar example of this technology is the use of printed, scannable bar codes. Bar codes are typically printed onto tags or labels associated with a particular product and contain information about the product, such as its identity, price etc. Bar codes are usually printed in lines of visible black ink, and detected using visible light from a scanner. The scanner typically comprises an LED or laser (e.g. a HeNe laser, which emits light at 633 nm) light source and a photocell for detecting reflected light. Black dyes suitable for use in barcode inks are described in, for example, WO03/074613.

However, in other applications of this technology (e.g. security tagging) it is desirable to have a barcode, or other intelligible marking, printed with an ink that is invisible to the unaided eye, but which can be detected under UV or IR light.

An especially important application of detectable invisible ink is in automatic identification systems, and especially "netpage" and "Hyperlabel™" systems. Netpage systems are described in the following patent applications, all of which are incorporated herein by reference.

CROSS-REFERENCES

Various methods, systems and apparatus relating to the present invention are disclosed in the following co-pending applications filed by the applicant or assignee of the present application:

| | | | | | |
|---|---|---|---|---|---|
| 10/815621 | 7243835 | 10/815630 | 10/815637 | 7251050 | 10/815642 |
| 7097094 | 7137549 | 10/815618 | 7156292 | 10/815635 | 10/815647 |
| 10/815634 | 7137566 | 7131596 | 7128265 | 7207485 | 7197374 |
| 7175089 | 10/815617 | 10/815620 | 7178719 | 10/815613 | 7207483 |
| 7296737 | 7270266 | 10/815614 | 10/815636 | 7128270 | 10/815609 |
| 7150398 | 7159777 | 10/815610 | 7188769 | 7097106 | 7070110 |
| 7243849 | 7204941 | 7282164 | 10/815628 | 7156289 | 7178718 |
| 7225979 | 09/575197 | 7079712 | 6825945 | 09/575165 | 6813039 |
| 7190474 | 6987506 | 6824044 | 6980318 | 6816274 | 7102772 |
| 09/575186 | 6681045 | 6678499 | 6679420 | 6963845 | 6976220 |
| 6728000 | 7110126 | 7173722 | 6976035 | 6813558 | 6766942 |
| 6965454 | 6995859 | 7088459 | 6720985 | 7286113 | 6922779 |
| 6978019 | 6847883 | 7131058 | 7295839 | 09/607843 | 09/693690 |
| 6959298 | 6973450 | 7150404 | 6965882 | 7233924 | 09/575181 |
| 09/722174 | 7175079 | 7162259 | 6718061 | 10/291523 | 10/291471 |
| 7012710 | 6825956 | 10/291481 | 7222098 | 10/291825 | 7263508 |
| 7031010 | 6972864 | 6862105 | 7009738 | 6989911 | 6982807 |
| 10/291576 | 6829387 | 6714678 | 6644545 | 6609653 | 6651879 |
| 10/291555 | 7293240 | 10/291592 | 10/291542 | 7044363 | 7004390 |
| 6867880 | 7034953 | 6987581 | 7216224 | 10/291821 | 7162269 |
| 7162222 | 7290210 | 7293233 | 7293234 | 6850931 | 6865570 |
| 6847961 | 10/685523 | 10/685583 | 7162442 | 10/685584 | 7159784 |
| 10/804034 | 10/793933 | 6889896 | 10/831232 | 7068382 | 7007851 |
| 6957921 | 6457883 | 10/743671 | 7094910 | 7091344 | 7122685 |
| 7038066 | 7099019 | 7062651 | 6789194 | 6789191 | 6644642 |
| 6502614 | 6622999 | 6669385 | 6827116 | 6549935 | 6987573 |
| 6727996 | 6591884 | 6439706 | 6760119 | 7295332 | 7064851 |
| 6826547 | 6290349 | 6428155 | 6785016 | 6831682 | 6741871 |
| 6927871 | 6980306 | 6965439 | 6840606 | 7036918 | 6977746 |
| 6970264 | 7068389 | 7093991 | 7190491 | 6982798 | 6870966 |
| 6822639 | 6474888 | 6627870 | 6724374 | 6788982 | 7263270 |
| 6788293 | 6946672 | 6737591 | 7091960 | 09/693514 | 6792165 |
| 7105753 | 6795593 | 6980704 | 6768821 | 7132612 | 7041916 |
| 6797895 | 7015901 | 7289882 | 7148644 | 10/778056 | 10/778058 |
| 10/778060 | 10/778059 | 10/778063 | 10/778062 | 10/778061 | 10/778057 |
| 7096199 | 7055739 | 7233320 | 6830196 | 6832717 | 7182247 |
| 7082562 | 6843420 | 10/291718 | 6789731 | 7057608 | 6766944 |
| 6766945 | 7289103 | 10/291559 | 7299969 | 10/409864 | 7108192 |
| 7111791 | 6983878 | 10/786631 | 7134598 | 10/683151 | 10/683040 |
| 10/778090 | 6957776 | 09/575172 | 7170499 | 7106888 | 7123239 |
| 6982701 | 6982703 | 7227527 | 6786397 | 6947027 | 6975299 |
| 7139431 | 7048178 | 7118025 | 6839053 | 7015900 | 7010147 |
| 7133557 | 6914593 | 10/291546 | 6454482 | 6808330 | 6527365 |
| 6474773 | 6550997 | 7093923 | 6957923 | 7131724 | |

The disclosures of all of these co-pending patents/patent applications are incorporated herein by reference.

In general, the netpage system relies on the production of, and human interaction with, netpages. These are pages of text, graphics and images printed on ordinary paper, but which work like interactive web pages. Information is encoded on each page using ink which is substantially invisible to the unaided human eye. The ink, however, and thereby the coded data, can be sensed by an optically imaging pen and transmitted to the netpage system.

Active buttons and hyperlinks on each page may be clicked with the pen to request information from the network or to signal preferences to a network server. In some forms, text written by hand on a netpage may be automatically recognized and converted to computer text in the netpage system, allowing forms to be filled in. In other forms, signatures recorded on a netpage may be automatically verified, allowing e-commerce transactions to be securely authorized.

Netpages are the foundation on which a netpage network is built. They may provide a paper-based user interface to published information and interactive services.

A netpage consists of a printed page (or other surface region) invisibly tagged with references to an online description of the page. The online page description is maintained persistently by a netpage page server. The page description describes the visible layout and content of the page, including text, graphics and images. It also describes the input elements on the page, including buttons, hyperlinks, and input fields. A netpage allows markings made with a netpage pen on its surface to be simultaneously captured and processed by the netpage system.

Multiple netpages can share the same page description. However, to allow input through otherwise identical pages to be distinguished, each netpage is assigned a unique page identifier. This page ID has sufficient precision to distinguish between a very large number of netpages.

Each reference to the page description is encoded in a printed tag. The tag identifies the unique page on which it appears, and thereby indirectly identifies the page description. The tag also identifies its own position on the page.

Tags are printed in infrared-absorptive ink on any substrate which is infrared-reflective, such as ordinary paper. Near-infrared wavelengths are invisible to the human eye but are easily sensed by a solid-state image sensor with an appropriate filter.

A tag is sensed by an area image sensor in the netpage pen, and the tag data is transmitted to the netpage system via the nearest netpage printer. The pen is wireless and communicates with the netpage printer via a short-range radio link. Tags are sufficiently small and densely arranged that the pen can reliably image at least one tag even on a single click on the page. It is important that the pen recognize the page ID and position on every interaction with the page, since the interaction is stateless. Tags are error-correctably encoded to make them partially tolerant to surface damage.

The netpage page server maintains a unique page instance for each printed netpage, allowing it to maintain a distinct set of user-supplied values for input fields in the page description for each printed netpage.

Hyperlabel™ is a trade mark of Silverbrook Research Pty Ltd, Australia. In general, Hyperlabel™ systems use an invisible (e.g. infrared) tagging scheme to uniquely identify a product item. This has the significant advantage that it allows the entire surface of a product to be tagged, or a significant portion thereof, without impinging on the graphic design of the product's packaging or labeling. If the entire surface of a product is tagged ("omnitagged"), then the orientation of the product does not affect its ability to be scanned i.e. a significant part of the line-of-sight disadvantage of visible barcodes is eliminated. Furthermore, if the tags are compact and massively replicated ("omnitags"), then label damage no longer prevents scanning.

Thus, hyperlabelling consists of covering a large portion of the surface of a product with optically-readable invisible tags. When the tags utilize reflection or absorption in the infrared spectrum, they are referred to as infrared identification (IRID) tags. Each Hyperlabel™ tag uniquely identifies the product on which it appears. The tag may directly encode the product code of the item, or it may encode a surrogate ID which in turn identifies the product code via a database lookup. Each tag also optionally identifies its own position on the surface of the product item, to provide the downstream consumer benefits of netpage interactivity.

Hyperlabels™ are applied during product manufacture and/or packaging using digital printers, preferably inkjet printers. These may be add-on infrared printers, which print the tags after the text and graphics have been printed by other means, or integrated colour and infrared printers which print the tags, text and graphics simultaneously.

Hyperlabels™ can be detected using similar technology to barcodes, except using a light source having an appropriate near-IR frequency. The light source may be a laser (e.g. a GaAlAs laser, which emits light at 830 nm) or it may be an LED.

From the foregoing, it will be readily apparent that invisible IR detectable inks are an important component of netpage and Hyperlabel™ systems. In order for an IR absorbing ink to function satisfactorily in these systems, it should ideally meet a number of criteria:

(i) compatibility with inkjet printers;
(ii) compatibility of the IR dye with aqueous solvents used in inkjet inks;
(iii) intense absorption in the near infra-red region (e.g. 700 to 1000 nm);
(iv) zero or low intensity visible absorption;
(v) lightfastness;
(vi) thermal stability;
(vii) zero or low toxicity;
(viii) low-cost manufacture;
(ix) adheres well to paper and other media; and
(x) no strikethrough and minimal bleeding of the ink on printing.

Hence, it would be desirable to develop IR dyes and ink compositions fulfilling at least some and preferably all of the above criteria. Such inks are desirable to complement netpage and Hyperlabel™ systems.

Some IR dyes are commercially available from various sources, such as Epolin Products, Avecia Inks and H.W. Sands Corp.

U.S. Pat. No. 5,282,894 describes a solvent-based printing ink comprising a metal-free phthalocyanine, a complexed phthalocyanine, a metal-free naphthalocyanine, a complexed naphthalocyanine, a nickel dithiolene, an aminium compound, a methine compound or an azulenesquaric acid.

However, none of the prior art dyes can be formulated into ink compositions suitable for use in netpage or Hyperlabel™ systems. In particular, commercially available and/or prior art inks suffer from one or more of the following problems: absorption at wavelengths unsuitable for detection by near-IR sensors; poor solubility or dispersibility in aqueous solvent systems; or unacceptably high absorption in the visible part of the spectrum.

In a typical netpage, there may be a large number of hyperlinks on one page and correspondingly relatively large areas of the page printed with IR ink. In the Hyperlabel™ system, the majority of a product's packaging may be printed with the invisible ink. Thus, it is especially desirable that the ink used is invisible to the unaided eye and contains minimal residual colour.

Moreover, inkjet printing is the preferred means for generating netpages and Hyperlabels™. Inkjet printing is preferred primarily for its high-speed and low cost. Inkjet inks are typically water-based for reasons of low cost, low toxicity and low flammability. In thermal bubble-jet printers, the ink needs to be rapidly vaporized during the printing process. This rapid vaporization of the ink during the printing process necessitates a water-based ink composition. Accordingly, it is desirable that the IR dyes used in netpage and Hyperlabel™ inks are suitable for formulating into aqueous ink compositions and are compatible with inkjet printers.

A further essential requirement of IR dyes used in netpage systems is that they must absorb IR radiation at a frequency complementary to the frequency of the IR sensor in the netpage pen. Preferably, the ink should contain a dye, which absorbs strongly at the frequency of the IR sensor. Accordingly, the dyes used in netpage systems should absorb strongly in the near-IR region—that is, 700 to 1000 nm, preferably 750 to 900 nm, more preferably 780 to 850 nm.

With the anticipated widespread use of netpage and Hyperlabel™, it would be especially desirable to develop a low-cost near-IR dye which can be prepared in high yields on an industrial scale, and which is acceptably light stable.

SUMMARY OF THE INVENTION

In a first aspect, there is provided a naphthalocyanine dye of formula (I):

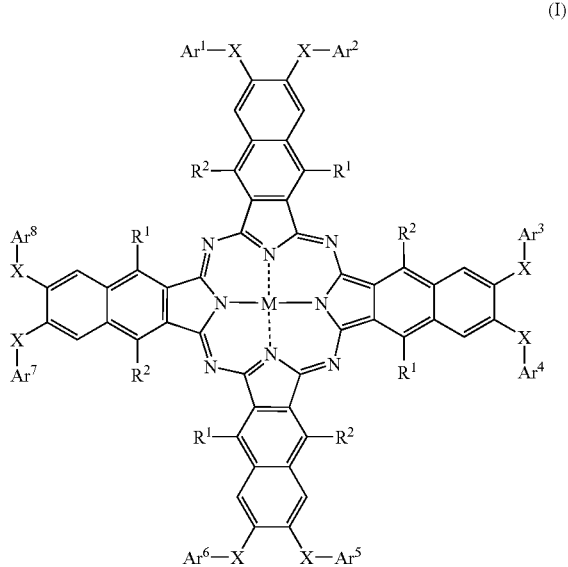

(I)

wherein
M is a metal group or is absent;
$R^1$ and $R^2$ are independently selected from hydrogen or $C_{1-12}$ alkoxy;
X is selected from O, S or —NH—;
$Ar^1$, $Ar^2$, $Ar^3$, $Ar^4$, $Ar^5$, $Ar^6$, $Ar^7$ and $Ar^8$ are selected from phenyl, naphthyl, pyridyl, furanyl, pyrollyl, thiophenyl, each of $Ar^1$, $Ar^2$, $Ar^3$, $Ar^4$, $Ar^5$, $Ar^6$, $Ar^7$ and $Ar^8$ being optionally substituted with 1, 2, 3, 4 or 5 groups, each group being independently selected from $C_{1-12}$ alkyl, $C_{1-12}$ alkoxy, $C_{1-12}$ arylalkyl, $C_{1-12}$ arylalkoxy, —$(OCH_2CH_2)_d$ $OR^d$, cyano, halogen, amino, hydroxyl, thiol, —$SR^v$, —$NR^uR^v$, nitro, phenyl, phenoxy, —$CO_2R^v$, —$C(O)R^v$, —$OCOR^v$, —$SO_2R^v$, —$OSO_2R^v$, —$NHC(O)R^v$, —$CONR^uR^v$, —$CONR^uR^v$, sulfonic acid, sulfonic acid salt and sulfonamide;
d is an integer from 2 to 5000;
$R^d$ is H, $C_{1-8}$ alkyl or $C(O)C_{1-8}$ alkyl; and
$R^u$ and $R^v$ are independently selected from hydrogen, $C_{1-12}$ alkyl, phenyl or phenyl-$C_{1-8}$ alkyl;

Optionally, at least one of $Ar^1$, $Ar^2$, $Ar^3$, $Ar^4$, $Ar^5$, $Ar^6$, $Ar^7$ and $Ar^8$ is substituted with a hydrophilic group, such as a sulfonic acid, a sulfonic acid salt or a sulfonamide group.

In a second aspect, the present invention provides an inkjet ink comprising a dye as described above.

In a third aspect, the present invention provides an inkjet printer comprising a printhead in fluid communication with at least one ink reservoir, wherein said at least one ink reservoir comprises an inkjet ink as described above.

In a fourth aspect, the present invention provides an ink cartridge for an inkjet printer, wherein said ink cartridge comprises an inkjet ink as described above.

In a fifth aspect, the present invention provides a substrate having a dye as described above disposed thereon.

In a sixth aspect, there is provided a method of enabling entry of data into a computer system via a printed form, the form containing human-readable information and machine-readable coded data, the coded data being indicative of an identity of the form and of a plurality of reference points of the form, the method including the steps of:

receiving, in the computer system and from a sensing device, indicating data regarding the identity of the form and a position of the sensing device relative to the form, the sensing device, when placed in an operative position relative to the form, generating the indicating data using at least some of the coded data;

identifying, in the computer system and from the indicating data, at least one field of the form; and interpreting, in the computer system, at least some of the indicating data as it relates to the at least one field, wherein said coded data comprises an IR-absorbing dye as described above.

Optionally, the at least one field is associated with at least one zone of the form, the identifying step including identifying that the position of the sensing device is within the at least one zone. Optionally, the indicating data includes movement data regarding movement of the sensing device relative to the form, the sensing device generating the movement data using at least some of the coded data, the identifying step including identifying that the movement of the sensing device is at least partially within the at least one zone.

In a seventh aspect, there is provided a method of enabling entry of data into a computer system via a printed form, the form containing human-readable information and machine-readable coded data, the coded data being indicative of at least one field of the form, the method including the steps of:

receiving, in the computer system and from a sensing device, indicating data regarding the at least one field and including movement data regarding movement of the sensing device relative to the form, the sensing device, when moved relative to the form, generating the data regarding said at least one field using at least some of the coded data and generating the data regarding its own movement relative to the form; and interpreting, in the computer system, at least some of said indicating data as it relates to said at least one field, wherein said coded data comprises an IR-absorbing dye as described above.

Optionally, the sensing device generates the movement data using at least some of the coded data. Optionally, the at least one field is a text field and the interpreting step includes converting at least some of the movement data to text. Optionally, the at least one field is a drawing field. Optionally, the at least one field is a checkbox field and the interpreting step includes interpreting at least some of the movement data as a check mark. Optionally, the at least one field is a signature field and the interpreting step includes verifying that at least some of the movement data represents a signature of a user associated with the sensing device. Optionally, the at least one field is an action field and the interpreting step includes sending a message to an application associated with the action field. Optionally, the action field is a form submission action field and the message includes form data derived from at least one other field of the form.

In an eighth aspect, there is provided a method of enabling entry of data into a computer system via a product item, the product item having a printed surface containing human-readable information and machine-readable coded data, the coded data being indicative of an identity of the product item, the method including the steps of:

(a) receiving, in the computer system and from a sensing device, indicating data regarding the identity of the product item, the sensing device, when placed in an operative position relative to the product item, generating the indicating data using at least some of the coded data; and
(b) recording, in the computer system and using the indicating data, information relating to the product item, wherein said coded data comprises an IR-absorbing dye as described above.

In a ninth aspect, there is provided a method of enabling retrieval of data from a computer system via a product item, the product item having a printed surface containing human-readable information and machine-readable coded data, the coded data being indicative of an identity of the product item, the method including the steps of:
(a) receiving, in the computer system and from a sensing device, indicating data regarding the identity of the product item, the sensing device, when placed in an operative position relative to the product item, generating the indicating data using at least some of the coded data;
(b) retrieving, in the computer system and using the indicating data, information relating to the product item; and
(c) outputting, from the computer system and to an output device, the information relating to the product item, the output device selected from the group comprising a display device and a printing device, wherein said coded data comprises an IR-absorbing dye as described above.

Optionally, the coded data is formed from a plurality of coded data portions, each coded data portion being indicative of the identity of the product item. Optionally, the coded data is indicative of at least one of a UPC and an EPC associated with the product item. Optionally, the form is disposed on a surface of a product item and in which the coded data is indicative of an identity of the product item. Optionally, the coded data is formed from a plurality of coded data portions, each coded data portion being indicative of the identity of the product item. Optionally, the coded data is indicative of at least one of a UPC and an EPC associated with the product item.

BRIEF DESCRIPTION OF DRAWINGS

FIG. 5b is a plan view showing a macrodot layout for the tag shown in FIG. 5a;

DETAILED DESCRIPTION

IR-Absorbing Dye

Figure 1:
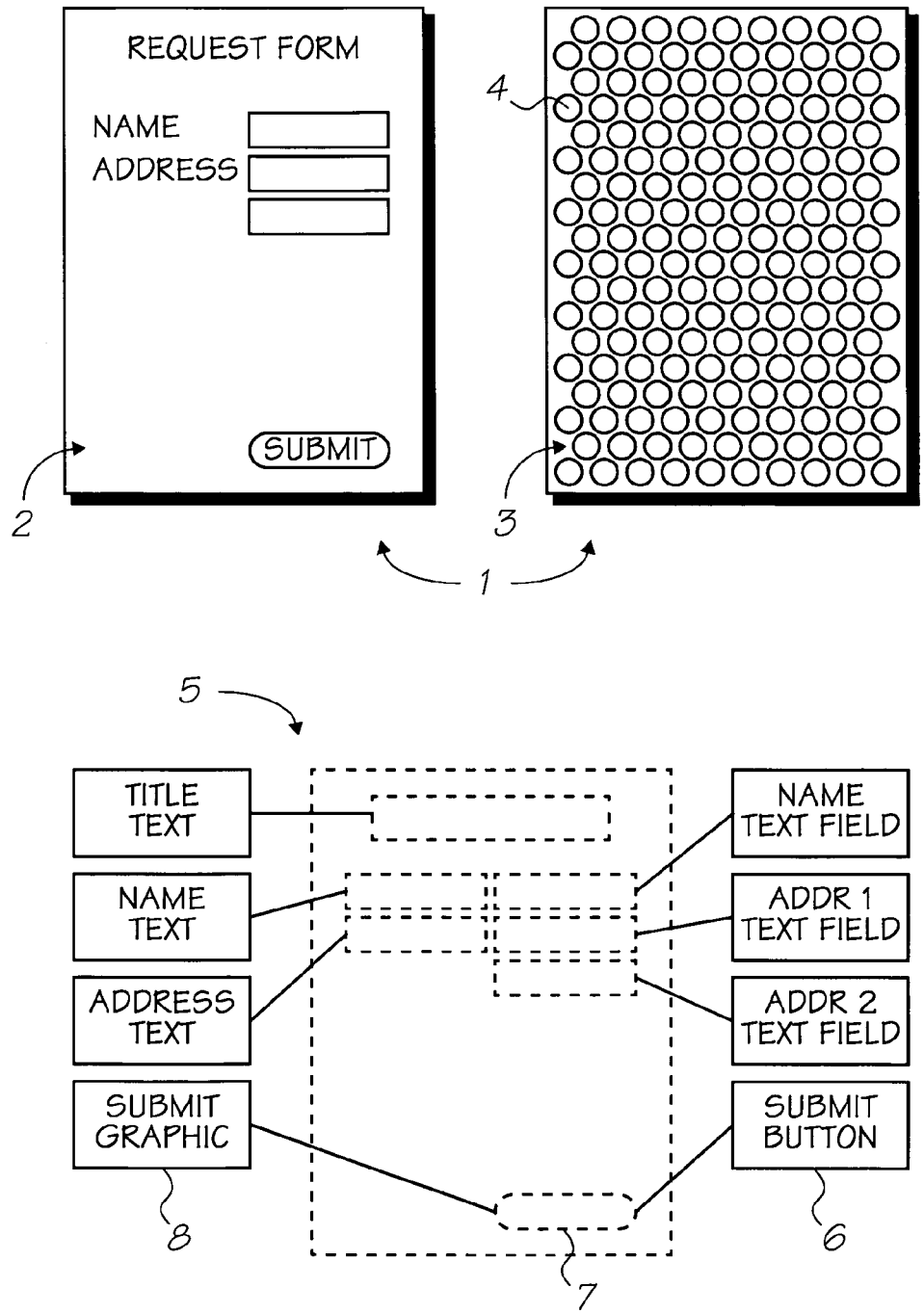
FIG. 1 is a schematic of a the relationship between a sample printed netpage and its online page description.

As used herein, the term "IR-absorbing dye" means a dye substance, which absorbs infrared radiation and which is therefore suitable for detection by an infrared sensor. Preferably, the IR-absorbing dye absorbs in the near infrared region, and preferably has a $\lambda_{max}$ in the range of 700 to 1000 nm, more preferably 750 to 900 nm, more preferably 780 to 850 nm. Dyes having a $\lambda_{max}$ in this range are particularly suitable for detection by semiconductor lasers, such as a gallium aluminum arsenide diode laser.

Dyes according to the present invention have the advantageous features of absorption in the IR (preferably near-IR) region; suitability for formulation into aqueous inkjet inks; and facile preparation. Moreover, their high extinction coefficients in the near-IR region means that the dyes appear "invisible" at a concentration suitable for detection by a near-IR detector (e.g. a netpage pen). Accordingly, the dyes of the present invention are especially suitable for use in netpage and Hyperlabel™ applications. None of the dyes known in the prior art has this unique combination of properties.

In particular, dyes according to the present invention comprise water-solubilizing groups, which do not produce significant blue-shifts in the $\lambda_{max}$ of the naphthalocyanine chromophore. Typically, water-soluble phthalocyanines (e.g.

commercially available copper phthalocyanine tetrasulfonate) are blue-shifted compared to their non water-soluble counterparts. The blue-shifting is usually a result of attaching electron-withdrawing groups (e.g. sulfonic acid groups) directly onto the chromophore. As a consequence, water-soluble naphthalocyanines having a $\lambda_{max}$ above about 780 nm are difficult to prepare, especially with non red-shifting metals, such as copper. Copper is an attractive metal to use in IR dyes, due to its low toxicity, low cost and reliable chemistry. However, water-soluble copper naphthalocyanines, having acceptable IR absorption, were hitherto unknown because of the contradictory requirements described above—on the one hand water-solubilizing groups are necessary; on the other hand the water-solubilizing groups blue-shift the $\lambda_{max}$ away from the near-IR region.

In the present invention, the water-solubilizing group (or groups) are distal from the IR chromophore and, hence, do not impact significantly on the $\lambda_{max}$ of the dye. Accordingly, water-soluble naphthalocyanines having a $\lambda_{max}$ in a desired near-IR window are available, using a range of metals and not just red-shifting metals.

An additional advantage of the peripherally substituted dyes of the present invention is that the peripheral substituents impart steric hindrance around the macrocycle, thereby inhibiting intermolecular interactions, such as π-π stacking. The peripheral groups also serve as a useful handle for the attachment of other functionalities which may further reduce intermolecular interactions.

Generally, the naphthalocyanine dyes according to the present invention are synthesized via a cascaded coupling of four dicyanoaryl molecules, although they may also be prepared from the corresponding imidine. Typical dicyanoaryl (1) and imidine (2) starting materials for the cascaded coupling reaction are shown below:

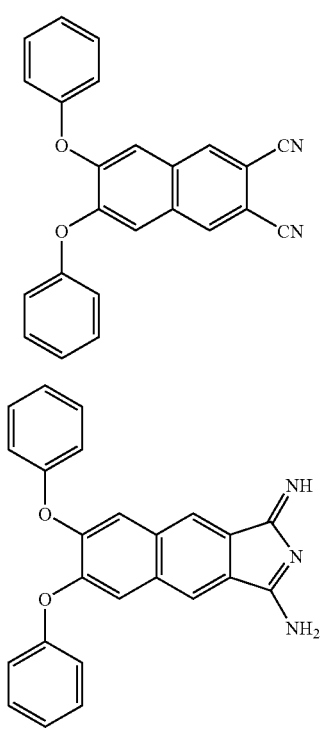

The cascaded base-catalysed macrocyclisation may be facilitated by metal templating, or it may proceed in the absence of a metal. If macrocyclization is performed in the absence of a templating metal, then a metal may be readily inserted into the resultant metal-free naphthalocyanine. Following macrocyclization, the aryl groups (Ar) are typically sulfonated using standard sulfonating conditions (e.g. oleum, chlorosulfonic acid). The aryl groups are sulfonated selectively in the presence of the naphthalocyanine ring.

The groups represented by $R^1$ and $R^2$ may be used for modifying or "tuning" the wavelength of $\lambda_{max}$ of the dye. Electron-donating substituents (e.g. alkoxy) at the ortho positions can produce a red-shift in the dye. In one preferred embodiment of the present invention, $R^1$ and $R^2$ are both $C_{1-8}$ alkoxy groups, preferably butoxy. Butoxy substituents advantageously shift the $\lambda_{max}$ towards longer wavelengths in the near infrared, which are preferable for detection by commercially available lasers. In another preferred embodiment $R^1$ and $R^2$ are both hydrogen, which provides an expeditious synthesis of the requisite naphthalocyanines.

Optionally, the sulfonic acid or sulfonic acid salt is of formula: —$SO_3Z$. Preferably, Z is selected from H, $Li^+$, $Na^+$, $K^+$ or an ammonium cation, such as $N^+(R^m)(R^n)(R^s)(R^t)$ wherein $R^m$, $R^n$, $R^s$, $R^t$ may be the same or different and are independently selected from H, $C_{1-8}$ alkyl (e.g. methyl, ethyl, cyclohexyl, cyclopentyl, tert-butyl, iso-propyl etc.), $C_{6-12}$ arylalkyl (e.g. benzyl, phenylethyl etc.) or $C_{6-12}$ aryl (e.g. phenyl, naphthyl etc.). As mentioned above, sulfonic acid substituents may be introduced under standard sulfonating conditions. Conversion of the acid group to its salt form can be effected using, for example, a metal hydroxide reagent (e.g. LiOH, NaOH or KOH) or a metal bicarbonate (e.g. $NaHCO_3$). Non-metal salts may also be prepared using, for example, an ammonium hydroxide (e.g. $Bu_4NOH$, $NH_4OH$ etc.).

Optionally, the sulfonamide group is of general formula —$SO_2NR^pR^q$, wherein $R^p$ and $R^q$ are independently selected from H, $C_{1-8}$ alkyl (e.g. methyl, ethyl, cyclohexyl, cyclopentyl, tert-butyl, iso-propyl etc.), —$(CH_2CH_2O)_eR^e$ (wherein e is an integer from 2 to 5000 and $R^e$ is H, $C_{1-8}$ alkyl or $C(O)C_{1-8}$ alkyl), $C_{6-12}$ arylalkyl (e.g. benzyl, phenylethyl etc.) or $C_{6-12}$ aryl (e.g. phenyl, methoxyphenyl etc.). Sulfonamides may be readily prepared from the corresponding sulfonic acids. Moreover, mixtures of sulfonic acids/salts and sulfonamides are also contemplated within the scope of the present invention. For example, each dye molecule may comprise 1, 2, 3 or 4 sulfonamide groups and 1, 2, 3 or 4 sulfonic acid ammonium salts.

Optionally, the sulfonamide group is of general formula —$SO_2NHR^p$, wherein $R^p$ is of formula (V):

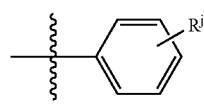

(II)

wherein:
$R^j$ is selected from H, $C_{1-12}$ alkoxy, —$(OCH_2CH_2)_dOR^d$;
d is an integer from 2 to 5000; and
$R^d$ is H, $C_{1-8}$ alkyl or $C(O)C_{1-8}$ alkyl.
$R^j$ may be positioned at the ortho, meta or para positions.

Optionally, each of the Ar groups is substituted with one sulfonic acid, sulfonic acid salt or sulfonamide group, giving a total of 8 water-solubilizing groups.

Optionally, X is O. Optionally, each Ar group is phenyl.
Optionally, the dye is of formula (III):

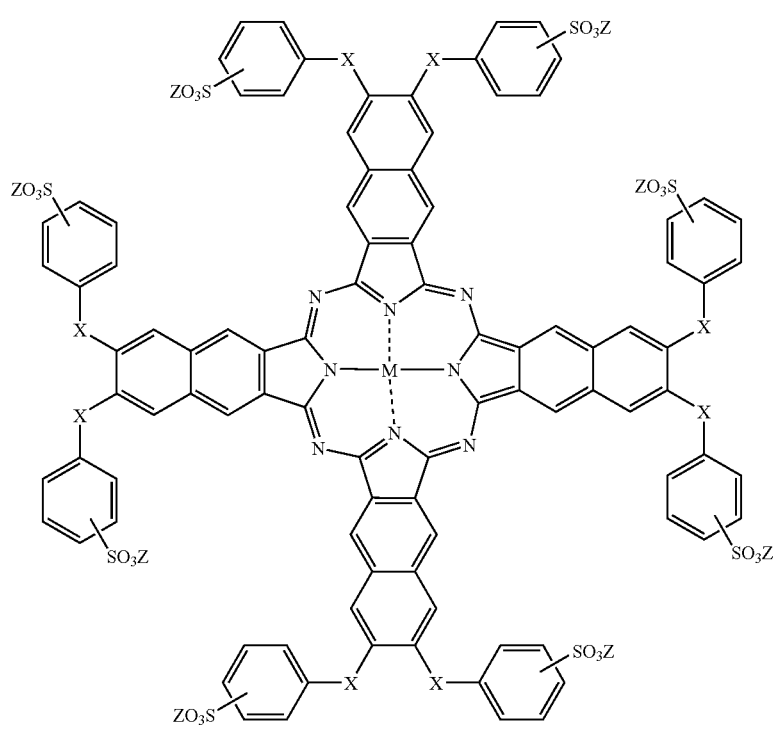
(III)
wherein:
Z is H, Li, Na, K or $N^+(R^m)(R^n)(R^s)(R^t)$; and
$R^m$, $R^n$, $R^s$, $R^t$ may be the same or different and are independently selected from H, $C_{1-8}$ alkyl, $C_{6-12}$ arylalkyl and $C_{6-12}$ aryl.
Typically, each —$SO_3Z$ group is at a para position due to the para-directing effect of the hetero atoms (e.g. O) attached to the naphthalocyanine ring.
Optionally, the dye is of formula (IV[d1]):
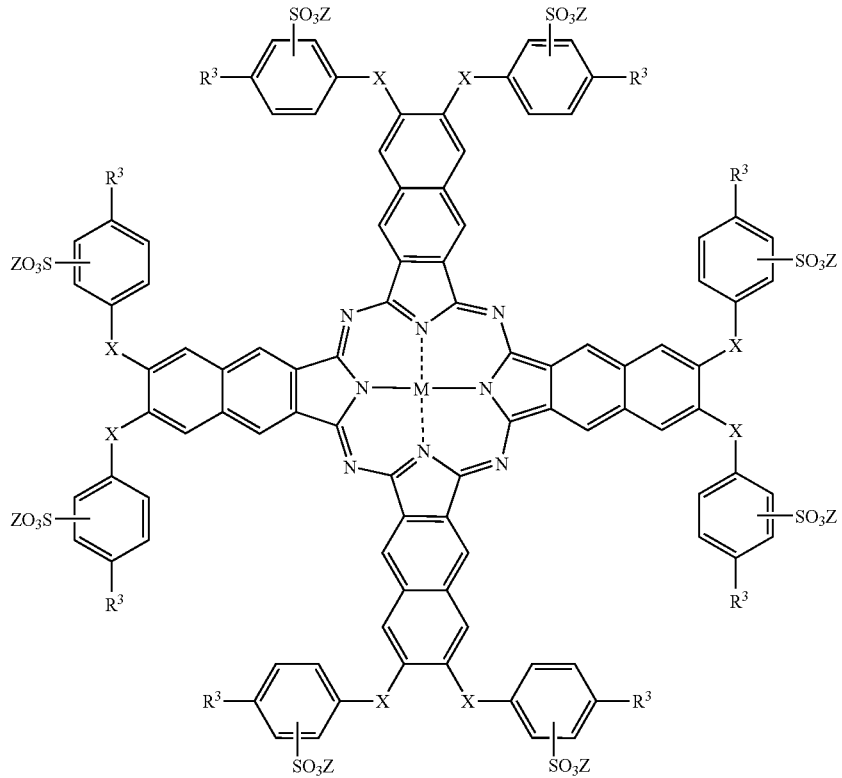
(IV)

wherein:

Z is H, Li, Na, K or $N^+(R^m)(R^n)(R^s)(R^t)$;

$R^m$, $R^n$, $R^s$, $R^t$ may be the same or different and are independently selected from H, $C_{1-8}$ alkyl, $C_{6-12}$ arylalkyl and $C_{6-12}$ aryl; and $R^3$ is selected from $C_{1-12}$ alkyl, $C_{1-12}$ alkoxy, $C_{1-12}$ arylalkyl, $C_{1-12}$ arylalkoxy, $-(OCH_2CH_2)_dOR^d$, cyano, halogen, amino, hydroxyl, thiol, $-SR^v$, $-NR^uR^v$, nitro, phenyl, phenoxy, $-CO_2R^v$, $-C(O)R^v$, $-OCOR^v$, $-NHC(O)R^v$, $-CONR^uR^v$ or $-CONR^uR^v$.

Optionally, $R^3$ is $C_{1-6}$ alkyl or $C_{1-6}$ alkoxy.

Dyes according to formula (IV) are advantageous because the $R^3$ groups block the para-positions. This typically forces the sulfonic groups to substitute at the ortho or meta-positions, preferably the meta-positions. With the sulfonic acid groups directed to the meta-positions, their mesomeric electron-withdrawing effects are minimized, which consequently minimizes any blue-shift in $\lambda_{max}$ resulting from the substitution.

Optionally, the metal group M is selected from $Si(A^1)(A^2)$, $Ge(A^1)(A^2)$, $Ga(A^1)$, Mg, $Al(A^1)$, TiO, $Ti(A^1)(A^2)$, ZrO, $Zr(A^1)(A^2)$, VO, $V(A^1)(A^2)$, Mn, $Mn(A^1)$, Fe, $Fe(A^1)$, Co, Ni, Cu, Zn, Sn, $Sn(A^1)(A^2)$, Pb, $Pb(A^1)(A^2)$, Pd and Pt.

$A^1$ and $A^2$ are axial ligands, which may be the same or different, and are selected from —OH, halogen or $-OR^3$.

$R^3$ is selected from $SO_3Z$ (wherein Z is as previously defined), $C_{1-12}$ alkyl, $C_{5-12}$ aryl, $C_{5-12}$ arylalkyl or $Si(R^x)(R^y)(R^z)$, wherein $R^x$, $R^y$ and $R^z$ may be the same or different and are selected from $C_{1-12}$ alkyl, $C_{5-12}$ aryl, $C_{5-12}$ arylalkyl, $C_{1-12}$ alkoxy, $C_{5-12}$ aryloxy or $C_{5-12}$ arylalkoxy.

Optionally, the metal group M is selected from $SnCl_2$, V=O, Cu or Ga(OH).

The term "aryl" is used herein to refer to an aromatic group, such as phenyl, naphthyl or triptycenyl. $C_{6-12}$ aryl, for example, refers to an aromatic group having from 6 to 12 carbon atoms, excluding any substituents. The term "arylene", of course, refers to divalent groups corresponding to the monovalent aryl groups described above. Any reference to aryl implicitly includes arylene, where appropriate.

The term "heteroaryl" refers to an aryl group, where 1, 2, 3 or 4 carbon atoms are replaced by a heteroatom selected from N, O or S. Examples of heteroaryl (or heteroaromatic) groups include pyridyl, benzimidazolyl, indazolyl, quinolinyl, isoquinolinyl, indolinyl, isoindolinyl, indolyl, isoindolyl, furanyl, thiophenyl, pyrrolyl, thiazolyl, imidazolyl, oxazolyl, isoxazolyl, pyrazolyl, isoxazolonyl, piperazinyl, pyrimidinyl, piperidinyl, morpholinyl, pyrrolidinyl, isothiazolyl, triazolyl, oxadiazolyl, thiadiazolyl, pyridyl, pyrimidinyl, benzopyrimidinyl, benzotriazole, quinoxalinyl, pyridazyl, coumarinyl etc. The term "heteroarylene", of course, refers to divalent groups corresponding to the monovalent heteroaryl groups described above. Any reference to heteroaryl implicitly includes heteroarylene, where appropriate.

Unless specifically stated otherwise, aryl, arylene, heteroaryl and heteroarylene groups may be optionally substituted with 1, 2, 3, 4 or 5 of the substituents described below.

Where reference is made to optionally substituted groups (e.g. in connection with bridged cyclic groups, aryl groups or heteroaryl groups), the optional substituent(s) are independently selected from $C_{1-8}$ alkyl, $C_{1-8}$ alkoxy, $-(OCH_2CH_2)_d OR^d$ (wherein d is an integer from 2 to 5000 and $R^d$ is H, $C_{1-8}$ alkyl or $C(O)C_{1-8}$ alkyl), cyano, halogen, amino, hydroxyl, thiol, $-SR^v$, $-NR^uR^v$, nitro, phenyl, phenoxy, $-CO_2R^v$, $-C(O)R^v$, $-OCOR^v$, $-SO_2R^v$, $-OSO_2R^v$, $-SO_2OR^v$, $-NHC(O)R^v$, $-CONR^uR^v$, $-CONR^uR^v$, $-SO_2NR^uR^v$, wherein $R^u$ and $R^v$ are independently selected from hydrogen, $C_{1-12}$ alkyl, phenyl or phenyl-$C_{1-8}$ alkyl (e.g. benzyl). Where, for example, a group contains more than one substituent, different substituents can have different $R^u$ or $R^v$ groups. For example, a naphthyl group may be substituted with three substituents: $-SO_2NHPh$, $-CO_2Me$ group and $-NH_2$.

The term "alkyl" is used herein to refer to alkyl groups in both straight and branched forms. The alkyl group may be interrupted with 1, 2 or 3 heteroatoms selected from O, N or S. The alkyl group may also be interrupted with 1, 2 or 3 double and/or triple bonds. However, the term "alkyl" usually refers to alkyl groups having no heteroatom interruptions or double or triple bond interruptions. Where "alkenyl" groups are specifically mentioned, this is not intended to be construed as a limitation on the definition of "alkyl" above.

The term "alkyl" also includes halogenoalkyl groups: A $C_{1-12}$ alkyl group may, for example, have up to 5 hydrogen atoms replaced by halogen atoms. For example, the group $-OC(O)C_{1-12}$ alkyl specifically includes $-OC(O)CF_3$.

Where reference is made to, for example, $C_{1-12}$ alkyl, it is meant the alkyl group may contain any number of carbon atoms between 1 and 12. Unless specifically stated otherwise, any reference to "alkyl" means $C_{1-12}$ alkyl, preferably $C_{1-6}$alkyl.

The term "alkyl" also includes cycloalkyl groups. As used herein, the term "cycloalkyl" includes cycloalkyl, polycycloalkyl, and cycloalkenyl groups, as well as combinations of these with linear alkyl groups, such as cycloalkylalkyl groups. The cycloalkyl group may be interrupted with 1, 2 or 3 heteroatoms selected from O, N or S. However, the term "cycloalkyl" usually refers to cycloalkyl groups having no heteroatom interruptions. Examples of cycloalkyl groups include cyclopentyl, cyclohexyl, cyclohexenyl, cyclohexylmethyl and adamantyl groups.

The term "arylalkyl" refers to groups such as benzyl, phenylethyl and naphthylmethyl.

The term "halogen" or "halo" is used herein to refer to any of fluorine, chlorine, bromine and iodine. Usually, however, halogen refers to chlorine or fluorine substituents.

Chiral compounds described herein have not been given stereo-descriptors. However, when compounds may exist in stereoisomeric forms, then all possible stereoisomers and mixtures thereof are included (e.g. enantiomers, diastereomers and all combinations including racemic mixtures etc.).

Likewise, when compounds may exist in a number of regioisomeric forms, then all possible regioisomers and mixtures thereof are included.

For the avoidance of doubt, the term "a" (or "an"), in phrases such as "comprising a", means "at least one" and not "one and only one". Where the term "at least one" is specifically used, this should not be construed as having a limitation on the definition of "a".

Throughout the specification, the term "comprising", or variations such as "comprise" or "comprises", should be construed as including a stated element, integer or step, but not excluding any other element, integer or step.

Inkjet Inks

The present invention also provides an inkjet ink. Preferably, the inkjet ink is a water-based inkjet ink.

Water-based inkjet ink compositions are well known in the literature and, in addition to water, may comprise additives, such as co-solvents, biocides, sequestering agents, humectants, pH adjusters, viscosity modifiers, penetrants, wetting agents, surfactants etc.

Co-solvents are typically water-soluble organic solvents. Suitable water-soluble organic solvents include $C_{1-4}$ alkyl alcohols, such as ethanol, methanol, butanol, propanol, and 2-propanol; glycol ethers, such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-isopropyl ether, diethylene glycol mono-isopropyl ether, ethylene glycol mono-n-butyl ether, diethylene glycol mono-n-butyl ether, triethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-isopropyl ether, dipropylene glycol monomethyl ether, dipropylene glycol monoethyl ether, dipropylene glycol mono-n-propyl ether, dipropylene glycol mono-isopropyl ether, propylene glycol mono-n-butyl ether, and dipropylene glycol mono-n-butyl ether; formamide, acetamide, dimethyl sulfoxide, sorbitol, sorbitan, glycerol monoacetate, glycerol diacetate, glycerol triacetate, and sulfolane; or combinations thereof.

Other useful water-soluble organic solvents include polar solvents, such as 2-pyrrolidone, N-methylpyrrolidone, ϵ-caprolactam, dimethyl sulfoxide, sulfolane, morpholine, N-ethylmorpholine, 1,3-dimethyl-2-imidazolidinone and combinations thereof.

The inkjet ink may contain a high-boiling water-soluble organic solvent which can serve as a wetting agent or humectant for imparting water retentivity and wetting properties to the ink composition. Such a high-boiling water-soluble organic solvent includes one having a boiling point of 180° C. or higher. Examples of the water-soluble organic solvent having a boiling point of 180° C. or higher are ethylene glycol, propylene glycol, diethylene glycol, pentamethylene glycol, trimethylene glycol, 2-butene-1,4-diol, 2-ethyl-1,3-hexanediol, 2-methyl-2,4-pentanediol, tripropylene glycol monomethyl ether, dipropylene glycol monoethyl glycol, dipropylene glycol monoethyl ether, dipropylene glycol monomethyl ether, dipropylene glycol, triethylene glycol monomethyl ether, tetraethylene glycol, triethylene glycol, diethylene glycol monobutyl ether, diethylene glycol monoethyl ether, diethylene glycol monomethyl ether, tripropylene glycol, polyethylene glycols having molecular weights of 2000 or lower, 1,3-propylene glycol, isopropylene glycol, isobutylene glycol, 1,4-butanediol, 1,3-butanediol, 1,5-pentanediol, 1,6-hexanediol, glycerol, erythritol, pentaerythritol and combinations thereof.

The total water-soluble organic solvent content in the inkjet ink is preferably about 5 to 50% by weight, more preferably 10 to 30% by weight, based on the total ink composition.

Other suitable wetting agents or humectants include saccharides (including monosaccharides, oligosaccharides and polysaccharides) and derivatives thereof (e.g. maltitol, sorbitol, xylitol, hyaluronic salts, aldonic acids, uronic acids etc.)

The inkjet ink may also contains a penetrant for accelerating penetration of the aqueous ink into the recording medium. Suitable penetrants include polyhydric alcohol alkyl ethers (glycol ethers) and/or 1,2-alkyldiols. Examples of suitable polyhydric alcohol alkyl ethers are ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, ethylene glycol mono-n-propyl ether, ethylene glycol mono-isopropyl ether, diethylene glycol mono-isopropyl ether, ethylene glycol mono-n-butyl ether, diethylene glycol mono-n-butyl ether, triethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-isopropyl ether, dipropylene glycol monomethyl ether, dipropylene glycol monoethyl ether, dipropylene glycol mono-n-propyl ether, dipropylene glycol mono-isopropyl ether, propylene glycol mono-n-butyl ether, and dipropylene glycol mono-n-butyl ether. Examples of suitable 1,2-alkyldiols are 1,2-pentanediol and 1,2-hexanediol. The penetrant may also be selected from straight-chain hydrocarbon diols, such as 1,3-propanediol, 1,4-butanediol, 1,5-pentanediol, 1,6-hexanediol, 1,7-heptanediol, and 1,8-octanediol. Glycerol or urea may also be used as penetrants.

The amount of penetrant is preferably in the range of 1 to 20% by weight, more preferably 1 to 10% by weight, based on the total ink composition.

The inkjet ink may also contain a surface active agent, especially an anionic surface active agent and/or a nonionic surface active agent. Useful anionic surface active agents include sulfonic acid types, such as alkanesulfonic acid salts, α-olefinsulfonic acid salts, alkylbenzenesulfonic acid salts, alkylnaphthalenesulfonic acids, acylmethyltaurines, and dialkylsulfosuccinic acids; alkylsulfuric ester salts, sulfated oils, sulfated olefins, polyoxyethylene alkyl ether sulfuric ester salts; carboxylic acid types, e.g., fatty acid salts and alkylsarcosine salts; and phosphoric acid ester types, such as alkylphosphoric ester salts, polyoxyethylene alkyl ether phosphoric ester salts, and glycerophosphoric ester salts. Specific examples of the anionic surface active agents are sodium dodecylbenzenesulfonate, sodium laurate, and a polyoxyethylene alkyl ether sulfate ammonium salt.

Suitable nonionic surface active agents include ethylene oxide adduct types, such as polyoxyethylene alkyl ethers, polyoxyethylene alkylphenyl ethers, polyoxyethylene alkyl esters, and polyoxyethylene alkylamides; polyol ester types, such as glycerol alkyl esters, sorbitan alkyl esters, and sugar alkyl esters; polyether types, such as polyhydric alcohol alkyl ethers; and alkanolamide types, such as alkanolamine fatty acid amides. Specific examples of nonionic surface active agents are ethers such as polyoxyethylene nonylphenyl ether, polyoxyethylene octylphenyl ether, polyoxyethylene dodecylphenyl ether, polyoxyethylene alkylallyl ether, polyoxyethylene oleyl ether, polyoxyethylene lauryl ether, and polyoxyalkylene alkyl ethers (e.g. polyoxyethylene alkyl ethers); and esters, such as polyoxyethylene oleate, polyoxyethylene oleate ester, polyoxyethylene distearate, sorbitan laurate, sorbitan monostearate, sorbitan mono-oleate, sorbitan sesquioleate, polyoxyethylene mono-oleate, and polyoxyethylene stearate. Acetylene glycol surface active agents, such as 2,4,7,9-tetramethyl-5-decyne-4,7-diol, 3,6-dimethyl-4-octyne-3,6-diol or 3,5-dimethyl-1-hexyn-3-ol, may also be used.

The inkjet ink may contain a pH adjuster for adjusting its pH to 7 to 9. Suitable pH adjusters include basic compounds, such as sodium hydroxide, potassium hydroxide, lithium hydroxide, sodium carbonate, sodium hydrogencarbonate, potassium carbonate, potassium hydrogencarbonate, lithium carbonate, sodium phosphate, potassium phosphate, lithium phosphate, potassium dihydrogenphosphate, dipotassium hydrogenphosphate, sodium oxalate, potassium oxalate, lithium oxalate, sodium borate, sodium tetraborate, potassium hydrogenphthalate, and potassium hydrogentartrate; ammonia; and amines, such as methylamine, ethylamine, diethylamine, trimethylamine, triethylamine, tris(hydroxymethyl)aminomethane hydrochloride, triethanolamine, diethanolamine, diethylethanolamine, triisopropanolamine, butyldiethanolamine, morpholine, and propanolamine.

The inkjet ink may also include a biocide, such as benzoic acid, dichlorophene, hexachlorophene, sorbic acid, hydroxybenzoic esters, sodium dehydroacetate, 1,2-benthiazolin-3-one, 3,4-isothiazolin-3-one or 4,4-dimethyloxazolidine.

The inkjet ink may also contain a sequestering agent, such as ethylenediaminetetraacetic acid (EDTA).

The inkjet ink may also contain a singlet oxygen quencher. The presence of singlet oxygen quencher(s) in the ink reduces the propensity for the IR-absorbing dye to degrade. The quencher consumes any singlet oxygen generated in the vicinity of the dye molecules and, hence, minimizes their degradation. An excess of singlet oxygen quencher is advantageous for minimizing degradation of the dye and retaining its IR-absorbing properties over time. Preferably, the singlet oxygen quencher is selected from ascorbic acid, 1,4-diazabicyclo-[2.2.2]octane (DABCO), azides (e.g. sodium azide), histidine or tryptophan.

Inkjet Printers

The present invention also provides an inkjet printer comprising a printhead in fluid communication with at least one ink reservoir, wherein said ink reservoir comprises an inkjet ink as described above.

Inkjet printers, such as thermal bubble-jet and piezoelectric printers, are well known in the art and will form part of the skilled person's common general knowledge. The printer may be a high-speed inkjet printer. The printer is preferably a pagewidth printer. Preferred inkjet printers and printheads for use in the present invention are described in the following patent applications, all of which are incorporated herein by reference in their entirety.

429. The electrical connectors 428 and 429 correspond with flexible connectors (not shown). The electrical connectors include contact areas 450 and 460 that, in use, are positioned in contact with corresponding output connectors from a SoPEC chip (not shown). Data from the SoPEC chip passes along the electrical connectors 428 and 429, and is distributed to respective ends of the first and second printhead ICs 425 and 426.

Figure 18:
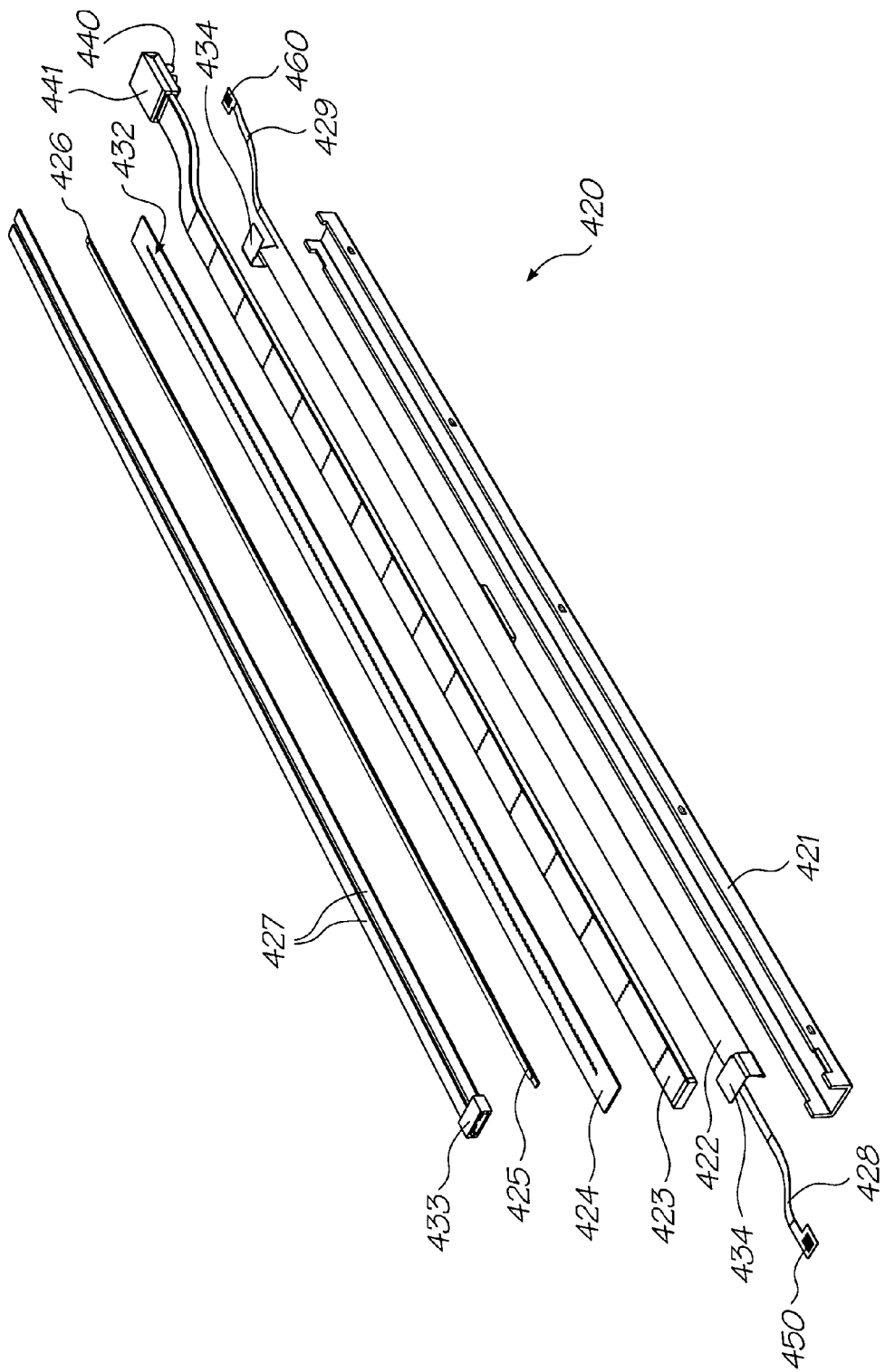
FIG. 18 an exploded perspective view of the bi-lithic printhead of FIG. 17.
Figure 19:
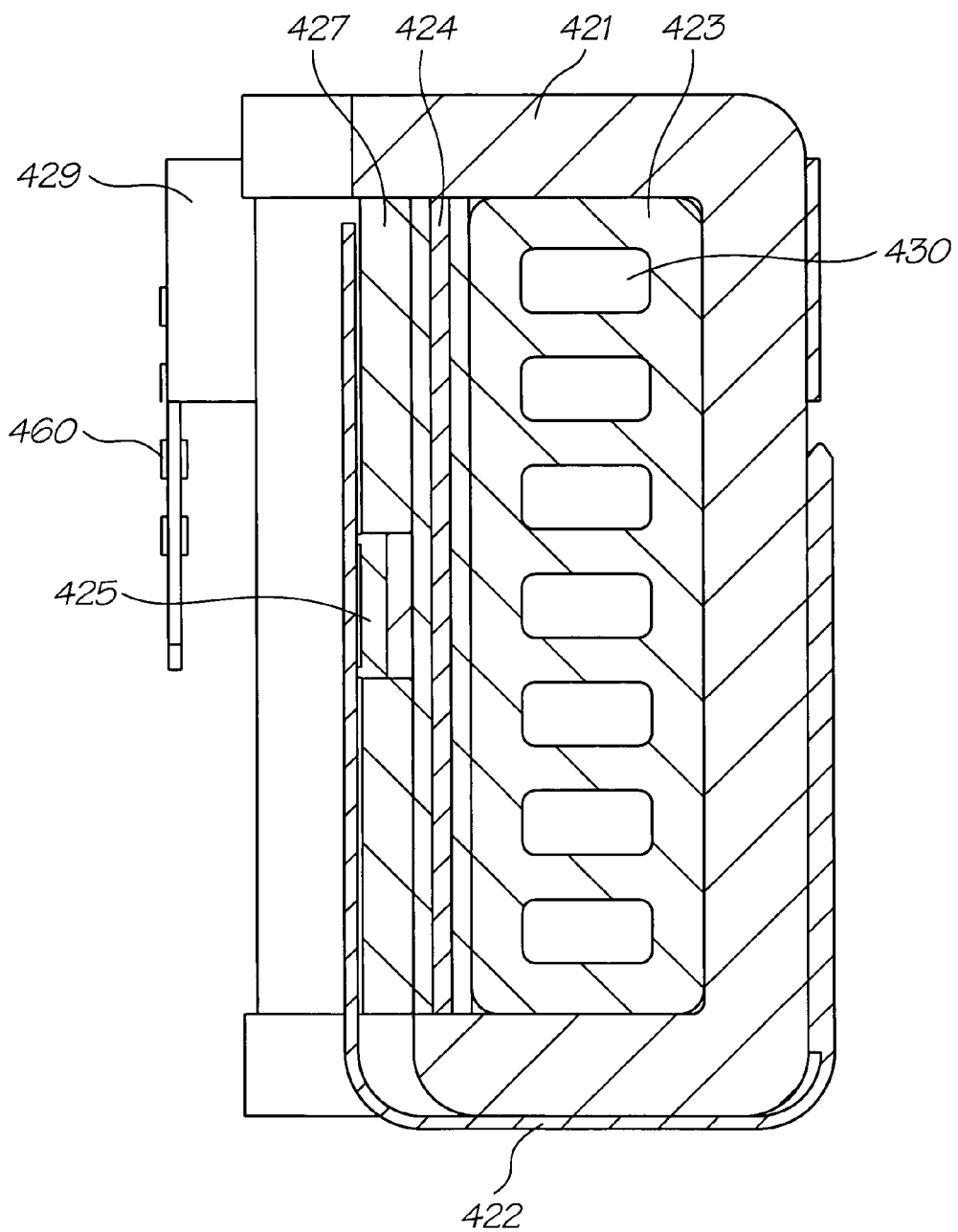
FIG. 19 is a sectional view through one end of the bi-lithic printhead of FIG. 17.

As shown in FIG. 19, the ink distribution molding 423 includes a plurality of elongate conduits 430 that distribute fluids (ie, colored inks, infrared ink and fixative) and pressurized air from the air pump along the length of the printhead 420 (FIG. 18). Sets of fluid apertures 431 (FIG. 20) disposed along the length of the ink distribution molding 423 distribute the fluids and air from the conduits 430 to the ink distribution plate 424. The fluids and air are supplied via nozzles 440 formed on a plug 441 (FIG. 21), which plugs into a corresponding socket (not shown) in the printer.

Figure 20:
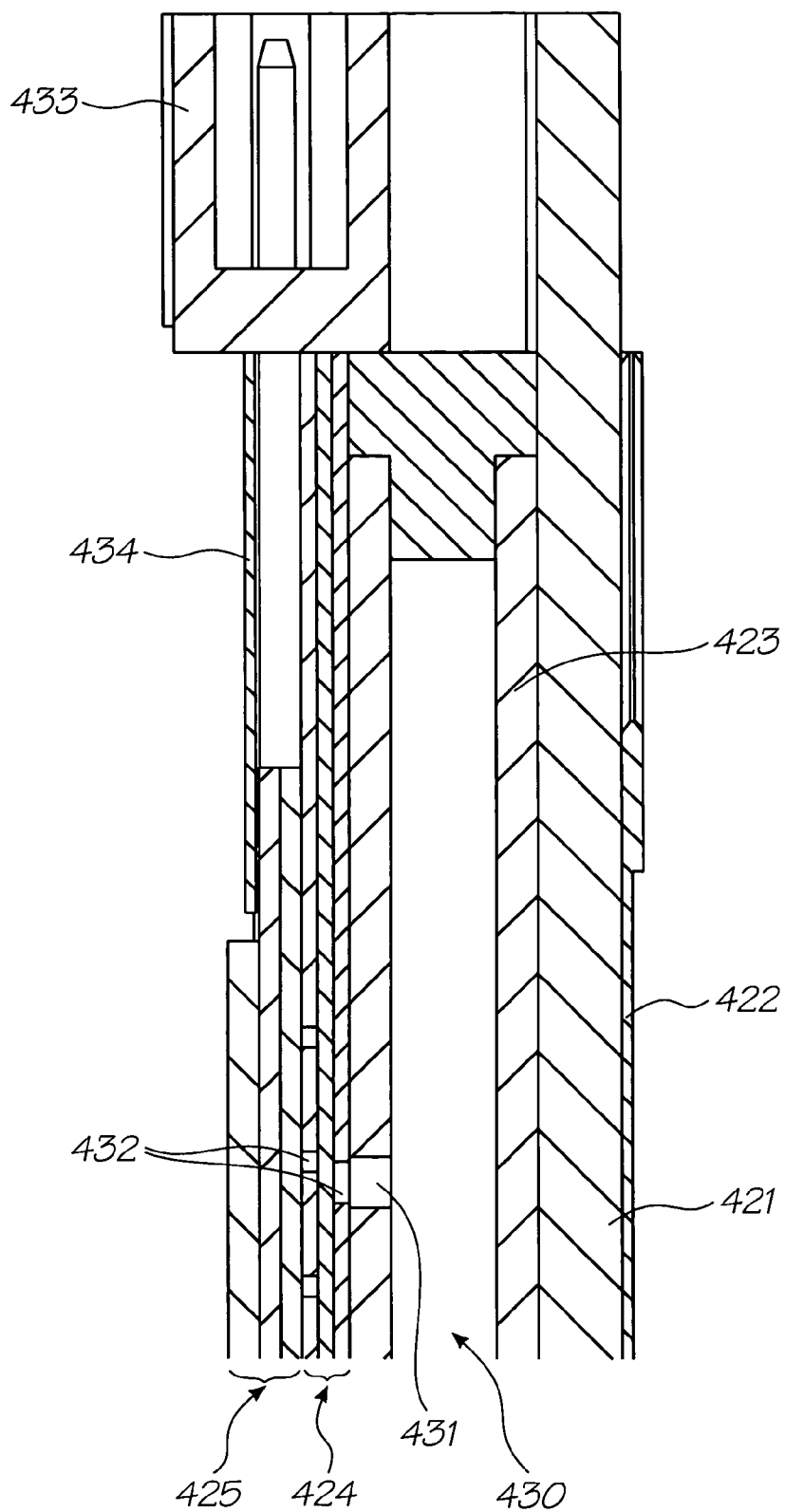
FIG. 20 is a longitudinal sectional view through the bi-lithic printhead of FIG. 17.
Figure 21A:
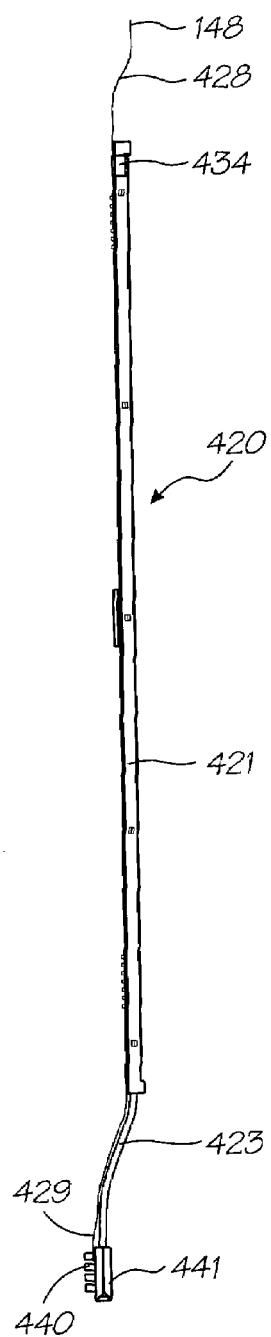
FIGS. 21(a) to 21(d) show a side elevation, plan view, opposite side elevation and reverse plan view, respectively, of the bi-lithic printhead of FIG. 17.
Figure 21B:
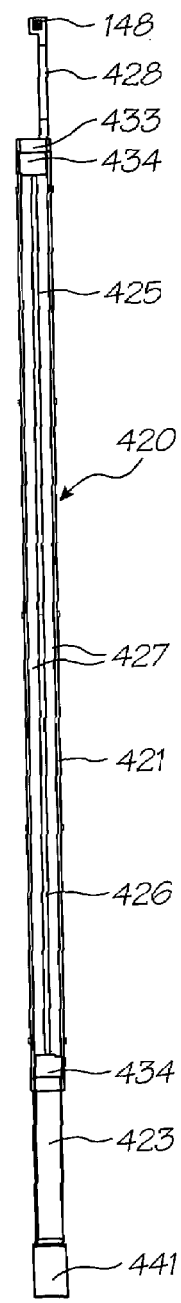
Figure 21C:
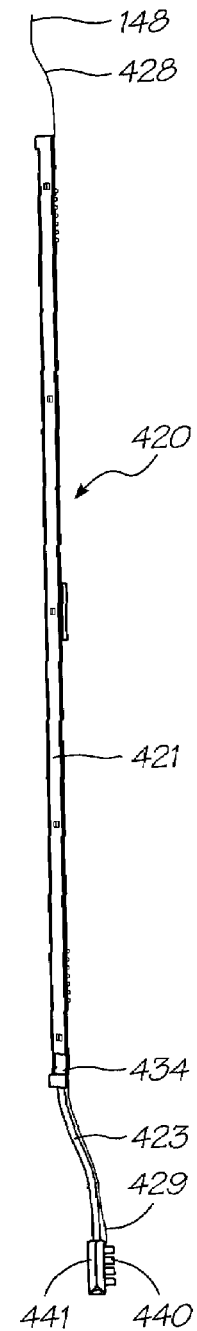
Figure 21D:
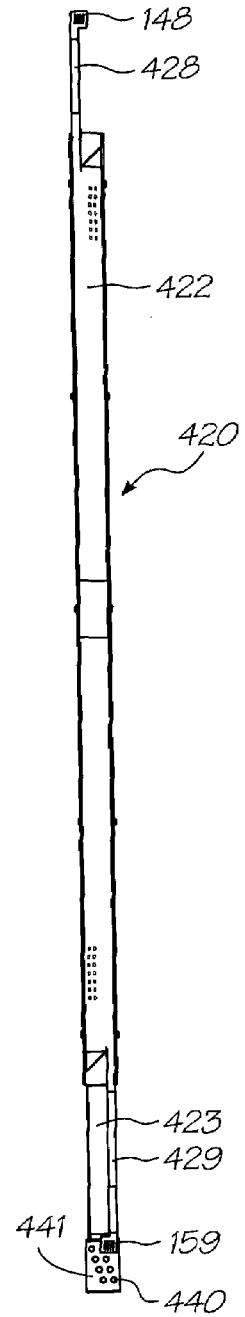

The distribution plate 424 is a multi-layer construction configured to take fluids provided locally from the fluid apertures 431 and distribute them through smaller distribution apertures 432 into the printhead ICs 425 and 426 (as shown in FIG. 20).

The printhead ICs 425 and 426 are positioned end to end, and are held in contact with the distribution plate 424 so that ink from the smaller distribution apertures 432 can be fed into corresponding apertures (not shown) in the printhead ICs 425 and 426.

| 10/302,274 | 6692108 | 6672709 | 10/303,348 | 6672710 | 6669334 |
| 10/302,668 | 10/302,577 | 6669333 | 10/302,618 | 10/302,617 | 10/302,297 |

Printhead

A Memjet printer generally has two printhead integrated circuits that are mounted adjacent each other to form a pagewidth printhead. Typically, the printhead ICs can vary in size from 2 inches to 8 inches, so several combinations can be used to produce, say, an A4 pagewidth printhead. For example two printhead ICs of 7 and 3 inches, 2 and 4 inches, or 5 and 5 inches could be used to create an A4 printhead (the notation is 7:3). Similarly 6 and 4 (6:4) or 5 and 5 (5:5) combinations can be used. An A3 printhead can be constructed from 8 and 6-inch printhead integrated circuits, for example. For photographic printing, particularly in camera, smaller printheads can be used. It will also be appreciated that a single printhead integrated circuit, or more than two such circuits, can also be used to achieve the required printhead width.

A preferred printhead embodiment of the pinthead will now be described with reference to FIGS. 17 and 18. A printhead 420 takes the form of an elongate unit. As best shown in FIG. 18, the components of the printhead 420 include a support member 421, a flexible PCB 422, an ink distribution molding 423, an ink distribution plate 424, a MEMS printhead comprising first and second printhead integrated circuits (ICs) 425 and 426, and busbars 427.

The support member 421 is can be formed from any suitable material, such as metal or plastic, and can be extruded, molded or formed in any other way. The support member 421 should be strong enough to hold the other components in the appropriate alignment relative to each other whilst stiffening and strengthening the printhead as a whole.

The flexible PCB extends the length of the printhead 420 and includes first and second electrical connectors 428 and The busbars 427 are relatively high-capacity conductors positioned to provide drive current to the actuators of the printhead nozzles (described in detail below). As best shown in FIG. 20, the busbars 427 are retained in position at one end by a socket 433, and at both ends by wrap-around wings 434 of the flexible PCB 422. The busbars also help hold the printhead ICs 425 in position.

As shown best in FIG. 18, when assembled, the flexible PCB 422 is effectively wrapped around the other components, thereby holding them in contact with each other. Notwithstanding this binding effect, the support member 421 provides a major proportion of the required stiffness and strength of the printhead 420 as a whole.

Two forms of printhead nozzles ("thermal bend actuator" and "bubble forming heater element actuator"), suitable for use in the printhead described above, will now be described.

Thermal Bend Actuator

In the thermal bend actuator, there is typically provided a nozzle arrangement having a nozzle chamber containing ink and a thermal bend actuator connected to a paddle positioned within the chamber. The thermal actuator device is actuated so as to eject ink from the nozzle chamber. The preferred embodiment includes a particular thermal bend actuator which includes a series of tapered portions for providing conductive heating of a conductive trace. The actuator is connected to the paddle via an arm received through a slotted wall of the nozzle chamber. The actuator arm has a mating shape so as to mate substantially with the surfaces of the slot in the nozzle chamber wall.

Figure 22A:
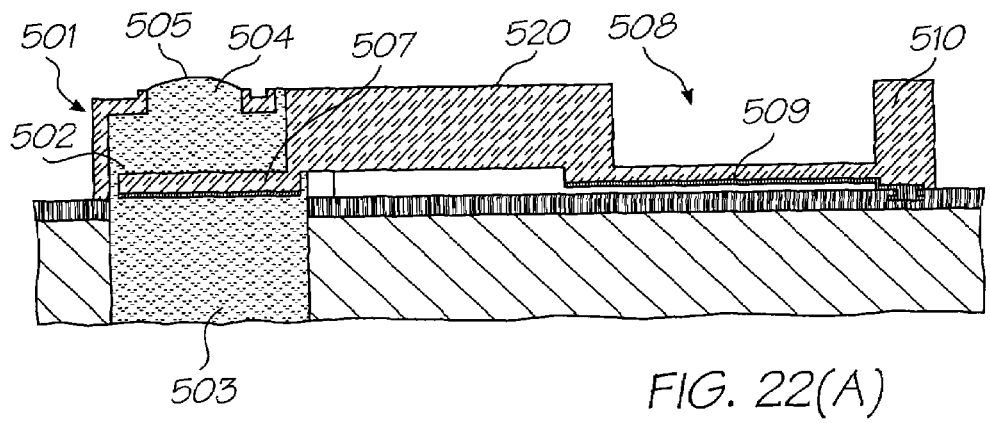
FIGS. 22(a) to 22(c) show the basic operational principles of a thermal bend actuator.
Figure 22B:
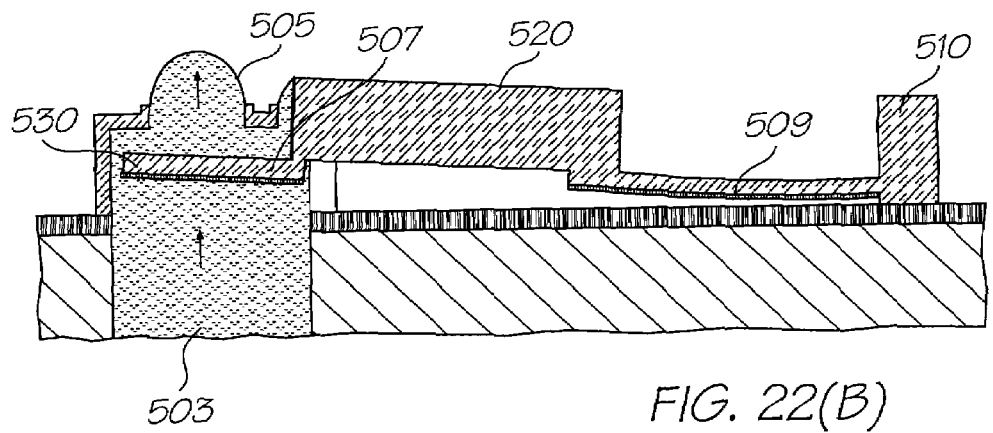
Figure 22C:
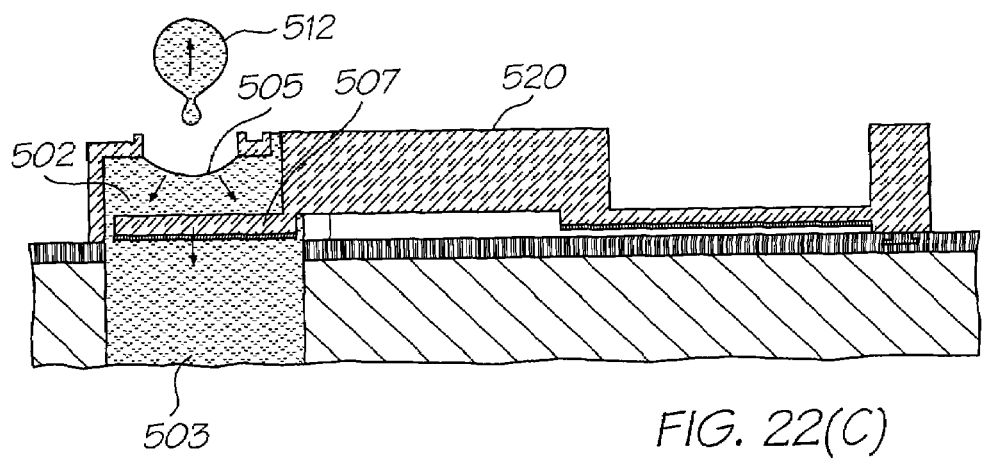

Turning initially to FIGS. 22(a)-(c), there is provided schematic illustrations of the basic operation of a nozzle arrangement of this embodiment. A nozzle chamber 501 is provided filled with ink 502 by means of an ink inlet channel 503 which can be etched through a wafer substrate on which the nozzle chamber 501 rests. The nozzle chamber 501 further includes an ink ejection port 504 around which an ink meniscus forms.

Inside the nozzle chamber 501 is a paddle type device 507 which is interconnected to an actuator 508 through a slot in the wall of the nozzle chamber 501. The actuator 508 includes a heater means e.g. 509 located adjacent to an end portion of a post 510. The post 510 is fixed to a substrate.

When it is desired to eject a drop from the nozzle chamber 501, as illustrated in FIG. 22(b), the heater means 509 is heated so as to undergo thermal expansion. Preferably, the heater means 509 itself or the other portions of the actuator 508 are built from materials having a high bend efficiency where the bend efficiency is defined as:

$$\text{bend efficiency} = \frac{\text{Young's Modulus} \times (\text{Coefficient of thermal Expasion})}{\text{Density} \times \text{Specific Heat Capacity}}$$

A suitable material for the heater elements is a copper nickel alloy which can be formed so as to bend a glass material.

The heater means 509 is ideally located adjacent the end portion of the post 510 such that the effects of activation are magnified at the paddle end 507 such that small thermal expansions near the post 510 result in large movements of the paddle end.

The heater means 509 and consequential paddle movement causes a general increase in pressure around the ink meniscus 505 which expands, as illustrated in FIG. 22(b), in a rapid manner. The heater current is pulsed and ink is ejected out of the port 504 in addition to flowing in from the ink channel 503.

Subsequently, the paddle 507 is deactivated to again return to its quiescent position. The deactivation causes a general reflow of the ink into the nozzle chamber. The forward momentum of the ink outside the nozzle rim and the corresponding backflow results in a general necking and breaking off of the drop 512 which proceeds to the print media. The collapsed meniscus 505 results in a general sucking of ink into the nozzle chamber 502 via the ink flow channel 503. In time, the nozzle chamber 501 is refilled such that the position in FIG. 22(a) is again reached and the nozzle chamber is subsequently ready for the ejection of another drop of ink.

Figure 23:
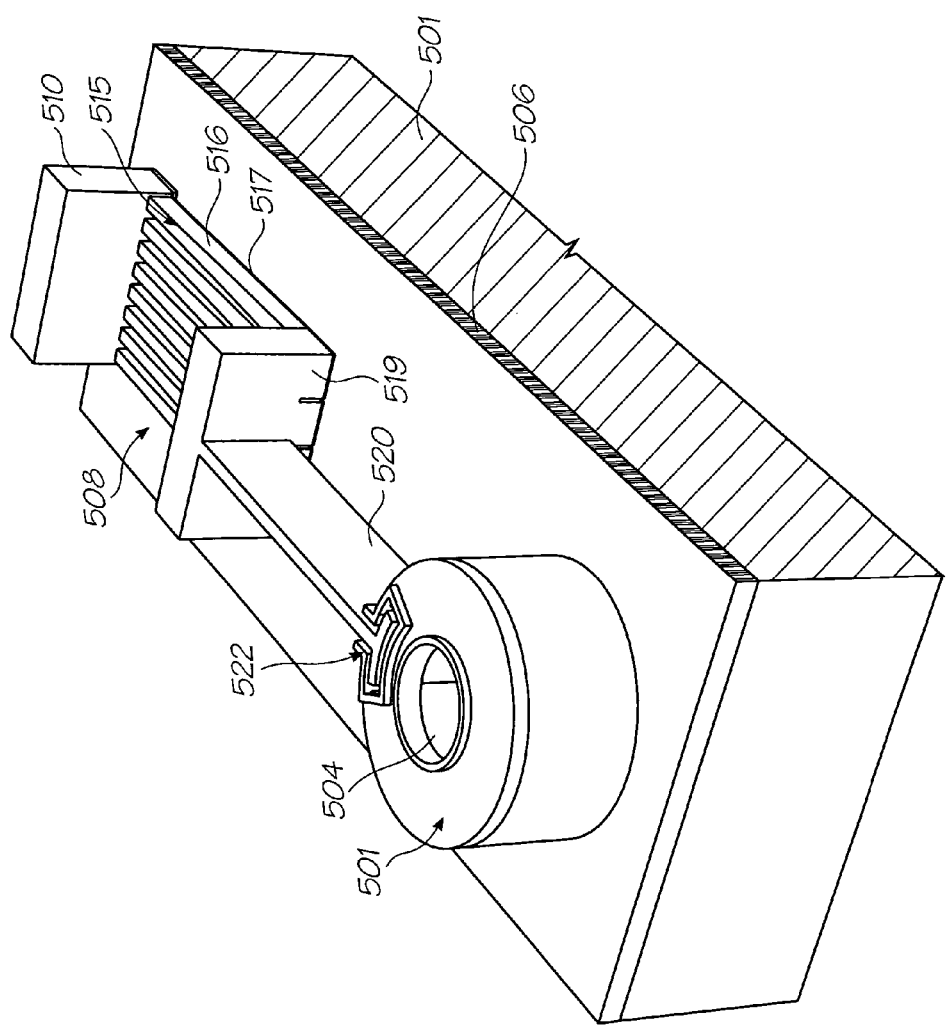
FIG. 23 shows a three dimensional view of a single ink jet nozzle arrangement constructed in accordance with FIG. 22.
Figure 24:
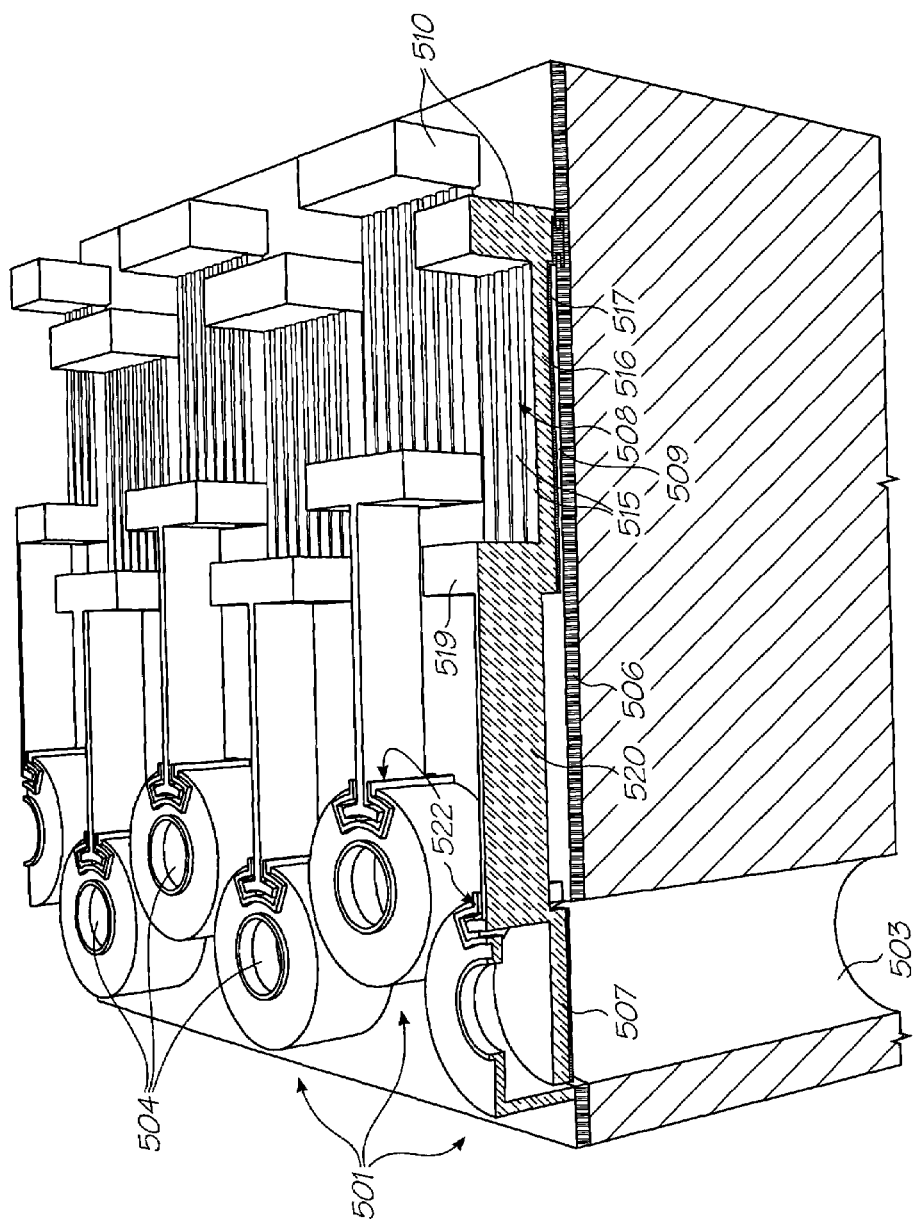
FIG. 24 shows an array of the nozzle arrangements shown in FIG. 23.
Figure 25:
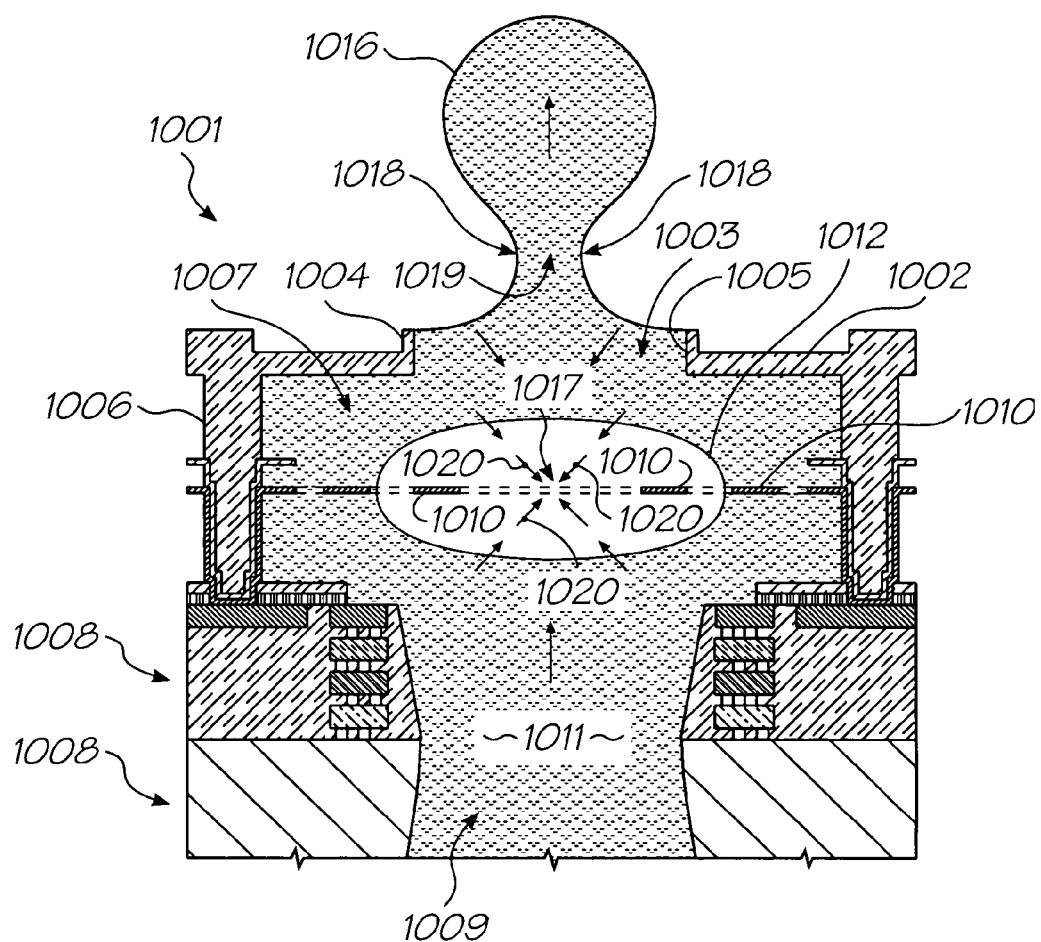
FIG. 25 is a schematic cross-sectional view through an ink chamber of a unit cell of a bubble forming heater element actuator.

FIG. 23 illustrates a side perspective view of the nozzle arrangement. FIG. 24 illustrates sectional view through an array of nozzle arrangement of FIG. 23. In these figures, the numbering of elements previously introduced has been retained.

Firstly, the actuator 508 includes a series of tapered actuator units e.g. 515 which comprise an upper glass portion (amorphous silicon dioxide) 516 formed on top of a titanium nitride layer 517. Alternatively a copper nickel alloy layer (hereinafter called cupronickel) can be utilized which will have a higher bend efficiency.

The titanium nitride layer 517 is in a tapered form and, as such, resistive heating takes place near an end portion of the post 510. Adjacent titanium nitride/glass portions 515 are interconnected at a block portion 519 which also provides a mechanical structural support for the actuator 508.

The heater means 509 ideally includes a plurality of the tapered actuator unit 515 which are elongate and spaced apart such that, upon heating, the bending force exhibited along the axis of the actuator 508 is maximized. Slots are defined between adjacent tapered units 515 and allow for slight differential operation of each actuator 508 with respect to adjacent actuators 508.

The block portion 519 is interconnected to an arm 520. The arm 520 is in turn connected to the paddle 507 inside the nozzle chamber 501 by means of a slot e.g. 522 formed in the side of the nozzle chamber 501. The slot 522 is designed generally to mate with the surfaces of the arm 520 so as to minimize opportunities for the outflow of ink around the arm 520. The ink is held generally within the nozzle chamber 501 via surface tension effects around the slot 522.

When it is desired to actuate the arm 520, a conductive current is passed through the titanium nitride layer 517 via vias within the block portion 519 connecting to a lower CMOS layer 506 which provides the necessary power and control circuitry for the nozzle arrangement. The conductive current results in heating of the nitride layer 517 adjacent to the post 510 which results in a general upward bending of the arm 20 and consequential ejection of ink out of the nozzle 504. The ejected drop is printed on a page in the usual manner for an inkjet printer as previously described.

An array of nozzle arrangements can be formed so as to create a single printhead. For example, in FIG. 24 there is illustrated a partly sectioned various array view which comprises multiple ink ejection nozzle arrangements of FIG. 23 laid out in interleaved lines so as to form a printhead array. Of course, different types of arrays can be formulated including full color arrays etc.

The construction of the printhead system described can proceed utilizing standard MEMS techniques through suitable modification of the steps as set out in U.S. Pat. No. 6,243,113 entitled "Image Creation Method and Apparatus (IJ 41)" to the present applicant, the contents of which are fully incorporated by cross reference.

Bubble Forming Heater Element Actuator

Figure 17:
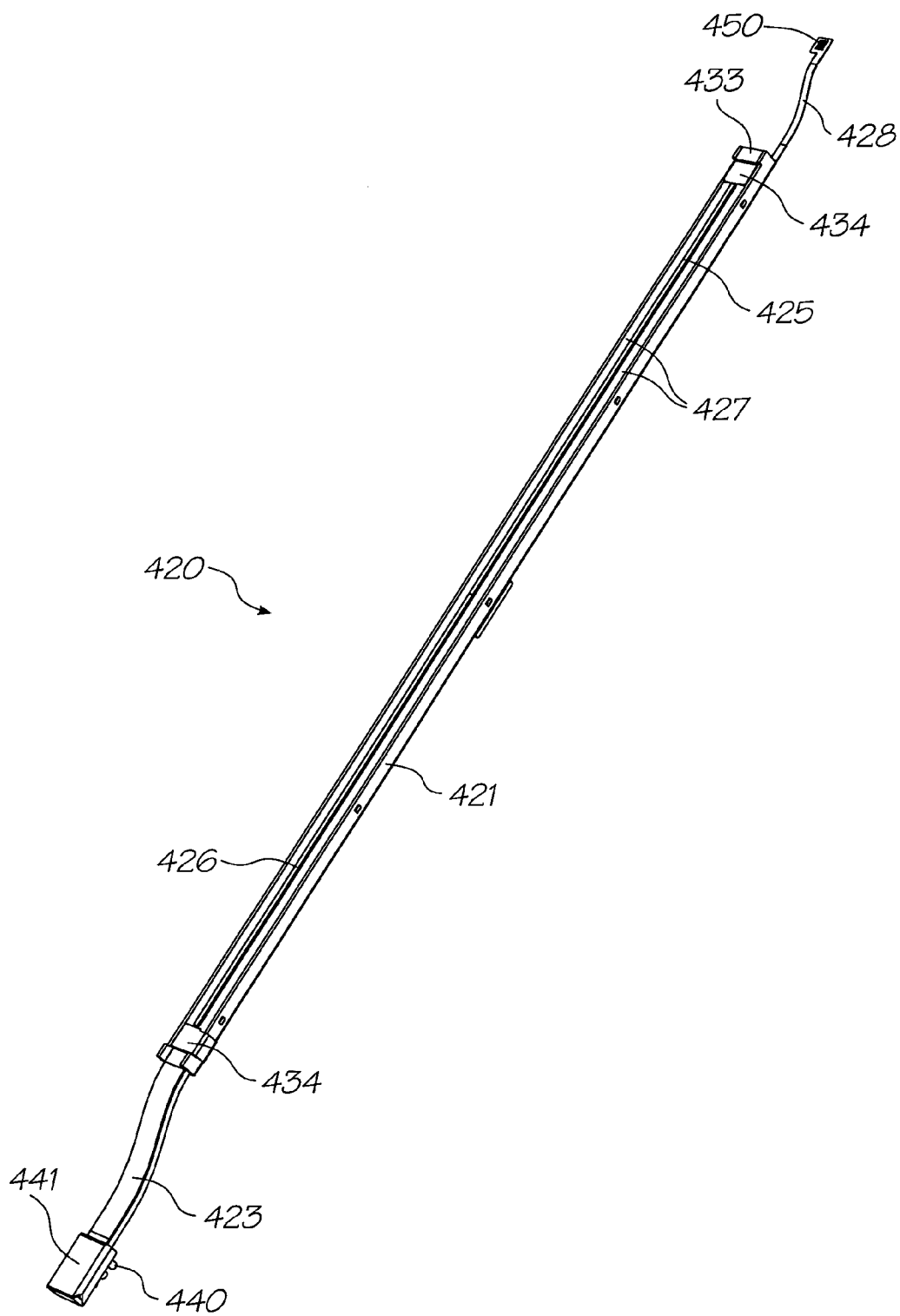
FIG. 17 is a perspective view of a bi-lithic printhead.

With reference to FIG. 17, the unit cell 1001 of a bubble forming heater element actuator comprises a nozzle plate 1002 with nozzles 1003 therein, the nozzles having nozzle rims 1004, and apertures 1005 extending through the nozzle plate. The nozzle plate 1002 is plasma etched from a silicon nitride structure which is deposited, by way of chemical vapor deposition (CVD), over a sacrificial material which is subsequently etched.

The printhead also includes, with respect to each nozzle 1003, side walls 1006 on which the nozzle plate is supported, a chamber 1007 defined by the walls and the nozzle plate 1002, a multi-layer substrate 1008 and an inlet passage 1009 extending through the multi-layer substrate to the far side (not shown) of the substrate. A looped, elongate heater element 1010 is suspended within the chamber 1007, so that the element is in the form of a suspended beam. The printhead as shown is a microelectromechanical system (MEMS) structure, which is formed by a lithographic process.

When the printhead is in use, ink 1011 from a reservoir (not shown) enters the chamber 1007 via the inlet passage 1009, so that the chamber fills. Thereafter, the heater element 1010 is heated for somewhat less than 1 micro second, so that the heating is in the form of a thermal pulse. It will be appreciated that the heater element 1010 is in thermal contact with the ink 1011 in the chamber 1007 so that when the element is heated, this causes the generation of vapor bubbles in the ink. Accordingly, the ink 1011 constitutes a bubble forming liquid.

The bubble 1012, once generated, causes an increase in pressure within the chamber 1007, which in turn causes the ejection of a drop 1016 of the ink 1011 through the nozzle

1003. The rim 1004 assists in directing the drop 1016 as it is ejected, so as to minimize the chance of a drop misdirection.

The reason that there is only one nozzle 1003 and chamber 1007 per inlet passage 1009 is so that the pressure wave generated within the chamber, on heating of the element 1010 and forming of a bubble 1012, does not effect adjacent chambers and their corresponding nozzles.

The increase in pressure within the chamber 1007 not only pushes ink 1011 out through the nozzle 1003, but also pushes some ink back through the inlet passage 1009. However, the inlet passage 1009 is approximately 200 to 300 microns in length, and is only approximately 16 microns in diameter. Hence there is a substantial viscous drag. As a result, the predominant effect of the pressure rise in the chamber 1007 is to force ink out through the nozzle 1003 as an ejected drop 1016, rather than back through the inlet passage 9.

As shown in FIG. 17, the ink drop 1016 is being ejected is shown during its "necking phase" before the drop breaks off. At this stage, the bubble 1012 has already reached its maximum size and has then begun to collapse towards the point of collapse 1017.

The collapsing of the bubble 1012 towards the point of collapse 1017 causes some ink 1011 to be drawn from within the nozzle 1003 (from the sides 1018 of the drop), and some to be drawn from the inlet passage 1009, towards the point of collapse. Most of the ink 1011 drawn in this manner is drawn from the nozzle 1003, forming an annular neck 1019 at the base of the drop 16 prior to its breaking off.

The drop 1016 requires a certain amount of momentum to overcome surface tension forces, in order to break off. As ink 1011 is drawn from the nozzle 1003 by the collapse of the bubble 1012, the diameter of the neck 1019 reduces thereby reducing the amount of total surface tension holding the drop, so that the momentum of the drop as it is ejected out of the nozzle is sufficient to allow the drop to break off.

When the drop 1016 breaks off, cavitation forces are caused as reflected by the arrows 1020, as the bubble 1012 collapses to the point of collapse 1017. It will be noted that there are no solid surfaces in the vicinity of the point of collapse 1017 on which the cavitation can have an effect.

Inkjet Cartridges

The present invention also provides an inkjet ink cartridge comprising an inkjet ink as described above. Ink cartridges for inkjet printers are well known in the art and are available in numerous forms. Preferably, the inkjet ink cartridges of the present invention are replaceable. Inkjet cartridges suitable for use in the present invention are described in the following patent applications, all of which are incorporated herein by reference in their entirety.

U.S. Pat. No. 6,428,155, Ser. No. 10/171,987

In one preferred form, the ink cartridge comprises:

a housing defining a plurality of storage areas wherein at least one of the storage areas contains colorant for printing information that is visible to the human eye and at least one of the other storage areas contains an inkjet ink as described above.

Preferably, each storage area is sized corresponding to the expected levels of use of its contents relative to the intended print coverage for a number of printed pages.

Figure 9:
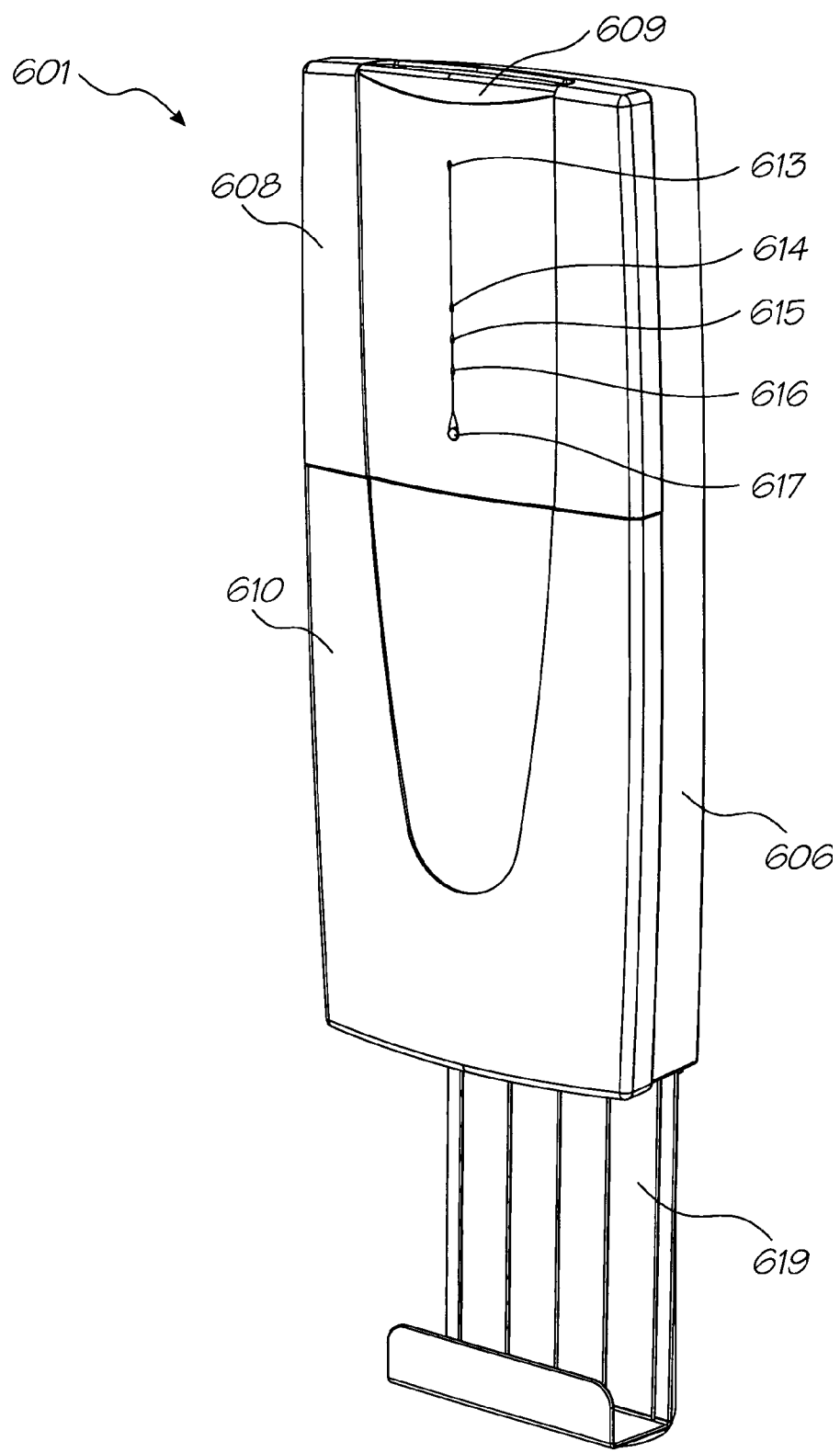
FIG. 9 is a perspective view of a wall-mounted netpage printer.
Figure 12:
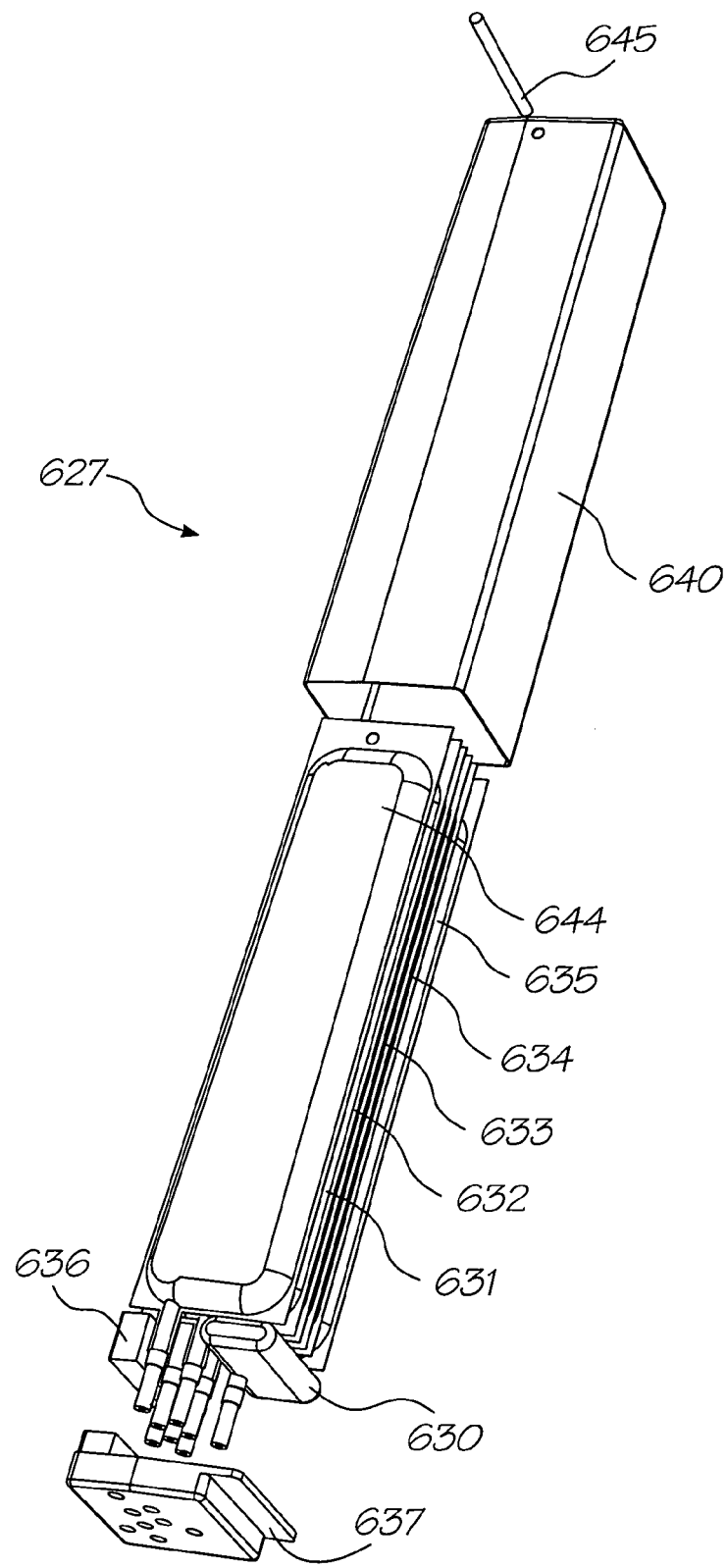
FIG. 12 is an exploded view of an ink cartridge.

There now follows a brief description of an ink cartridge according to the present invention. FIG. 12 shows the complete assembly of the replaceable ink cartridge 627. It has bladders or chambers for storing fixative 644, adhesive 630, and cyan 631, magenta 632, yellow 633, black 634 and infrared 635 inks. The cartridge 627 also contains a micro air filter 636 in a base molding 637. As shown in FIG. 9, the micro air filter 636 interfaces with an air pump 638 inside the printer via a hose 639. This provides filtered air to the printheads 705 to prevent ingress of micro particles into the Memjet™ printheads 705 which may clog the nozzles. By incorporating the air filter 636 within the cartridge 627, the operational life of the filter is effectively linked to the life of the cartridge. This ensures that the filter is replaced together with the cartridge rather than relying on the user to clean or replace the filter at the required intervals. Furthermore, the adhesive and infrared ink are replenished together with the visible inks and air filter thereby reducing how frequently the printer operation is interrupted because of the depletion of a consumable material.

The cartridge 627 has a thin wall casing 640. The ink bladders 631 to 635 and fixative bladder 644 are suspended within the casing by a pin 645 which hooks the cartridge together. The single glue bladder 630 is accommodated in the base molding 637. This is a fully recyclable product with a capacity for printing and gluing 3000 pages (1500 sheets).

Substrates

As mentioned above, the dyes of the present invention are especially suitable for use in Hyperlabel™ and netpage systems. Such systems are described in more detail below and in the patent applications listed above, all of which are incorporated herein by reference in their entirety.

Hence, the present invention provides a substrate having an IR-absorbing dye as described above disposed thereon. Preferably, the substrate comprises an interface surface. Preferably, the dye is disposed in the form of coded data suitable for use in netpage and/or Hyperlabel™ systems. For example, the coded data may be indicative of the identity of a product item. Preferably, the coded data is disposed over a substantial portion of an interface surface of the substrate (e.g. greater than 20%, greater than 50% or greater than 90% of the surface).

Preferably, the substrate is IR reflective so that the dye disposed thereon may be detected by a sensing device. The substrate may be comprised of any suitable material such as plastics (e.g. polyolefins, polyesters, polyamides etc.), paper, metal or combinations thereof.

For netpage applications, the substrate is preferably a paper sheet. For Hyperlabel™ applications, the substrate is preferably a tag, a label, a packaging material or a surface of a product item. Typically, tags and labels are comprised of plastics, paper or combinations thereof.

In accordance with Hyperlabel™ applications of the invention, the substrate may be an interactive product item adapted for interaction with a user via a sensing device and a computer system, the interactive product item comprising:

a product item having an identity;

an interface surface associated with the product item and having disposed thereon information relating to the product item and coded data indicative of the identity of the product item, wherein said coded data comprise an IR-absorbing dye as described above.

Netpage and Hyperlabel™

Netpage applications of this invention are described generally in the sixth and seventh aspects of the invention above. Hyperlabel™ applications of this invention are described generally in the eighth and ninth aspects of the invention above.

There now follows a detailed overview of netpage and Hyperlabel™. (Note: Memjet™ and Hyperlabel™ are trade marks of Silverbrook Research Pty Ltd, Australia). It will be appreciated that not every implementation will necessarily embody all or even most of the specific details and extensions discussed below in relation to the basic system. However, the system is described in its most complete form to reduce the need for external reference when attempting to understand the context in which the preferred embodiments and aspects of the present invention operate.

In brief summary, the preferred form of the netpage system employs a computer interface in the form of a mapped surface, that is, a physical surface which contains references to a map of the surface maintained in a computer system. The map references can be queried by an appropriate sensing device. Depending upon the specific implementation, the map references may be encoded visibly or invisibly, and defined in such a way that a local query on the mapped surface yields an unambiguous map reference both within the map and among different maps. The computer system can contain information about features on the mapped surface, and such information can be retrieved based on map references supplied by a sensing device used with the mapped surface. The information thus retrieved can take the form of actions which are initiated by the computer system on behalf of the operator in response to the operator's interaction with the surface features.

In its preferred form, the netpage system relies on the production of, and human interaction with, netpages. These are pages of text, graphics and images printed on ordinary paper, but which work like interactive web pages. Information is encoded on each page using ink which is substantially invisible to the unaided human eye. The ink, however, and thereby the coded data, can be sensed by an optically imaging pen and transmitted to the netpage system.

In the preferred form, active buttons and hyperlinks on each page can be clicked with the pen to request information from the network or to signal preferences to a network server. In one embodiment, text written by hand on a netpage is automatically recognized and converted to computer text in the netpage system, allowing forms to be filled in. In other embodiments, signatures recorded on a netpage are automatically verified, allowing e-commerce transactions to be securely authorized.

As illustrated in FIG. 1, a printed netpage 1 can represent an interactive form which can be filled in by the user both physically, on the printed page, and "electronically", via communication between the pen and the netpage system. The example shows a "Request" form containing name and address fields and a submit button. The netpage consists of graphic data 2 printed using visible ink, and coded data 3 printed as a collection of tags 4 using invisible ink. The corresponding page description 5, stored on the netpage network, describes the individual elements of the netpage. In particular it describes the type and spatial extent (zone) of each interactive element (i.e. text field or button in the example), to allow the netpage system to correctly interpret input via the netpage. The submit button 6, for example, has a zone 7 which corresponds to the spatial extent of the corresponding graphic 8.

Figure 2:
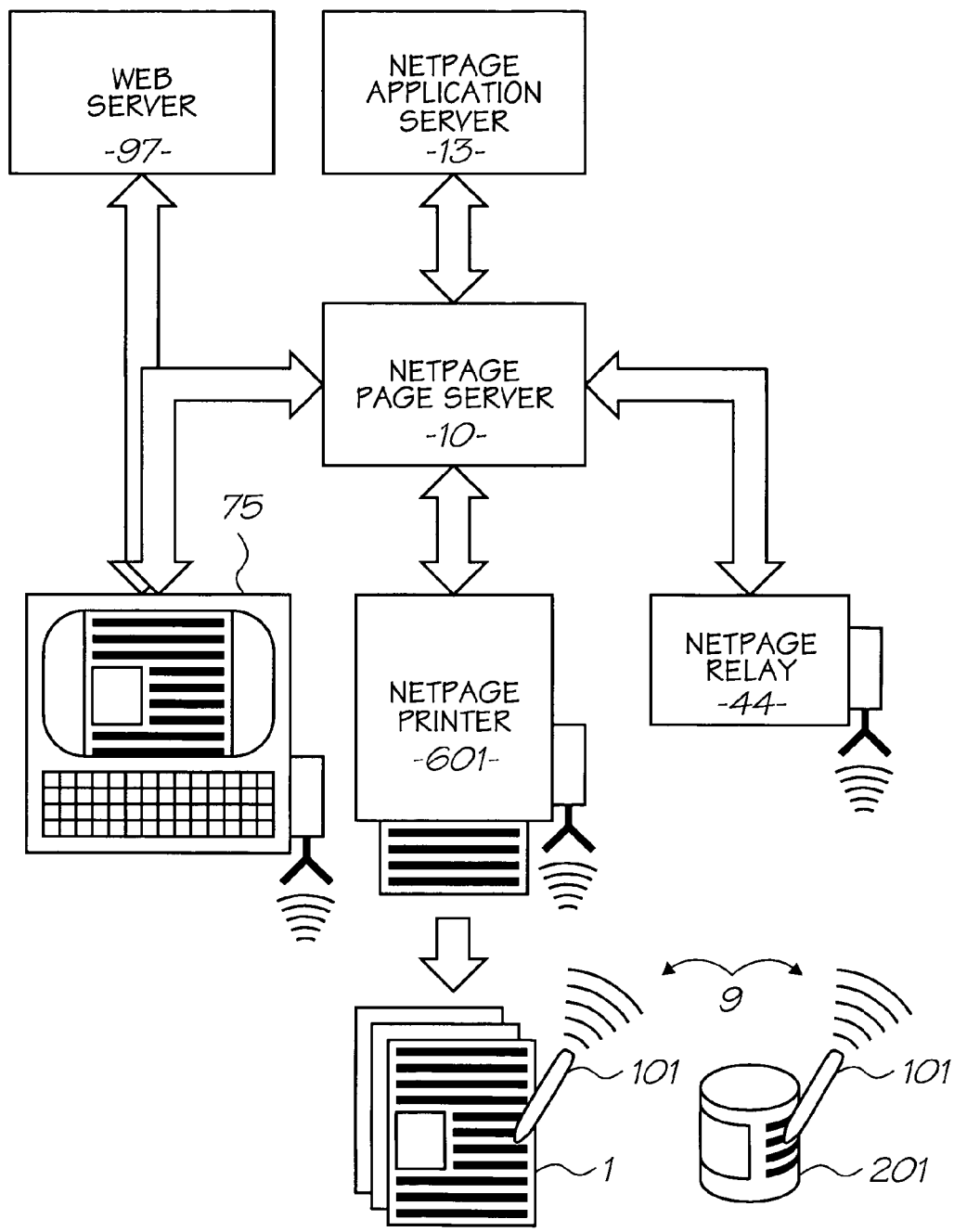
FIG. 2 is a schematic view of a interaction between a netpage pen, a Web terminal, a netpage printer, a netpage relay, a netpage page server, and a netpage application server, and a Web server.
Figure 6:
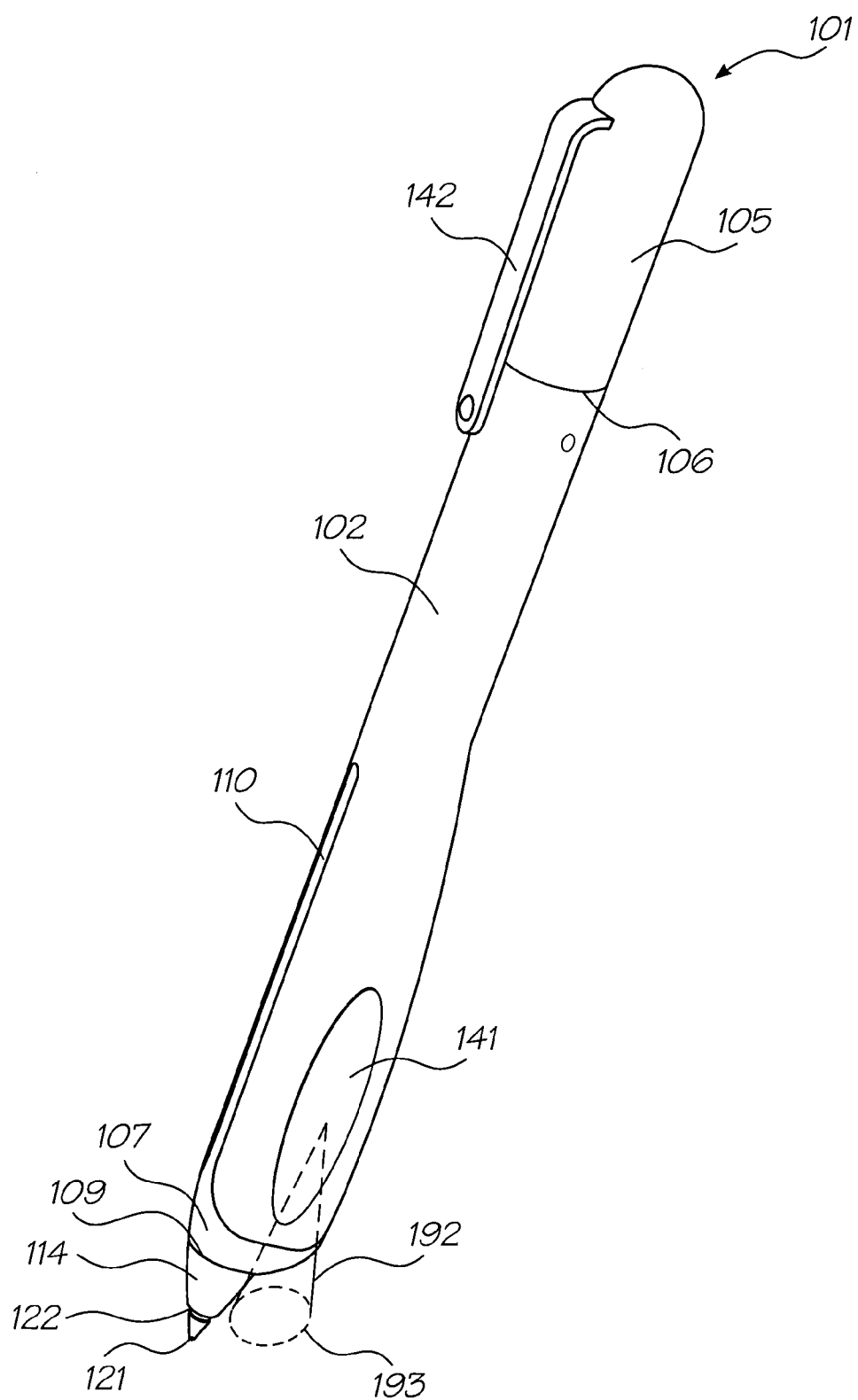
FIG. 6 is a perspective view of a netpage pen and its associated tag-sensing field-of-view cone.
Figure 7:
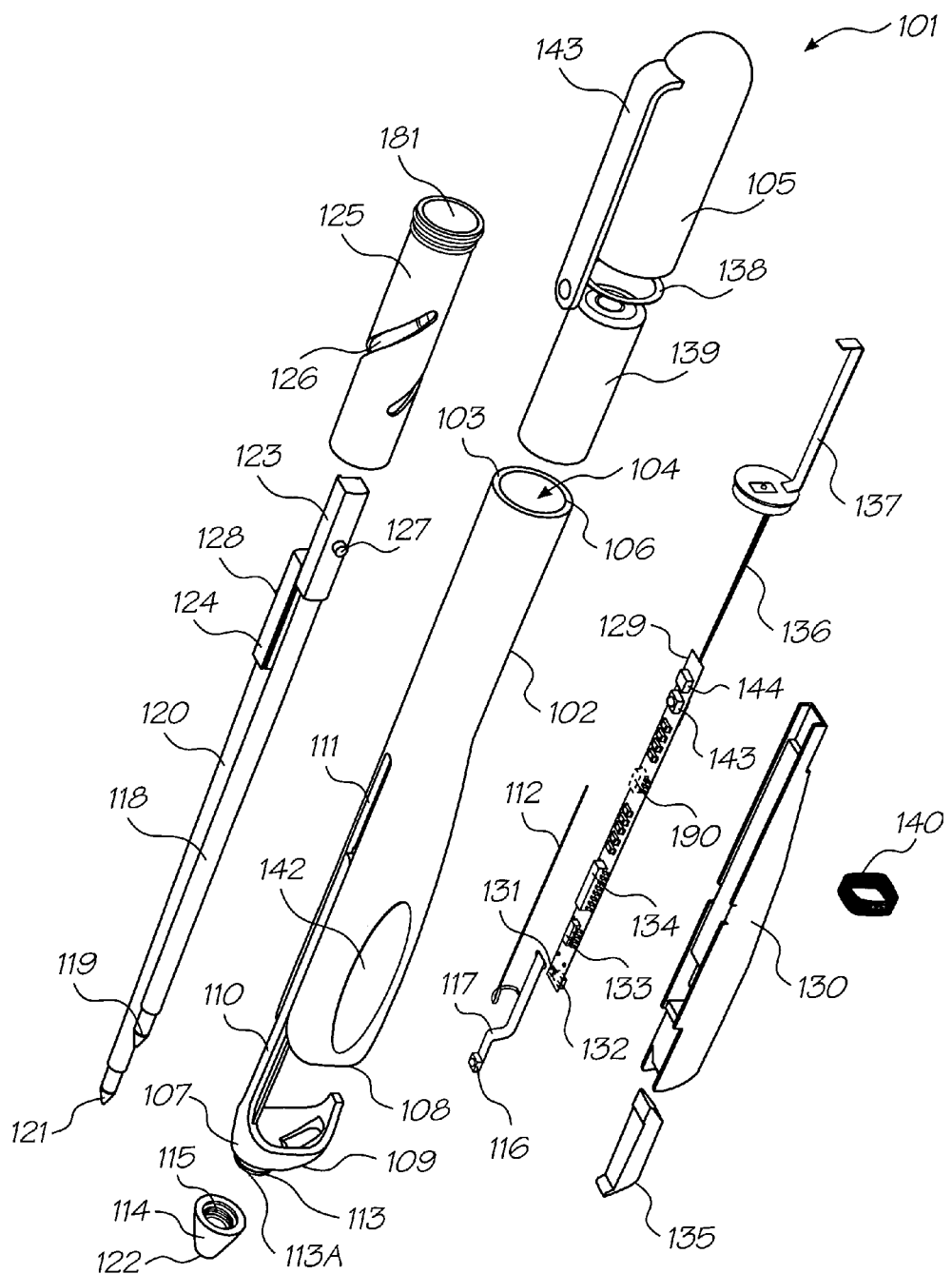
FIG. 7 is a perspective exploded view of the netpage pen shown in FIG. 6.

As illustrated in FIG. 2, the netpage pen 101, a preferred form of which is shown in FIGS. 6 and 7 and described in more detail below, works in conjunction with a personal computer (PC), Web terminal 75, or a netpage printer 601. The netpage printer is an Internet-connected printing appliance for home, office or mobile use. The pen is wireless and communicates securely with the netpage network via a short-range radio link 9. Short-range communication is relayed to the netpage network by a local relay function which is either embedded in the PC, Web terminal or netpage printer, or is provided by a separate relay device 44. The relay function can also be provided by a mobile phone or other device which incorporates both short-range and longer-range communications functions.

In an alternative embodiment, the netpage pen utilises a wired connection, such as a USB or other serial connection, to the PC, Web terminal, netpage printer or relay device.

Figure 10:
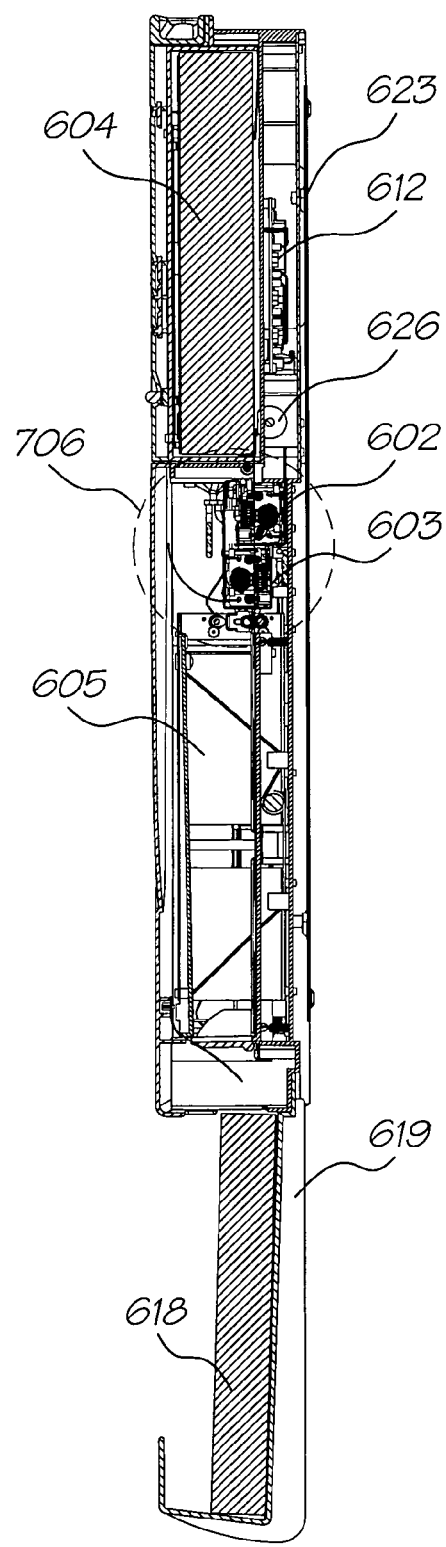
FIG. 10 is a section through the length of the netpage printer of FIG. 9.
Figure 11:
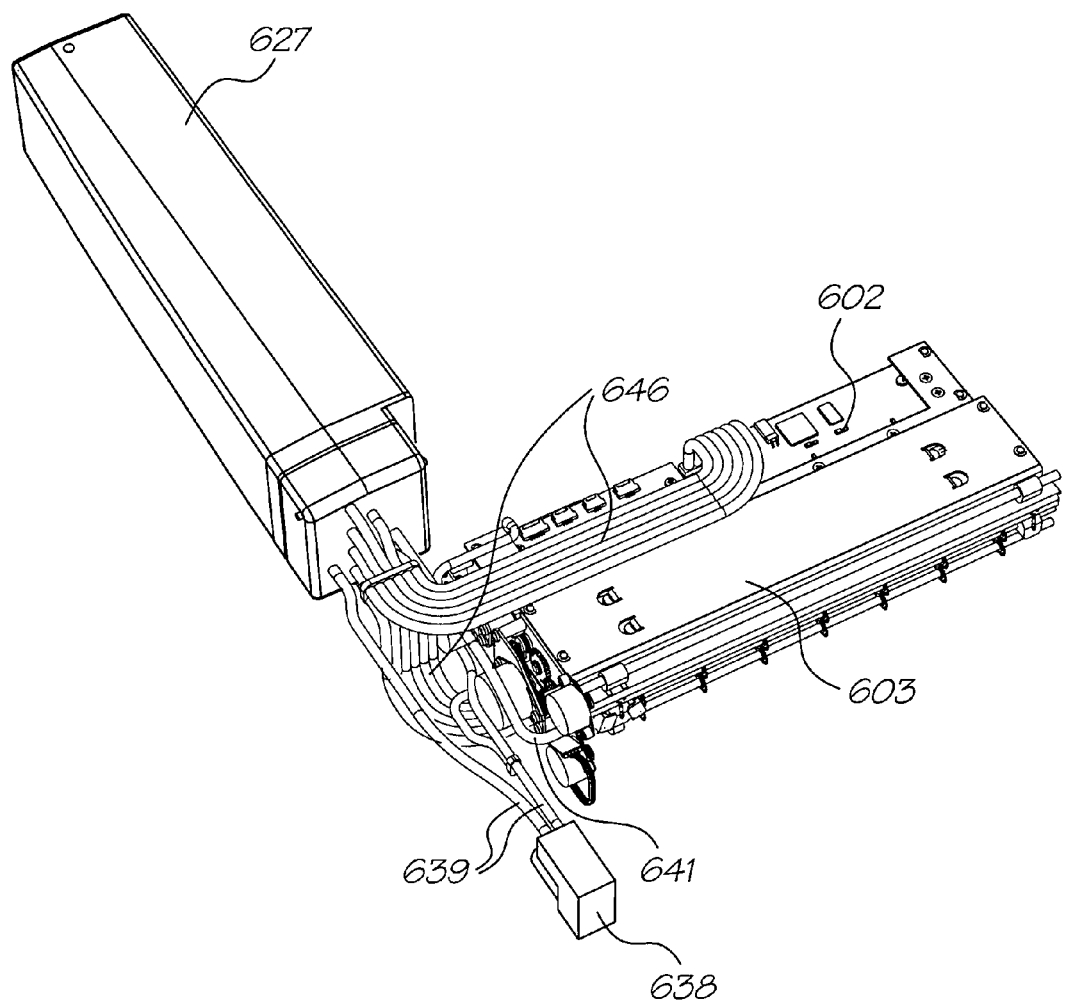
FIG. 11 is a detailed view of the ink cartridge, ink, air and glue paths, and print engines of the netpage printer of FIGS. 9 and 10.

The netpage printer 601, a preferred form of which is shown in FIGS. 9 to 11 and described in more detail below, is able to deliver, periodically or on demand, personalized newspapers, magazines, catalogs, brochures and other publications, all printed at high quality as interactive netpages. Unlike a personal computer, the netpage printer is an appliance which can be, for example, wall-mounted adjacent to an area where the morning news is first consumed, such as in a user's kitchen, near a breakfast table, or near the household's point of departure for the day. It also comes in tabletop, desktop, portable and miniature versions.

Netpages printed at their point of consumption combine the ease-of-use of paper with the timeliness and interactivity of an interactive medium.

As shown in FIG. 2, the netpage pen 101 interacts with the coded data on a printed netpage 1 (or product item 201) and communicates the interaction via a short-range radio link 9 to a relay. The relay sends the interaction to the relevant netpage page server 10 for interpretation. In appropriate circumstances, the page server sends a corresponding message to application computer software running on a netpage application server 13. The application server may in turn send a response which is printed on the originating printer.

In an alternative embodiment, the PC, Web terminal, netpage printer or relay device may communicate directly with local or remote application software, including a local or remote Web server. Relatedly, output is not limited to being printed by the netpage printer. It can also be displayed on the PC or Web terminal, and further interaction can be screen-based rather than paper-based, or a mixture of the two.

The netpage system is made considerably more convenient in the preferred embodiment by being used in conjunction with high-speed microelectromechanical system (MEMS) based inkjet (Memjet™) printers. In the preferred form of this technology, relatively high-speed and high-quality printing is made more affordable to consumers. In its preferred form, a netpage publication has the physical characteristics of a traditional news-magazine, such as a set of letter-size glossy pages printed in full color on both sides, bound together for easy navigation and comfortable handling.

The netpage printer exploits the growing availability of broadband Internet access. Cable service is available to 95% of households in the United States, and cable modem service offering broadband Internet access is already available to 20% of these. The netpage printer can also operate with slower connections, but with longer delivery times and lower image quality. Indeed, the netpage system can be enabled using existing consumer inkjet and laser printers, although the system will operate more slowly and will therefore be less acceptable from a consumer's point of view. In other embodiments, the netpage system is hosted on a private intranet. In still other embodiments, the netpage system is hosted on a single computer or computer-enabled device, such as a printer.

Netpage publication servers 14 on the netpage network are configured to deliver print-quality publications to netpage printers. Periodical publications are delivered automatically to subscribing netpage printers via pointcasting and multicasting Internet protocols. Personalized publications are filtered and formatted according to individual user profiles.

A netpage printer can be configured to support any number of pens, and a pen can work with any number of netpage printers. In the preferred implementation, each netpage pen has a unique identifier. A household may have a collection of colored netpage pens, one assigned to each member of the family. This allows each user to maintain a distinct profile with respect to a netpage publication server or application server.

A netpage pen can also be registered with a netpage registration server 11 and linked to one or more payment card accounts. This allows e-commerce payments to be securely authorized using the netpage pen. The netpage registration server compares the signature captured by the netpage pen with a previously registered signature, allowing it to authenticate the user's identity to an e-commerce server. Other biometrics can also be used to verify identity. A version of the netpage pen includes fingerprint scanning, verified in a similar way by the netpage registration server.

Although a netpage printer may deliver periodicals such as the morning newspaper without user intervention, it can be configured never to deliver unsolicited junk mail. In its preferred form, it only delivers periodicals from subscribed or otherwise authorized sources. In this respect, the netpage printer is unlike a fax machine or e-mail account which is visible to any junk mailer who knows the telephone number or email address.

1 Netpage System Architecture

Each object model in the system is described using a Unified Modeling Language (UML) class diagram. A class diagram consists of a set of object classes connected by relationships, and two kinds of relationships are of interest here: associations and generalizations. An association represents some kind of relationship between objects, i.e. between instances of classes. A generalization relates actual classes, and can be understood in the following way: if a class is thought of as the set of all objects of that class, and class A is a generalization of class B, then B is simply a subset of A. The UML does not directly support second-order modelling—i.e. classes of classes.

Each class is drawn as a rectangle labelled with the name of the class. It contains a list of the attributes of the class, separated from the name by a horizontal line, and a list of the operations of the class, separated from the attribute list by a horizontal line. In the class diagrams which follow, however, operations are never modelled.

An association is drawn as a line joining two classes, optionally labelled at either end with the multiplicity of the association. The default multiplicity is one. An asterisk (*) indicates a multiplicity of "many", i.e. zero or more. Each association is optionally labelled with its name, and is also optionally labelled at either end with the role of the corresponding class. An open diamond indicates an aggregation association ("is-part-of"), and is drawn at the aggregator end of the association line.

A generalization relationship ("is-a") is drawn as a solid line joining two classes, with an arrow (in the form of an open triangle) at the generalization end.

When a class diagram is broken up into multiple diagrams, any class which is duplicated is shown with a dashed outline in all but the main diagram which defines it. It is shown with attributes only where it is defined.

1.1 Netpages

Netpages are the foundation on which a netpage network is built. They provide a paper-based user interface to published information and interactive services.

A netpage consists of a printed page (or other surface region) invisibly tagged with references to an online description of the page. The online page description is maintained persistently by a netpage page server. The page description describes the visible layout and content of the page, including text, graphics and images. It also describes the input elements on the page, including buttons, hyperlinks, and input fields. A netpage allows markings made with a netpage pen on its surface to be simultaneously captured and processed by the netpage system.

Multiple netpages can share the same page description. However, to allow input through otherwise identical pages to be distinguished, each netpage is assigned a unique page identifier. This page ID has sufficient precision to distinguish between a very large number of netpages.

Each reference to the page description is encoded in a printed tag. The tag identifies the unique page on which it appears, and thereby indirectly identifies the page description. The tag also identifies its own position on the page. Characteristics of the tags are described in more detail below.

Tags are printed in infrared-absorptive ink on any substrate which is infrared-reflective, such as ordinary paper. Near-infrared wavelengths are invisible to the human eye but are easily sensed by a solid-state image sensor with an appropriate filter.

A tag is sensed by an area image sensor in the netpage pen, and the tag data is transmitted to the netpage system via the nearest netpage printer. The pen is wireless and communicates with the netpage printer via a short-range radio link. Tags are sufficiently small and densely arranged that the pen can reliably image at least one tag even on a single click on the page. It is important that the pen recognize the page ID and position on every interaction with the page, since the interaction is stateless. Tags are error-correctably encoded to make them partially tolerant to surface damage.

The netpage page server maintains a unique page instance for each printed netpage, allowing it to maintain a distinct set of user-supplied values for input fields in the page description for each printed netpage.

Figure 4:
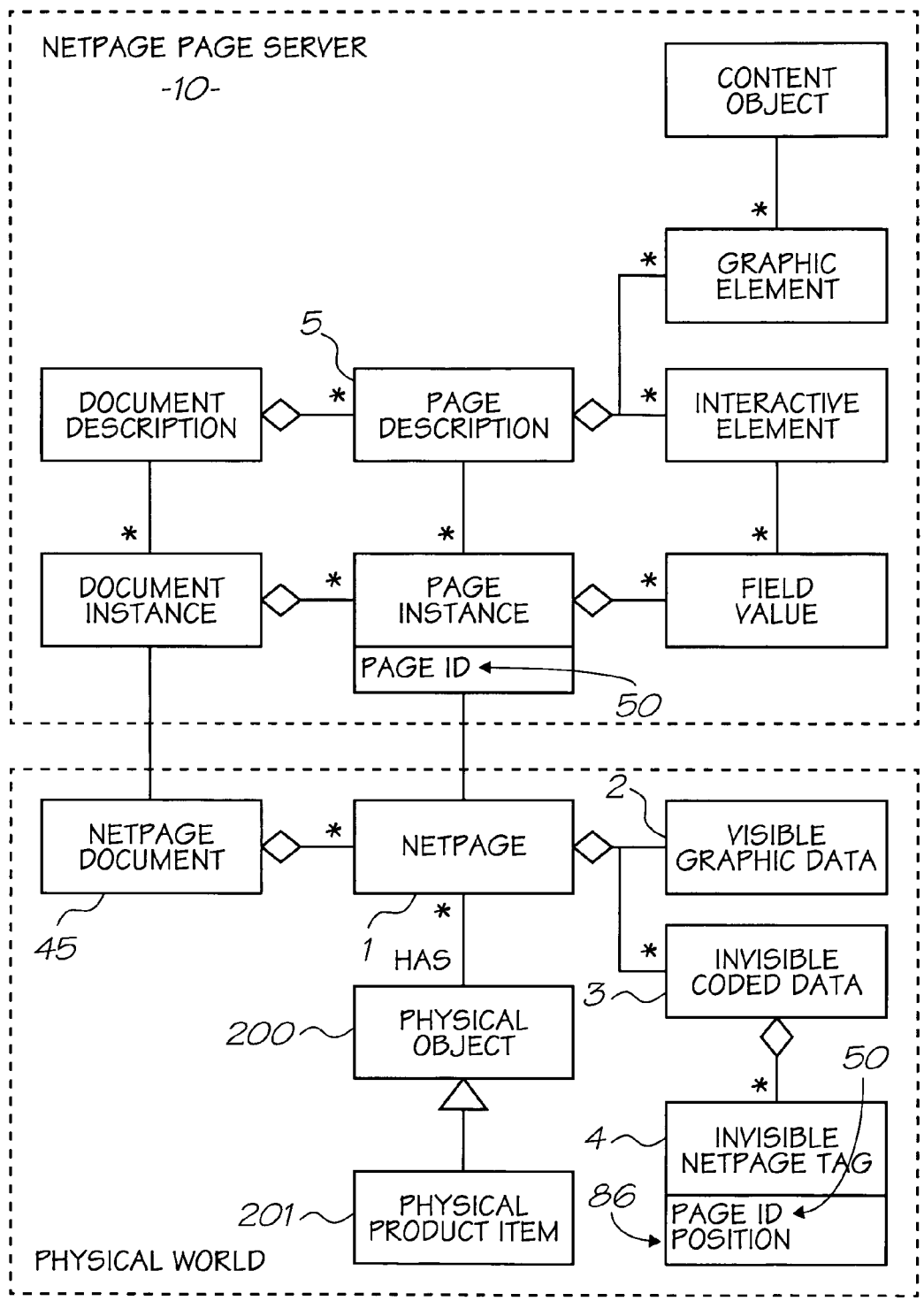
FIG. 4 is a schematic view of a high-level structure of a printed netpage and its online page description.

The relationship between the page description, the page instance, and the printed netpage is shown in FIG. 4. The printed netpage may be part of a printed netpage document 45. The page instance is associated with both the netpage printer which printed it and, if known, the netpage user who requested it.

As shown in FIG. 4, one or more netpages may also be associated with a physical object such as a product item, for example when printed onto the product item's label, packaging, or actual surface.

1.2 Netpage Tags 1.2.1 Tag Data Content

In a preferred form, each tag identifies the region in which it appears, and the location of that tag within the region. A tag may also contain flags which relate to the region as a whole or to the tag. One or more flag bits may, for example, signal a tag sensing device to provide feedback indicative of a function associated with the immediate area of the tag, without the sensing device having to refer to a description of the region. A netpage pen may, for example, illuminate an "active area" LED when in the zone of a hyperlink.

As will be more clearly explained below, in a preferred embodiment, each tag contains an easily recognized invariant structure which aids initial detection, and which assists in minimizing the effect of any warp induced by the surface or by the sensing process. The tags preferably tile the entire page, and are sufficiently small and densely arranged that the pen can reliably image at least one tag even on a single click on the page. It is important that the pen recognize the page ID and position on every interaction with the page, since the interaction is stateless.

In a preferred embodiment, the region to which a tag refers coincides with an entire page, and the region ID encoded in the tag is therefore synonymous with the page ID of the page on which the tag appears. In other embodiments, the region to which a tag refers can be an arbitrary subregion of a page or other surface. For example, it can coincide with the zone of an interactive element, in which case the region ID can directly identify the interactive element.

In the preferred form, each tag contains 120 bits of information. The region ID is typically allocated up to 100 bits, the tag ID at least 16 bits, and the remaining bits are allocated to flags etc. Assuming a tag density of 64 per square inch, a 16-bit tag ID supports a region size of up to 1024 square inches. Larger regions can be mapped continuously without increasing the tag ID precision simply by using abutting regions and maps. The 100-bit region ID allows $2^{100}$ (~$10^{30}$ or a million trillion trillion) different regions to be uniquely identified.

1.2.2 Tag Data Encoding

In one embodiment, the 120 bits of tag data are redundantly encoded using a (15, 5) Reed-Solomon code. This yields 360 encoded bits consisting of 6 codewords of 15 4-bit symbols each. The (15, 5) code allows up to 5 symbol errors to be corrected per codeword, i.e. it is tolerant of a symbol error rate of up to 33% per codeword.

Each 4-bit symbol is represented in a spatially coherent way in the tag, and the symbols of the six codewords are interleaved spatially within the tag. This ensures that a burst error (an error affecting multiple spatially adjacent bits) damages a minimum number of symbols overall and a minimum number of symbols in any one codeword, thus maximising the likelihood that the burst error can be fully corrected.

Any suitable error-correcting code code can be used in place of a (15, 5) Reed-Solomon code, for example: a Reed-Solomon code with more or less redundancy, with the same or different symbol and codeword sizes; another block code; or a different kind of code, such as a convolutional code (see, for example, Stephen B. Wicker, Error Control Systems for Digital Communication and Storage, Prentice-Hall 1995, the contents of which a herein incorporated by reference thereto).

In order to support "single-click" interaction with a tagged region via a sensing device, the sensing device must be able to see at least one entire tag in its field of view no matter where in the region or at what orientation it is positioned. The required diameter of the field of view of the sensing device is therefore a function of the size and spacing of the tags.

1.2.3 Tag Structure

Figure 5A:
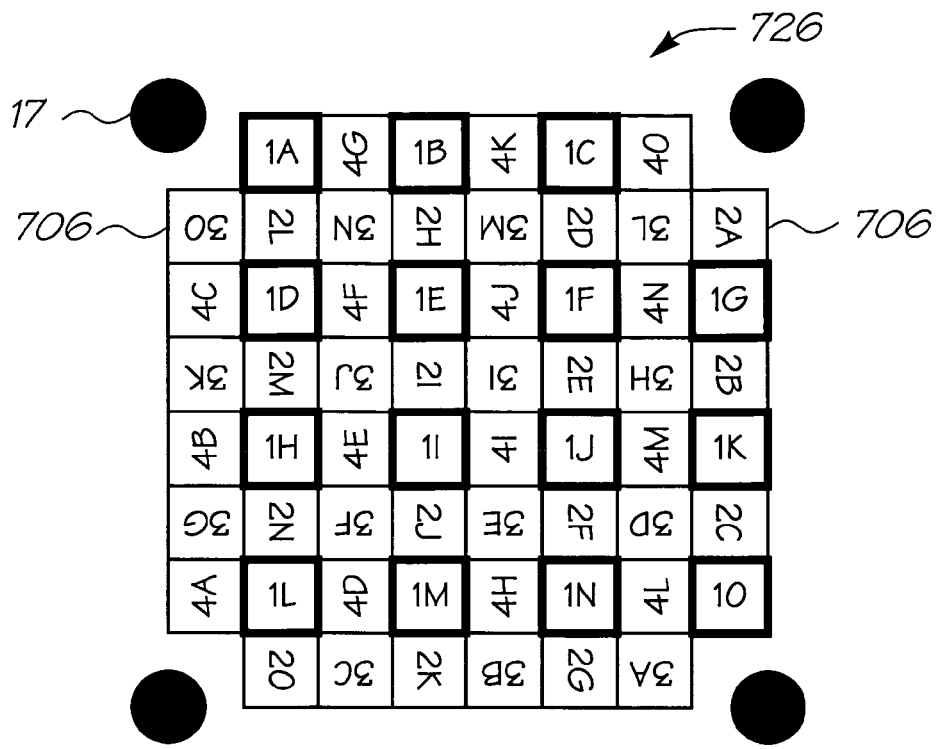
FIG. 5a is a plan view showing the interleaving and rotation of the symbols of four codewords of the tag.
Figure 5B:
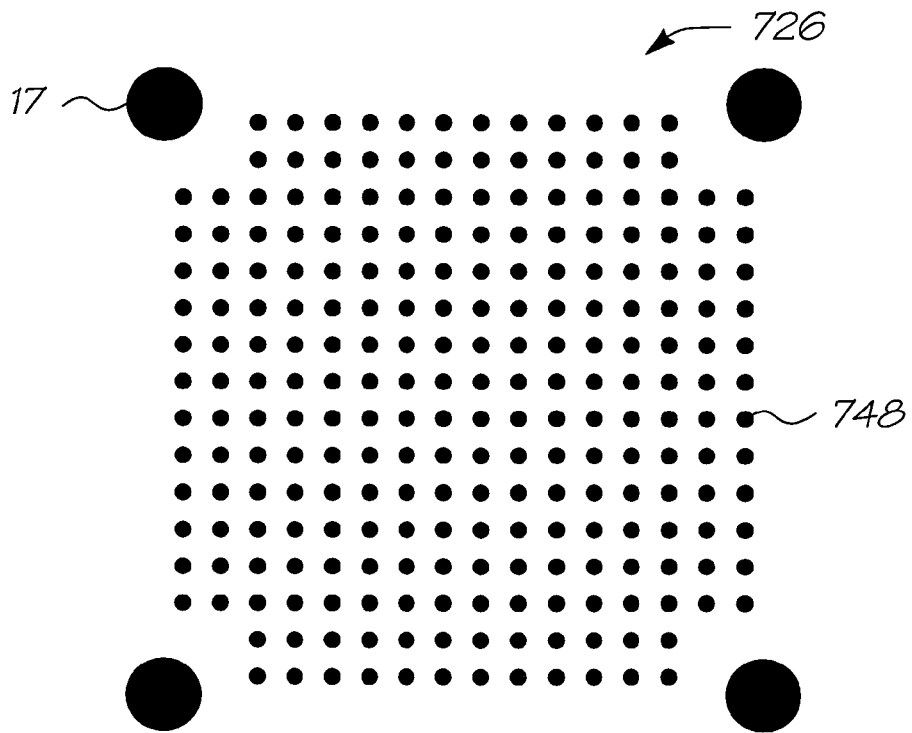
Figure 5C:
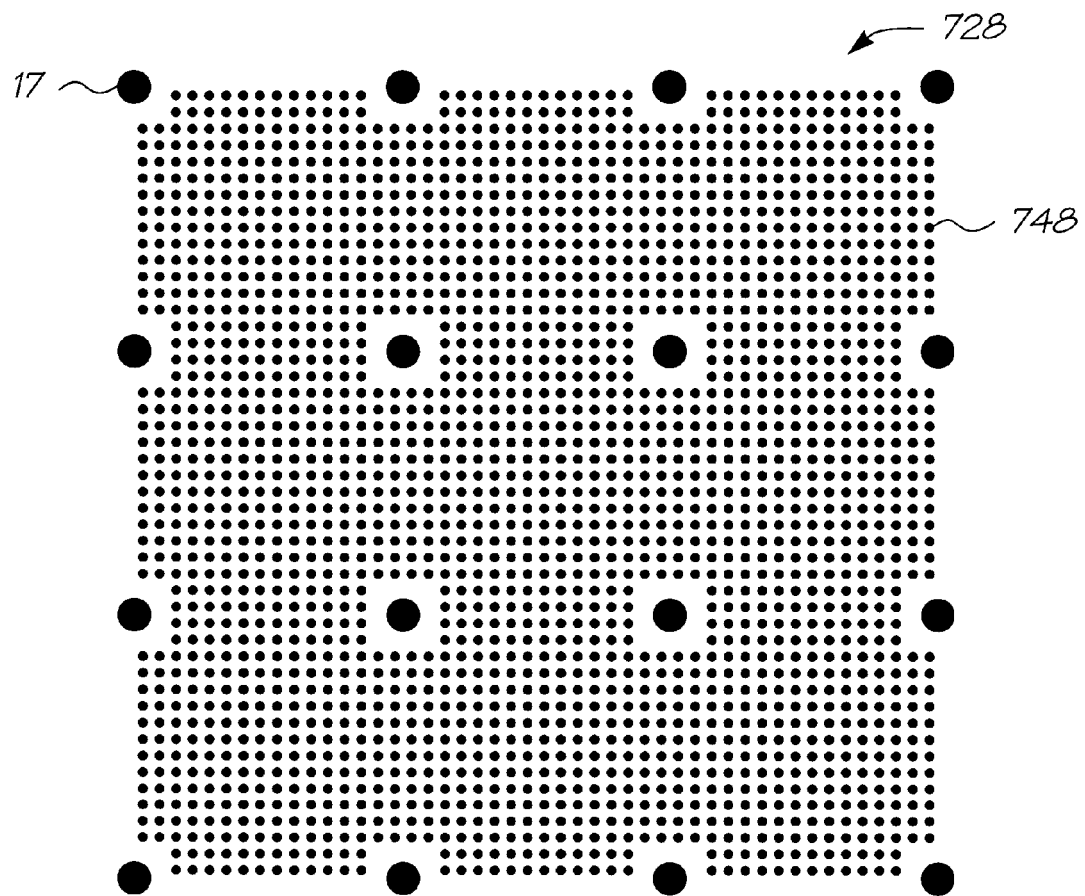
FIG. 5c is a plan view showing an arrangement of nine of the tags shown in FIGS. 5a and 5b, in which targets are shared between adjacent tags.
Figure 5D:
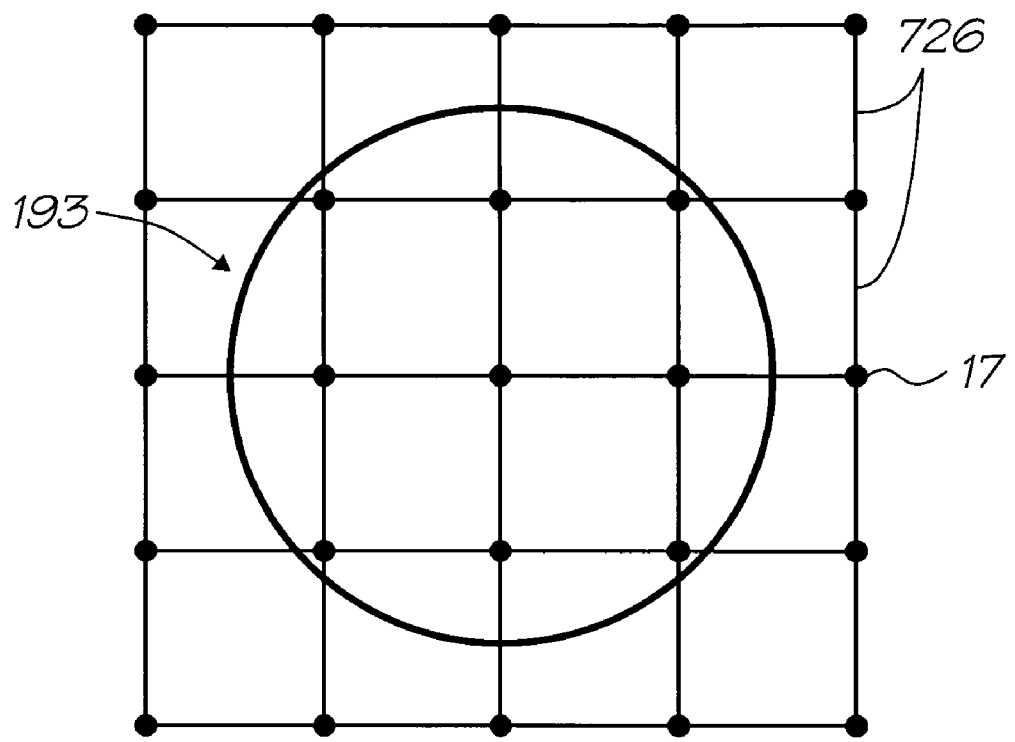
FIG. 5d is a plan view showing a relationship between a set of the tags shown in FIG. 5a and a field of view of a netpage sensing device in the form of a netpage pen.

FIG. 5a shows a tag 4, in the form of tag 726 with four perspective targets 17. The tag 726 represents sixty 4-bit Reed-Solomon symbols 747, for a total of 240 bits. The tag represents each "one" bit by the presence of a mark 748, referred to as a macrodot, and each "zero" bit by the absence of the corresponding macrodot. FIG. 5c shows a square tiling 728 of nine tags, containing all "one" bits for illustrative purposes. It will be noted that the perspective targets are designed to be shared between adjacent tags. FIG. 5d shows a square tiling of 16 tags and a corresponding minimum field of view 193, which spans the diagonals of two tags.

Using a (15, 7) Reed-Solomon code, 112 bits of tag data are redundantly encoded to produce 240 encoded bits. The four codewords are interleaved spatially within the tag to maximize resilience to burst errors. Assuming a 16-bit tag ID as before, this allows a region ID of up to 92 bits.

The data-bearing macrodots 748 of the tag are designed to not overlap their neighbors, so that groups of tags cannot produce structures that resemble targets. This also saves ink. The perspective targets allow detection of the tag, so further targets are not required.

Although the tag may contain an orientation feature to allow disambiguation of the four possible orientations of the tag relative to the sensor, the present invention is concerned with embedding orientation data in the tag data. For example, the four codewords can be arranged so that each tag orientation (in a rotational sense) contains one codeword placed at that orientation, as shown in FIG. 5a, where each symbol is labelled with the number of its codeword (1-4) and the position of the symbol within the codeword (A-O). Tag decoding then consists of decoding one codeword at each rotational orientation. Each codeword can either contain a single bit indicating whether it is the first codeword, or two bits indicating which codeword it is. The latter approach has the advantage that if, say, the data content of only one codeword is required, then at most two codewords need to be decoded to obtain the desired data. This may be the case if the region ID is not expected to change within a stroke and is thus only decoded at the start of a stroke. Within a stroke only the codeword containing the tag ID is then desired. Furthermore, since the rotation of the sensing device changes slowly and predictably within a stroke, only one codeword typically needs to be decoded per frame.

It is possible to dispense with perspective targets altogether and instead rely on the data representation being self-registering. In this case each bit value (or multi-bit value) is typically represented by an explicit glyph, i.e. no bit value is represented by the absence of a glyph. This ensures that the data grid is well-populated, and thus allows the grid to be reliably identified and its perspective distortion detected and subsequently corrected during data sampling. To allow tag boundaries to be detected, each tag data must contain a marker pattern, and these must be redundantly encoded to allow reliable detection. The overhead of such marker patterns is similar to the overhead of explicit perspective targets. Various such schemes are described in the present applicants' co-pending PCT application PCT/AU01/01274 filed 11 Oct. 2001.

The arrangement 728 of FIG. 5c shows that the square tag 726 can be used to fully tile or tesselate, i.e. without gaps or overlap, a plane of arbitrary size.

Although in preferred embodiments the tagging schemes described herein encode a single data bit using the presence or absence of a single undifferentiated macrodot, they can also use sets of differentiated glyphs to represent single-bit or multi-bit values, such as the sets of glyphs illustrated in the present applicants' co-pending PCT application PCT/AU01/01274 filed 11 Oct. 2001.

1.3 The Netpage Network

Figure 3:
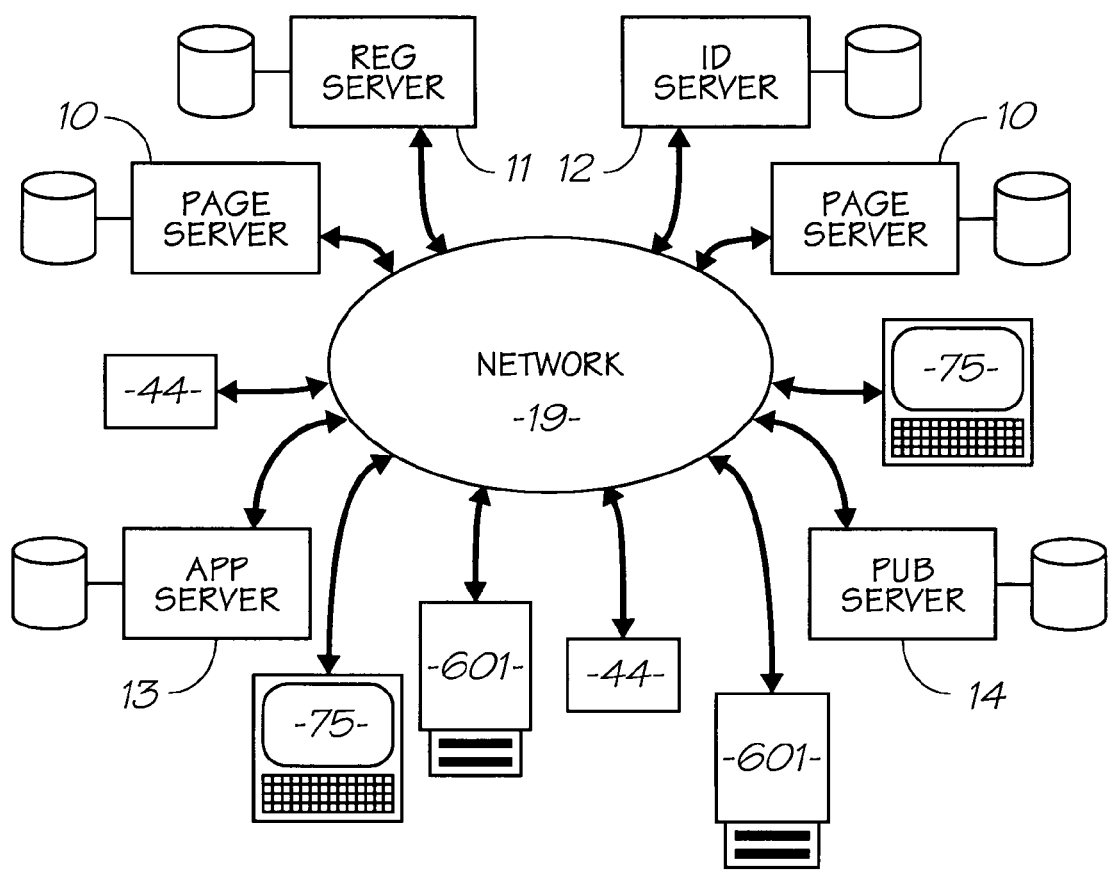
FIG. 3 illustrates a collection of netpage servers, Web terminals, printers and relays interconnected via a network.

In a preferred embodiment, a netpage network consists of a distributed set of netpage page servers 10, netpage registration servers 11, netpage ID servers 12, netpage application servers 13, netpage publication servers 14, Web terminals 75, netpage printers 601, and relay devices 44 connected via a network 19 such as the Internet, as shown in FIG. 3.

The netpage registration server 11 is a server which records relationships between users, pens, printers, applications and publications, and thereby authorizes various network activities. It authenticates users and acts as a signing proxy on behalf of authenticated users in application transactions. It also provides handwriting recognition services. As described above, a netpage page server 10 maintains persistent information about page descriptions and page instances. The netpage network includes any number of page servers, each handling a subset of page instances. Since a page server also maintains user input values for each page instance, clients such as netpage printers send netpage input directly to the appropriate page server. The page server interprets any such input relative to the description of the corresponding page.

A netpage ID server 12 allocates document IDs 51 on demand, and provides load-balancing of page servers via its ID allocation scheme.

A netpage printer uses the Internet Distributed Name System (DNS), or similar, to resolve a netpage page ID 50 into the network address of the netpage page server handling the corresponding page instance.

A netpage application server 13 is a server which hosts interactive netpage applications. A netpage publication server 14 is an application server which publishes netpage documents to netpage printers.

Netpage servers can be hosted on a variety of network server platforms from manufacturers such as IBM, Hewlett-Packard, and Sun. Multiple netpage servers can run concurrently on a single host, and a single server can be distributed over a number of hosts. Some or all of the functionality provided by netpage servers, and in particular the functionality provided by the ID server and the page server, can also be provided directly in a netpage appliance such as a netpage printer, in a computer workstation, or on a local network.

1.4 The Netpage Printer

The netpage printer 601 is an appliance which is registered with the netpage system and prints netpage documents on demand and via subscription. Each printer has a unique printer ID 62, and is connected to the netpage network via a network such as the Internet, ideally via a broadband connection.

Apart from identity and security settings in non-volatile memory, the netpage printer contains no persistent storage. As far as a user is concerned, "the network is the computer". Netpages function interactively across space and time with the help of the distributed netpage page servers 10, independently of particular netpage printers.

The netpage printer receives subscribed netpage documents from netpage publication servers 14. Each document is distributed in two parts: the page layouts, and the actual text and image objects which populate the pages. Because of personalization, page layouts are typically specific to a particular subscriber and so are pointcast to the subscriber's printer via the appropriate page server. Text and image objects, on the other hand, are typically shared with other subscribers, and so are multicast to all subscribers' printers and the appropriate page servers.

The netpage publication server optimizes the segmentation of document content into pointcasts and multicasts. After receiving the pointcast of a document's page layouts, the printer knows which multicasts, if any, to listen to.

Once the printer has received the complete page layouts and objects that define the document to be printed, it can print the document.

The printer rasterizes and prints odd and even pages simultaneously on both sides of the sheet. It contains duplexed print engine controllers 760 and print engines utilizing Memjet™ printheads 350 for this purpose.

The printing process consists of two decoupled stages: rasterization of page descriptions, and expansion and printing of page images. The raster image processor (RIP) consists of one or more standard DSPs 757 running in parallel. The duplexed print engine controllers consist of custom processors which expand, dither and print page images in real time, synchronized with the operation of the printheads in the print engines.

Printers not enabled for IR printing have the option to print tags using IR-absorptive black ink, although this restricts tags to otherwise empty areas of the page. Although such pages have more limited functionality than IR-printed pages, they are still classed as netpages.

A normal netpage printer prints netpages on sheets of paper. More specialised netpage printers may print onto more specialised surfaces, such as globes. Each printer supports at least one surface type, and supports at least one tag tiling scheme, and hence tag map, for each surface type. The tag map 811 which describes the tag tiling scheme actually used to print a document becomes associated with that document so that the document's tags can be correctly interpreted.

FIG. 2 shows the netpage printer class diagram, reflecting printer-related information maintained by a registration server 11 on the netpage network.

1.5 The Netpage Pen

The active sensing device of the netpage system is typically a pen 101, which, using its embedded controller 134, is able to capture and decode IR position tags from a page via an image sensor. The image sensor is a solid-state device provided with an appropriate filter to permit sensing at only near-infrared wavelengths. As described in more detail below, the system is able to sense when the nib is in contact with the surface, and the pen is able to sense tags at a sufficient rate to capture human handwriting (i.e. at 200 dpi or greater and 100 Hz or faster). Information captured by the pen is encrypted and wirelessly transmitted to the printer (or base station), the printer or base station interpreting the data with respect to the (known) page structure.

Figure 14:
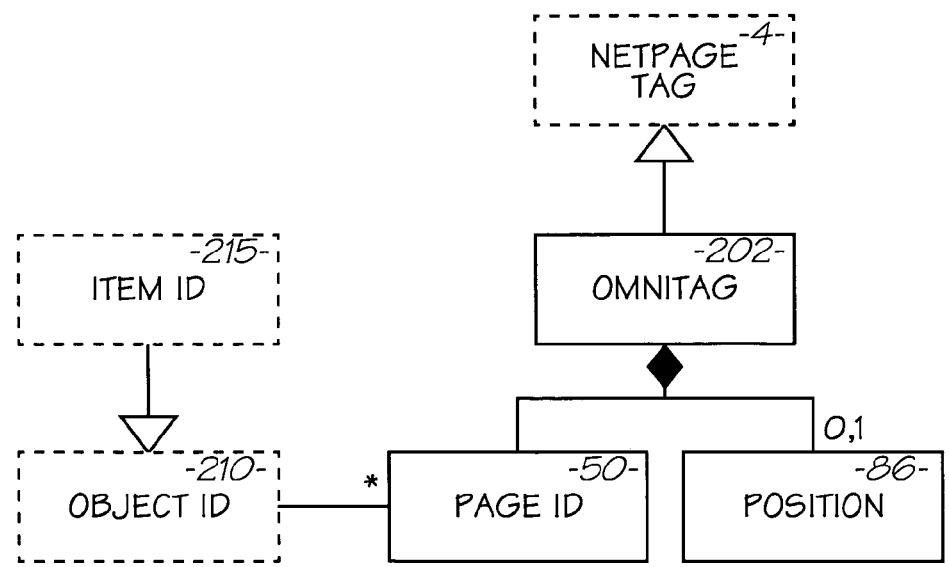
FIG. 14 is a schematic view of the structure of an omnitag.
Figure 15:
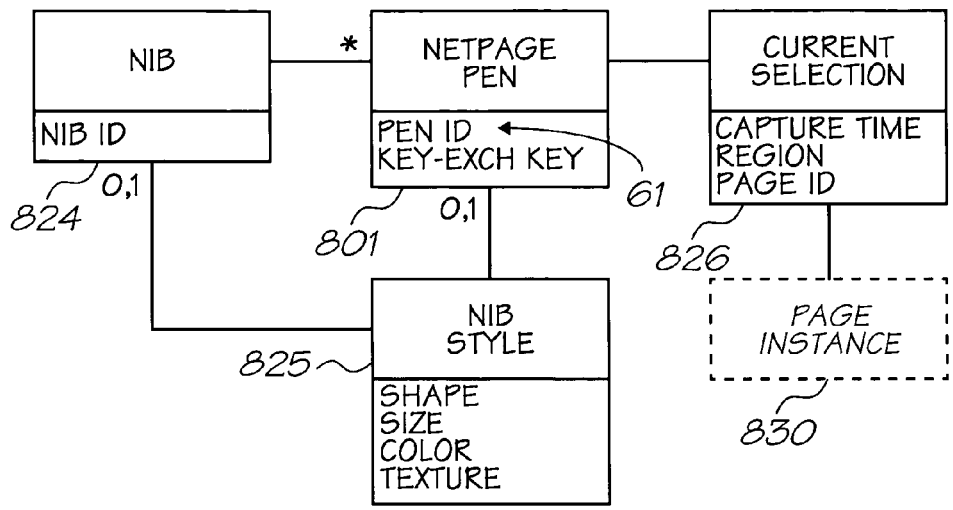
FIG. 15 is a schematic view of a pen class diagram.

The preferred embodiment of the netpage pen operates both as a normal marking ink pen and as a non-marking stylus. The marking aspect, however, is not necessary for using the netpage system as a browsing system, such as when it is used as an Internet interface. Each netpage pen is registered with the netpage system and has a unique pen ID 61. FIG. 14 shows the netpage pen class diagram, reflecting pen-related information maintained by a registration server 11 on the netpage network.

When either nib is in contact with a netpage, the pen determines its position and orientation relative to the page. The nib is attached to a force sensor, and the force on the nib is interpreted relative to a threshold to indicate whether the pen is "up" or "down". This allows a interactive element on the page to be 'clicked' by pressing with the pen nib, in order to request, say, information from a network. Furthermore, the force is captured as a continuous value to allow, say, the full dynamics of a signature to be verified.

The pen determines the position and orientation of its nib on the netpage by imaging, in the infrared spectrum, an area 193 of the page in the vicinity of the nib. It decodes the nearest tag and computes the position of the nib relative to the tag from the observed perspective distortion on the imaged tag and the known geometry of the pen optics. Although the position resolution of the tag may be low, because the tag density on the page is inversely proportional to the tag size, the adjusted position resolution is quite high, exceeding the minimum resolution required for accurate handwriting recognition.

Pen actions relative to a netpage are captured as a series of strokes. A stroke consists of a sequence of time-stamped pen positions on the page, initiated by a pen-down event and completed by the subsequent pen-up event. A stroke is also tagged with the page ID 50 of the netpage whenever the page ID changes, which, under normal circumstances, is at the commencement of the stroke.

Each netpage pen has a current selection 826 associated with it, allowing the user to perform copy and paste operations etc. The selection is timestamped to allow the system to discard it after a defined time period. The current selection describes a region of a page instance. It consists of the most recent digital ink stroke captured through the pen relative to the background area of the page. It is interpreted in an application-specific manner once it is submitted to an application via a selection hyperlink activation.

Each pen has a current nib 824. This is the nib last notified by the pen to the system. In the case of the default netpage pen described above, either the marking black ink nib or the non-marking stylus nib is current. Each pen also has a current nib style 825. This is the nib style last associated with the pen by an application, e.g. in response to the user selecting a color from a palette. The default nib style is the nib style associated with the current nib. Strokes captured through a pen are tagged with the current nib style. When the strokes are subsequently reproduced, they are reproduced in the nib style with which they are tagged.

Whenever the pen is within range of a printer with which it can communicate, the pen slowly flashes its "online" LED. When the pen fails to decode a stroke relative to the page, it momentarily activates its "error" LED. When the pen succeeds in decoding a stroke relative to the page, it momentarily activates its "ok" LED.

A sequence of captured strokes is referred to as digital ink. Digital ink forms the basis for the digital exchange of drawings and handwriting, for online recognition of handwriting, and for online verification of signatures.

The pen is wireless and transmits digital ink to the netpage printer via a short-range radio link. The transmitted digital ink is encrypted for privacy and security and packetized for efficient transmission, but is always flushed on a pen-up event to ensure timely handling in the printer.

When the pen is out-of-range of a printer it buffers digital ink in internal memory, which has a capacity of over ten minutes of continuous handwriting. When the pen is once again within range of a printer, it transfers any buffered digital ink.

A pen can be registered with any number of printers, but because all state data resides in netpages both on paper and on the network, it is largely immaterial which printer a pen is communicating with at any particular time.

Figure 8:
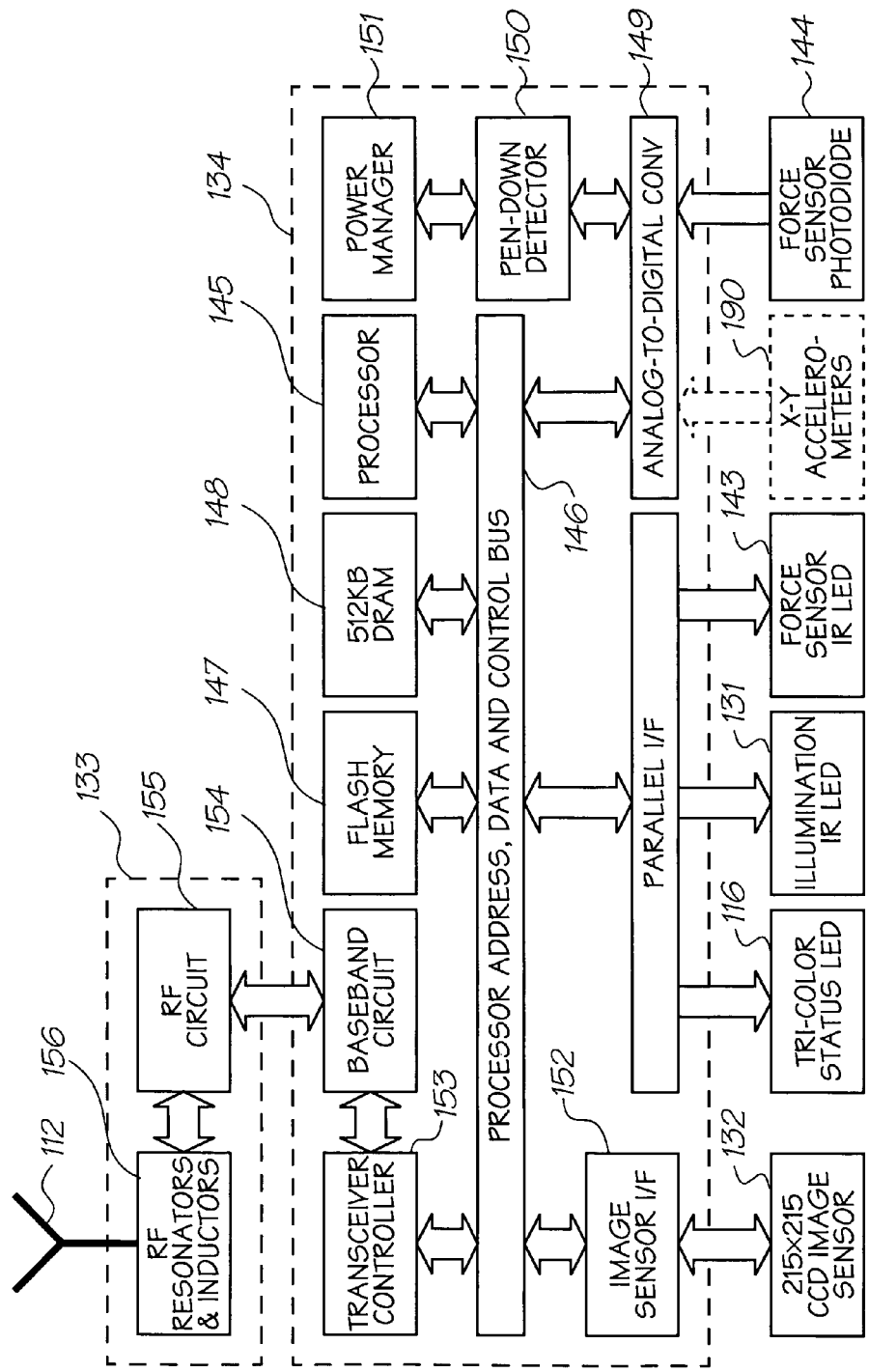
FIG. 8 is a schematic block diagram of a pen controller for the netpage pen shown in FIGS. 6 and 7.

A preferred embodiment of the pen is described in greater detail below, with reference to FIGS. 6 to 8.

1.6 Netpage Interaction

The netpage printer 601 receives data relating to a stroke from the pen 101 when the pen is used to interact with a netpage 1. The coded data 3 of the tags 4 is read by the pen when it is used to execute a movement, such as a stroke. The data allows the identity of the particular page and associated interactive element to be determined and an indication of the relative positioning of the pen relative to the page to be obtained. The indicating data is transmitted to the printer, where it resolves, via the DNS, the page ID 50 of the stroke into the network address of the netpage page server 10 which maintains the corresponding page instance 830. It then transmits the stroke to the page server. If the page was recently identified in an earlier stroke, then the printer may already have the address of the relevant page server in its cache. Each netpage consists of a compact page layout maintained persistently by a netpage page server (see below). The page layout refers to objects such as images, fonts and pieces of text, typically stored elsewhere on the netpage network.

When the page server receives the stroke from the pen, it retrieves the page description to which the stroke applies, and determines which element of the page description the stroke intersects. It is then able to interpret the stroke in the context of the type of the relevant element.

A "click" is a stroke where the distance and time between the pen down position and the subsequent pen up position are both less than some small maximum. An object which is activated by a click typically requires a click to be activated, and accordingly, a longer stroke is ignored. The failure of a pen action, such as a "sloppy" click, to register is indicated by the lack of response from the pen's "ok" LED.

There are two kinds of input elements in a netpage page description: hyperlinks and form fields. Input through a form field can also trigger the activation of an associated hyperlink.

2 Netpage Pen Description 2.1 Pen Mechanics

Referring to FIGS. 6 and 7, the pen, generally designated by reference numeral 101, includes a housing 102 in the form of a plastics moulding having walls 103 defining an interior space 104 for mounting the pen components. The pen top 105 is in operation rotatably mounted at one end 106 of the housing 102. A semi-transparent cover 107 is secured to the opposite end 108 of the housing 102. The cover 107 is also of moulded plastics, and is formed from semi-transparent material in order to enable the user to view the status of the LED mounted within the housing 102. The cover 107 includes a main part 109 which substantially surrounds the end 108 of the housing 102 and a projecting portion 110 which projects back from the main part 109 and fits within a corresponding slot 111 formed in the walls 103 of the housing 102. A radio antenna 112 is mounted behind the projecting portion 110, within the housing 102. Screw threads 113 surrounding an aperture 113A on the cover 107 are arranged to receive a metal end piece 114, including corresponding screw threads 115. The metal end piece 114 is removable to enable ink cartridge replacement.

Also mounted within the cover 107 is a tri-color status LED 116 on a flex PCB 117. The antenna 112 is also mounted on the flex PCB 117. The status LED 116 is mounted at the top of the pen 101 for good all-around visibility.

The pen can operate both as a normal marking ink pen and as a non-marking stylus. An ink pen cartridge 118 with nib 119 and a stylus 120 with stylus nib 121 are mounted side by side within the housing 102. Either the ink cartridge nib 119 or the stylus nib 121 can be brought forward through open end 122 of the metal end piece 114, by rotation of the pen top 105. Respective slider blocks 123 and 124 are mounted to the ink cartridge 118 and stylus 120, respectively. A rotatable cam barrel 125 is secured to the pen top 105 in operation and arranged to rotate therewith. The cam barrel 125 includes a cam 126 in the form of a slot within the walls 181 of the cam barrel. Cam followers 127 and 128 projecting from slider blocks 123 and 124 fit within the cam slot 126. On rotation of the cam barrel 125, the slider blocks 123 or 124 move relative to each other to project either the pen nib 119 or stylus nib 121 out through the hole 122 in the metal end piece 114. The pen 101 has three states of operation. By turning the top 105 through 90° steps, the three states are:

stylus 120 nib 121 out ink cartridge 118 nib 119 out, and neither ink cartridge 118 nib 119 out nor stylus 120 nib 121 out A second flex PCB 129, is mounted on an electronics chassis 130 which sits within the housing 102. The second flex PCB 129 mounts an infrared LED 131 for providing infrared radiation for projection onto the surface. An image sensor 132 is provided mounted on the second flex PCB 129 for receiving reflected radiation from the surface. The second flex PCB 129 also mounts a radio frequency chip 133, which includes an RF transmitter and RF receiver, and a controller chip 134 for controlling operation of the pen 101. An optics block 135 (formed from moulded clear plastics) sits within the cover 107 and projects an infrared beam onto the surface and receives images onto the image sensor 132. Power supply wires 136 connect the components on the second flex PCB 129 to battery contacts 137 which are mounted within the cam barrel 125. A terminal 138 connects to the battery contacts 137 and the cam barrel 125. A three volt rechargeable battery 139 sits within the cam barrel 125 in contact with the battery contacts. An induction charging coil 140 is mounted about the second flex PCB 129 to enable recharging of the battery 139 via induction. The second flex PCB 129 also mounts an infrared LED 143 and infrared photodiode 144 for detecting displacement in the cam barrel 125 when either the stylus 120 or the ink cartridge 118 is used for writing, in order to enable a determination of the force being applied to the surface by the pen nib 119 or stylus nib 121. The IR photodiode 144 detects light from the IR LED 143 via reflectors (not shown) mounted on the slider blocks 123 and 124.

Rubber grip pads 141 and 142 are provided towards the end 108 of the housing 102 to assist gripping the pen 101, and top 105 also includes a clip 142 for clipping the pen 101 to a pocket.

3.2 Pen Controller

The pen 101 is arranged to determine the position of its nib (stylus nib 121 or ink cartridge nib 119) by imaging, in the infrared spectrum, an area of the surface in the vicinity of the nib. It records the location data from the nearest location tag, and is arranged to calculate the distance of the nib 121 or 119 from the location tab utilising optics 135 and controller chip 134. The controller chip 134 calculates the orientation of the pen and the nib-to-tag distance from the perspective distortion observed on the imaged tag.

Utilising the RF chip 133 and antenna 112 the pen 101 can transmit the digital ink (which is encrypted for security and packaged for efficient transmission) to the computing system.

When the pen is in range of a receiver, the digital ink data is transmitted as it is formed. When the pen 101 moves out of range, digital ink data is buffered within the pen 101 (the pen 101 circuitry includes a buffer arranged to store digital ink data for approximately 12 minutes of the pen motion on the surface) and can be transmitted later.

The controller chip 134 is mounted on the second flex PCB 129 in the pen 101. FIG. 8 is a block diagram illustrating in more detail the architecture of the controller chip 134. FIG. 8 also shows representations of the RF chip 133, the image sensor 132, the tri-color status LED 116, the IR illumination LED 131, the IR force sensor LED 143, and the force sensor photodiode 144.

The pen controller chip 134 includes a controlling processor 145. Bus 146 enables the exchange of data between components of the controller chip 134. Flash memory 147 and a 512 KB DRAM 148 are also included. An analog-to-digital converter 149 is arranged to convert the analog signal from the force sensor photodiode 144 to a digital signal.

An image sensor interface 152 interfaces with the image sensor 132. A transceiver controller 153 and base band circuit 154 are also included to interface with the RF chip 133 which includes an RF circuit 155 and RF resonators and inductors 156 connected to the antenna 112.

The controlling processor 145 captures and decodes location data from tags from the surface via the image sensor 132, monitors the force sensor photodiode 144, controls the LEDs 116, 131 and 143, and handles short-range radio communication via the radio transceiver 153. It is a medium-performance (~40 MHz) general-purpose RISC processor.

The processor 145, digital transceiver components (transceiver controller 153 and baseband circuit 154), image sensor interface 152, flash memory 147 and 512 KB DRAM 148 are integrated in a single controller ASIC. Analog RF components (RF circuit 155 and RF resonators and inductors 156) are provided in the separate RF chip.

The image sensor is a CCD or CMOS image sensor. Depending on tagging scheme, it has a size ranging from about 100×100 pixels to 200×200 pixels. Many miniature CMOS image sensors are commercially available, including the National Semiconductor LM9630.

The controller ASIC 134 enters a quiescent state after a period of inactivity when the pen 101 is not in contact with a surface. It incorporates a dedicated circuit 150 which monitors the force sensor photodiode 144 and wakes up the controller 134 via the power manager 151 on a pen-down event.

The radio transceiver communicates in the unlicensed 900 MHz band normally used by cordless telephones, or alternatively in the unlicensed 2.4 GHz industrial, scientific and medical (ISM) band, and uses frequency hopping and collision detection to provide interference-free communication.

In an alternative embodiment, the pen incorporates an Infrared Data Association (IrDA) interface for short-range communication with a base station or netpage printer.

In a further embodiment, the pen 101 includes a pair of orthogonal accelerometers mounted in the normal plane of the pen 101 axis. The accelerometers 190 are shown in FIGS. 7 and 8 in ghost outline.

The provision of the accelerometers enables this embodiment of the pen 101 to sense motion without reference to surface location tags, allowing the location tags to be sampled at a lower rate. Each location tag ID can then identify an object of interest rather than a position on the surface. For example, if the object is a user interface input element (e.g. a command button), then the tag ID of each location tag within the area of the input element can directly identify the input element.

The acceleration measured by the accelerometers in each of the x and y directions is integrated with respect to time to produce an instantaneous velocity and position.

Since the starting position of the stroke is not known, only relative positions within a stroke are calculated. Although position integration accumulates errors in the sensed acceleration, accelerometers typically have high resolution, and the time duration of a stroke, over which errors accumulate, is short.

3 Netpage Printer Description 3.1 Printer Mechanics

Figure 10A:
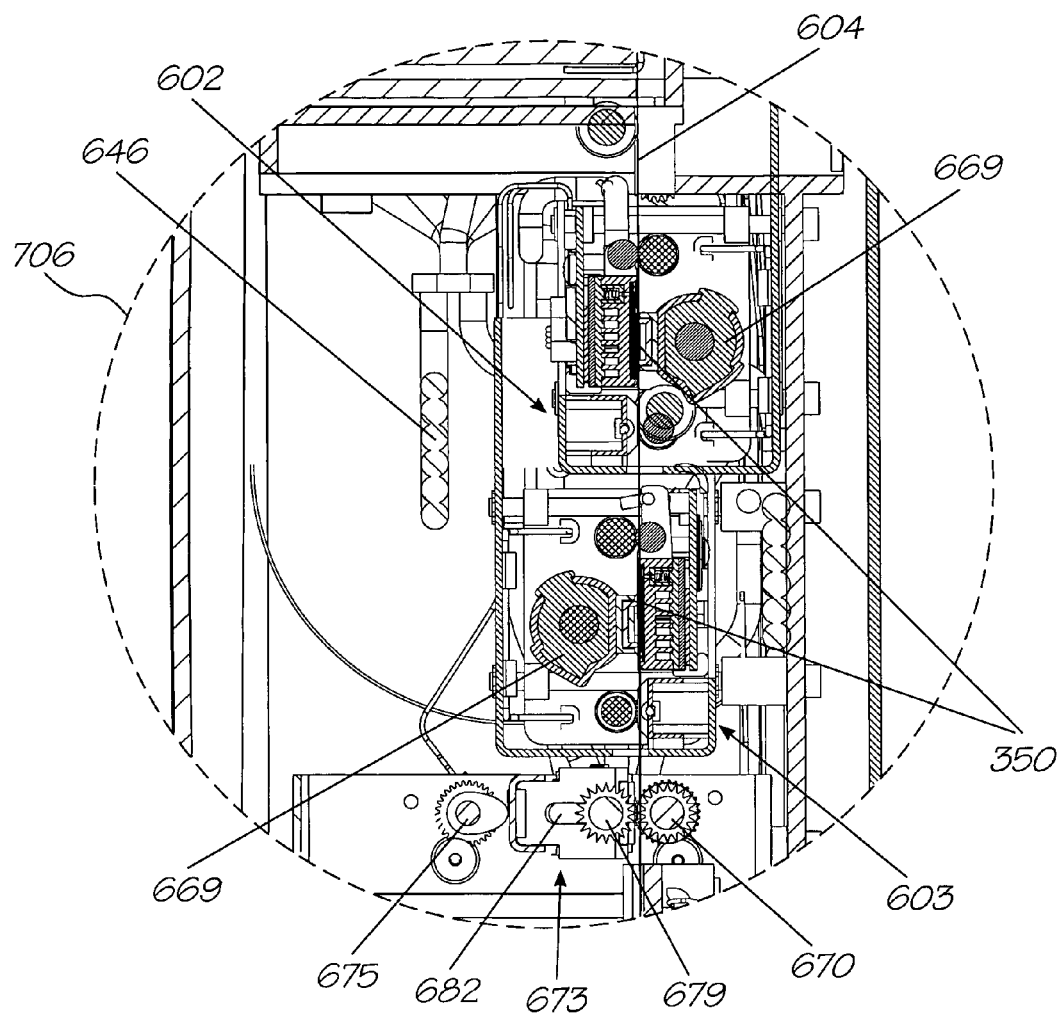
FIG. 10a is an enlarged portion of FIG. 10 showing a section of the duplexed print engines and glue wheel assembly.

The vertically-mounted netpage wallprinter 601 is shown fully assembled in FIG. 9. It prints netpages on Letter/A4 sized media using duplexed 8½" Memjet™ print engines 602 and 603, as shown in FIGS. 10 and 10a. It uses a straight paper path with the paper 604 passing through the duplexed print engines 602 and 603 which print both sides of a sheet simultaneously, in full color and with full bleed.

An integral binding assembly 605 applies a strip of glue along one edge of each printed sheet, allowing it to adhere to the previous sheet when pressed against it. This creates a final bound document 618 which can range in thickness from one sheet to several hundred sheets.

The replaceable ink cartridge 627, shown in FIG. 12 coupled with the duplexed print engines, has bladders or chambers for storing fixative, adhesive, and cyan, magenta, yellow, black and infrared inks. The cartridge also contains a micro air filter in a base molding. The micro air filter interfaces with an air pump 638 inside the printer via a hose 639. This provides filtered air to the printheads to prevent ingress of micro particles into the Memjet™ printheads 350 which might otherwise clog the printhead nozzles. By incorporating the air filter within the cartridge, the operational life of the filter is effectively linked to the life of the cartridge. The ink cartridge is a fully recyclable product with a capacity for printing and gluing 3000 pages (1500 sheets).

Referring to FIG. 10, the motorized media pick-up roller assembly 626 pushes the top sheet directly from the media tray past a paper sensor on the first print engine 602 into the duplexed Memjet™ printhead assembly. The two Memjet™ print engines 602 and 603 are mounted in an opposing in-line sequential configuration along the straight paper path. The paper 604 is drawn into the first print engine 602 by integral, powered pick-up rollers 626. The position and size of the paper 604 is sensed and full bleed printing commences. Fixative is printed simultaneously to aid drying in the shortest possible time.

The paper exits the first Memjet™ print engine 602 through a set of powered exit spike wheels (aligned along the straight paper path), which act against a rubberized roller. These spike wheels contact the 'wet' printed surface and continue to feed the sheet 604 into the second Memjet™ print engine 603.

Referring to FIGS. 10 and 10a, the paper 604 passes from the duplexed print engines 602 and 603 into the binder assembly 605. The printed page passes between a powered spike wheel axle 670 with a fibrous support roller and another movable axle with spike wheels and a momentary action glue wheel. The movable axle/glue assembly 673 is mounted to a metal support bracket and it is transported forward to interface with the powered axle 670 via gears by action of a camshaft. A separate motor powers this camshaft.

The glue wheel assembly 673 consists of a partially hollow axle 679 with a rotating coupling for the glue supply hose 641 from the ink cartridge 627. This axle 679 connects to a glue wheel, which absorbs adhesive by capillary action through radial holes. A molded housing 682 surrounds the glue wheel, with an opening at the front. Pivoting side moldings and sprung outer doors are attached to the metal bracket and hinge out sideways when the rest of the assembly 673 is thrust forward. This action exposes the glue wheel through the front of the molded housing 682. Tension springs close the assembly and effectively cap the glue wheel during periods of inactivity.

As the sheet 604 passes into the glue wheel assembly 673, adhesive is applied to one vertical edge on the front side (apart from the first sheet of a document) as it is transported down into the binding assembly 605.

4 Product Tagging

Automatic identification refers to the use of technologies such as bar codes, magnetic stripe cards, smartcards, and RF transponders, to (semi-)automatically identify objects to data processing systems without manual keying.

For the purposes of automatic identification, a product item is commonly identified by a 12-digit Universal Product Code (UPC), encoded machine-readably in the form of a printed bar code. The most common UPC numbering system incorporates a 5-digit manufacturer number and a 5-digit item number. Because of its limited precision, a UPC is used to identify a class of product rather than an individual product item. The Uniform Code Council and EAN International define and administer the UPC and related codes as subsets of the 14-digit Global Trade Item Number (GTIN).

Within supply chain management, there is considerable interest in expanding or replacing the UPC scheme to allow individual product items to be uniquely identified and thereby tracked. Individual item tagging can reduce "shrinkage" due to lost, stolen or spoiled goods, improve the efficiency of demand-driven manufacturing and supply, facilitate the profiling of product usage, and improve the customer experience.

There are two main contenders for individual item tagging: optical tags in the form of so-called two-dimensional bar codes, and radio frequency identification (RFID) tags. For a detailed description of RFID tags, refer to Klaus Finkenzeller, *RFID Handbook*, John Wiley & Son (1999), the contents of which are herein incorporated by cross-reference. Optical tags have the advantage of being inexpensive, but require optical line-of-sight for reading. RFID tags have the advantage of supporting omnidirectional reading, but are comparatively expensive. The presence of metal or liquid can seriously interfere with RFID tag performance, undermining the omnidirectional reading advantage. Passive (reader-powered) RFID tags are projected to be priced at 10 cents each in multi-million quantities by the end of 2003, and at 5 cents each soon thereafter, but this still falls short of the sub-one-cent industry target for low-price items such as grocery. The read-only nature of most optical tags has also been cited as a disadvantage, since status changes cannot be written to a tag as an item progresses through the supply chain. However, this disadvantage is mitigated by the fact that a read-only tag can refer to information maintained dynamically on a network.

The Massachusetts Institute of Technology (MIT) Auto-ID Center has developed a standard for a 96-bit Electronic Product Code (EPC), coupled with an Internet-based Object Name Service (ONS) and a Product Markup Language (PML). Once an EPC is scanned or otherwise obtained, it is used to look up, possibly via the ONS, matching product information portably encoded in PML. The EPC consists of an 8-bit header, a 28-bit EPC manager, a 24-bit object class, and a 36-bit serial number. For a detailed description of the EPC, refer to Brock, D. L., *The Electronic Product Code (EPC)*, MIT Auto-ID Center (January 2001), the contents of which are herein incorporated by cross-reference. The Auto-ID Center has defined a mapping of the GTIN onto the EPC to demonstrate compatibility between the EPC and current practices Brock, D. L., *Integrating the Electronic Product Code (EPC) and the Global Trade Item Number (GTIN)*, MIT Auto-ID Center (November 2001), the contents of which are herein incorporated by cross-reference. The EPC is administered by EPCglobal, an EAN-UCC joint venture.

EPCs are technology-neutral and can be encoded and carried in many forms. The Auto-ID Center strongly advocates the use of low-cost passive RFID tags to carry EPCs, and has defined a 64-bit version of the EPC to allow the cost of RFID tags to be minimized in the short term. For detailed description of low-cost RFID tag characteristics, refer to Sarma, S., *Towards the 5¢ Tag*, MIT Auto-ID Center (November 2001), the contents of which are herein incorporated by cross-reference. For a description of a commercially-available low-cost passive RFID tag, refer to *915 MHz RFID Tag*, Alien Technology (2002), the contents of which are herein incorporated by cross-reference. For detailed description of the 64-bit EPC, refer to Brock, D. L., *The Compact Electronic Product Code*, MIT Auto-ID Center (November 2001), the contents of which are herein incorporated by cross-reference.

EPCs are intended not just for unique item-level tagging and tracking, but also for case-level and pallet-level tagging, and for tagging of other logistic units of shipping and transportation such as containers and trucks. The distributed PML database records dynamic relationships between items and higher-level containers in the packaging, shipping and transportation hierarchy.

4.1 Omnitagging in the Supply Chain

Using an invisible (e.g. infrared) tagging scheme to uniquely identify a product item has the significant advantage that it allows the entire surface of a product to be tagged, or a significant portion thereof, without impinging on the graphic design of the product's packaging or labelling. If the entire product surface is tagged, then the orientation of the product doesn't affect its ability to be scanned, i.e. a significant part of the line-of-sight disadvantage of a visible bar code is eliminated. Furthermore, since the tags are small and massively replicated, label damage no longer prevents scanning.

Omnitagging, then, consists of covering a large proportion of the surface of a product item with optically-readable invisible tags. Each omnitag uniquely identifies the product item on which it appears. The omnitag may directly encode the product code (e.g. EPC) of the item, or may encode a surrogate ID which in turn identifies the product code via a database lookup. Each omnitag also optionally identifies its own position on the surface of the product item, to provide the downstream consumer benefits of netpage interactivity described earlier.

Omnitags are applied during product manufacture and/or packaging using digital printers. These may be add-on infrared printers which print the omnitags after the text and graphics have been printed by other means, or integrated color and infrared printers which print the omnitags, text and graphics simultaneously. Digitally-printed text and graphics may include everything on the label or packaging, or may consist only of the variable portions, with other portions still printed by other means.

4.2 Omnitagging

Figure 13:
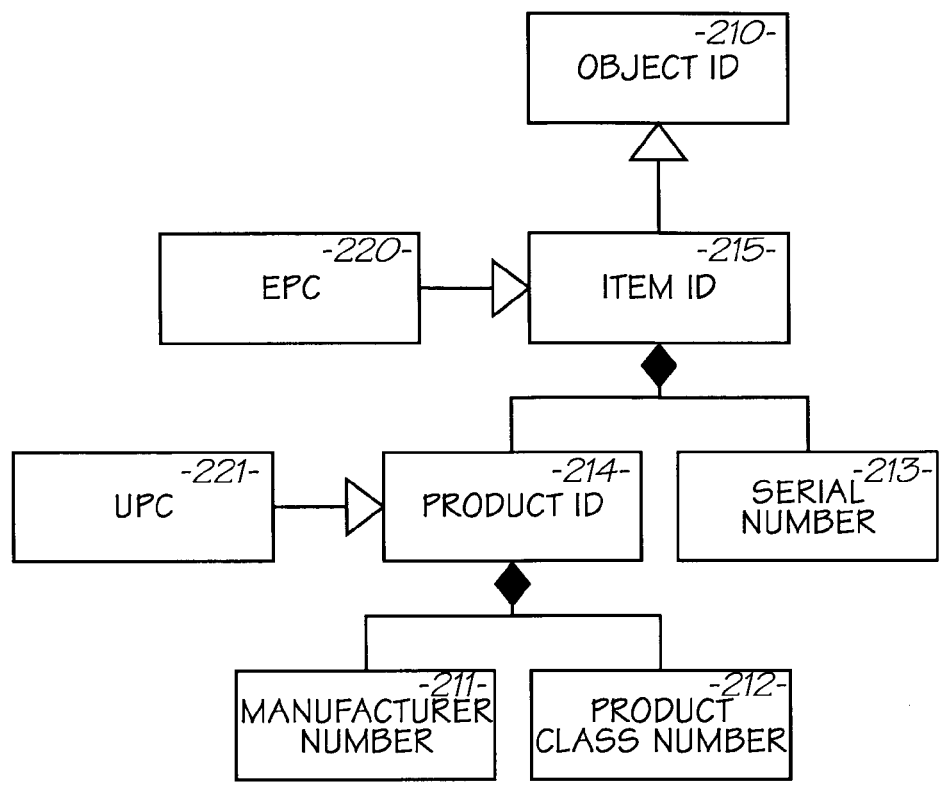
FIG. 13 is a schematic view of the structure of an item ID.

As shown in FIG. 13, a product's unique item ID 215 may be seen as a special kind of unique object ID 210. The Electronic Product Code (EPC) 220 is one emerging standard for an item ID. An item ID typically consists of a product ID 214 and a serial number 213. The product ID identifies a class of product, while the serial number identifies a particular instance of that class, i.e. an individual product item. The product ID in turn typically consists of a manufacturer number 211 and a product class number 212. The best-known product ID is the EAN.UCC Universal Product Code (UPC) 221 and its variants.

As shown in FIG. 14, an omnitag 202 encodes a page ID (or region ID) 50 and a two-dimensional (2D) position 86. The region ID identifies the surface region containing the tag, and the position identifies the tag's position within the two-dimensional region. Since the surface in question is the surface of a physical product item 201, it is useful to define a one-to-one mapping between the region ID and the unique object ID 210, and more specifically the item ID 215, of the product item. Note, however, that the mapping can be many-to-one without compromising the utility of the omnitag. For example, each panel of a product item's packaging could have a different region ID 50. Conversely, the omnitag may directly encode the item ID, in which case the region ID contains the item ID, suitably prefixed to decouple item ID allocation from general netpage region ID allocation. Note that the region ID uniquely distinguishes the corresponding surface region from all other surface regions identified within the global netpage system.

The item ID 215 is preferably the EPC 220 proposed by the Auto-ID Center, since this provides direct compatibility between omnitags and EPC-carrying RFID tags.

In FIG. 14 the position 86 is shown as optional. This is to indicate that much of the utility of the omnitag in the supply chain derives from the region ID 50, and the position may be omitted if not desired for a particular product.

For interoperability with the netpage system, an omnitag 202 is a netpage tag 4, i.e. it has the logical structure, physical layout and semantics of a netpage tag.

When a netpage sensing device such as the netpage pen 101 images and decodes an omnitag, it uses the position and orientation of the tag in its field of view and combines this with the position encoded in the tag to compute its own position relative to the tag. As the sensing device is moved relative to a Hyperlabelled surface region, it is thereby able to track its own motion relative to the region and generate a set of timestamped position samples representative of its time-varying path. When the sensing device is a pen, then the path consists of a sequence of strokes, with each stroke starting when the pen makes contact with the surface, and ending when the pen breaks contact with the surface.

When a stroke is forwarded to the page server 10 responsible for the region ID, the server retrieves a description of the region keyed by region ID, and interprets the stroke in relation to the description. For example, if the description includes a hyperlink and the stroke intersects the zone of the hyperlink, then the server may interpret the stroke as a designation of the hyperlink and activate the hyperlink.

4.3 Omnitag Printing

An omnitag printer is a digital printer which prints omnitags onto the label, packaging or actual surface of a product before, during or after product manufacture and/or assembly. It is a special case of a netpage printer 601. It is capable of printing a continuous pattern of omnitags onto a surface, typically using a near-infrared-absorptive ink. In high-speed environments, the printer includes hardware which accelerates tag rendering. This typically includes real-time Reed-Solomon encoding of variable tag data such as tag position, and real-time template-based rendering of the actual tag pattern at the dot resolution of the printhead.

The printer may be an add-on infrared printer which prints the omnitags after text and graphics have been printed by other means, or an integrated color and infrared printer which prints the omnitags, text and graphics simultaneously. Digitally-printed text and graphics may include everything on the label or packaging, or may consist only of the variable portions, with other portions still printed by other means. Thus an omnitag printer with an infrared and black printing capability can displace an existing digital printer used for variable data printing, such as a conventional thermal transfer or inkjet printer.

For the purposes of the following discussion, any reference to printing onto an item label is intended to include printing onto the item packaging in general, or directly onto the item surface. Furthermore, any reference to an item ID 215 is intended to include a region ID 50 (or collection of per-panel region ids), or a component thereof.

The printer is typically controlled by a host computer, which supplies the printer with fixed and/or variable text and graphics as well as item ids for inclusion in the omnitags. The host may provide real-time control over the printer, whereby it provides the printer with data in real time as printing proceeds. As an optimisation, the host may provide the printer with fixed data before printing begins, and only provide variable data in real time. The printer may also be capable of generating per-item variable data based on parameters provided by the host. For example, the host may provide the printer with a base item ID prior to printing, and the printer may simply increment the base item ID to generate successive item ids. Alternatively, memory in the ink cartridge or other storage medium inserted into the printer may provide a source of unique item ids, in which case the printer reports the assignment of items ids to the host computer for recording by the host.

Alternatively still, the printer may be capable of reading a pre-existing item ID from the label onto which the omnitags are being printed, assuming the unique ID has been applied in some form to the label during a previous manufacturing step. For example, the item ID may already be present in the form of a visible 2D bar code, or encoded in an RFID tag. In the former case the printer can include an optical bar code scanner. In the latter case it can include an RFID reader.

The printer may also be capable of rendering the item ID in other forms. For example, it may be capable of printing the item ID in the form of a 2D bar code, or of printing the product ID component of the item ID in the form of a 1D bar code, or of writing the item ID to a writable or write-once RFID tag.

4.4 Omnitag Scanning

Item information typically flows to the product server in response to situated scan events, e.g. when an item is scanned into inventory on delivery; when the item is placed on a retail shelf; and when the item is scanned at point of sale. Both fixed and hand-held scanners may be used to scan omnitagged product items, using both laser-based 2D scanning and 2D image-sensor-based scanning, using similar or the same techniques as employed in the netpage pen.

Figure 16:
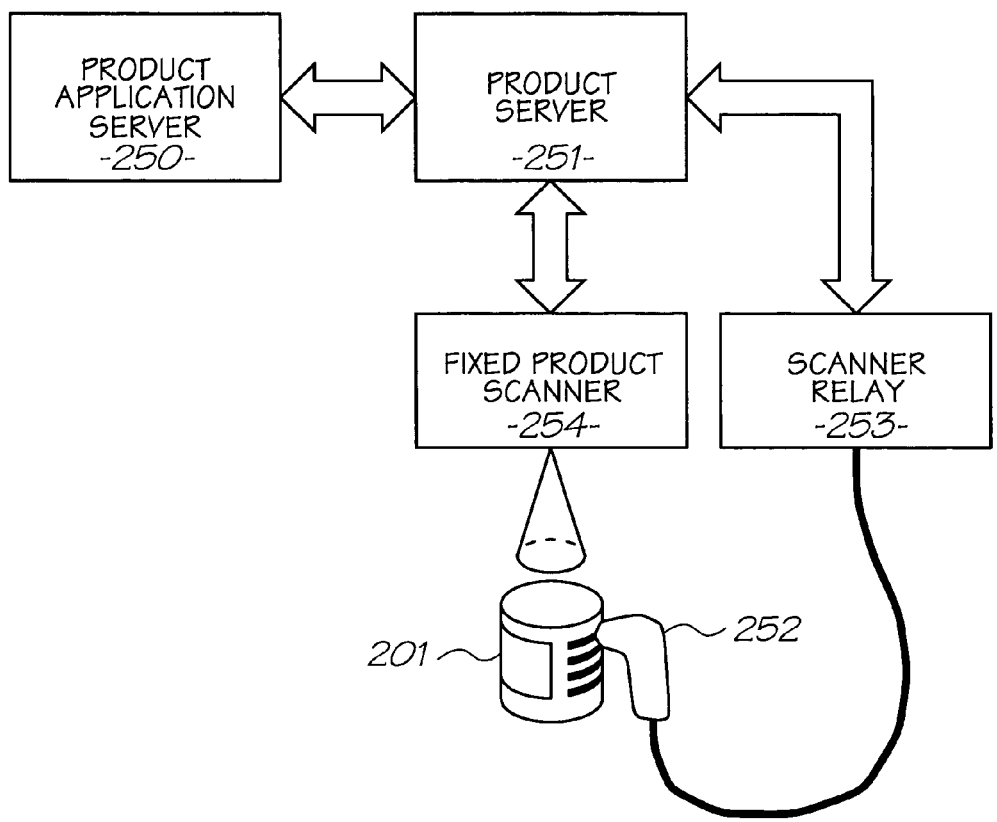
FIG. 16 is a schematic view of the interaction between a product item, a fixed product scanner, a hand-held product scanner, a scanner relay, a product server, and a product application server.

As shown in FIG. 16, both a fixed scanner 254 and a hand-held scanner 252 communicate scan data to the product server 251. The product server may in turn communicate product item event data to a peer product server (not shown), or to a product application server 250, which may implement sharing of data with related product servers. For example, stock movements within a retail store may be recorded locally on the retail store's product server, but the manufacturer's product server may be notified once a product item is sold.

4.5 Omnitag-Based Netpage Interactions

A product item whose labelling, packaging or actual surface has been omnitagged provides the same level of interactivity as any other netpage.

There is a strong case to be made for netpage-compatible product tagging. Netpage turns any printed surface into a finely differentiated graphical user interface akin to a Web page, and there are many applications which map nicely onto the surface of a product. These applications include obtaining product information of various kinds (nutritional information; cooking instructions; recipes; related products; use-by dates; servicing instructions; recall notices); playing games; entering competitions; managing ownership (registration; query, such as in the case of stolen goods; transfer); providing product feedback; messaging; and indirect device control. If, on the other hand, the product tagging is undifferentiated, such as in the case of an undifferentiated 2D barcode or RFID-carried item ID, then the burden of information navigation is transferred to the information delivery device, which may significantly increase the complexity of the user experience or the required sophistication of the delivery device user interface.

The invention will now be described with reference to the following examples. However, it will of course be appreciated that this invention may be embodied in many other forms without departing from the scope of the invention, as defined in the accompanying claims.

EXAMPLES

Preparation 1

6,7-(4'-Methoxyphenoxy)naphthalene-2,3-dicarbonitrile (4)

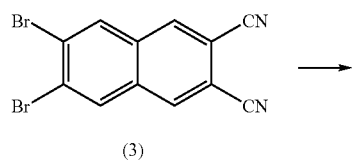

(3)

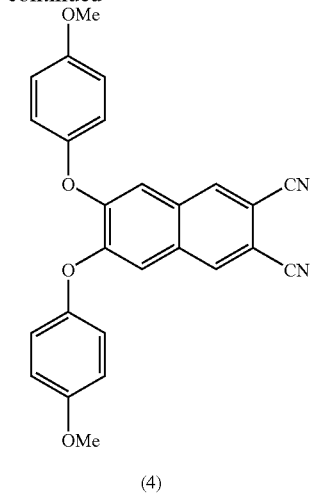

(4)

A mixture of 6,7-dibromonaphthalene-2,3-dicarbonitrile 3 (508 mg, 0.151 mmol), 4-methoxyphenol (1.12 g, 9.00 mmol) and freshly dried potassium carbonate (2.70 g, 19 mmol) in dimethylformamide (10 mL) was stirred at 130° C. overnight. The reaction mixture was cooled to 80° C. and water (60 mL) was slowly added to form a precipitate that was filtered off, washed with water and methanol/water (50:50) to give 4 as a chocolate-brown powder (480 mg, 75%).

$^1$H NMR (300 MHz, CDCl$_3$): δ3.89 (6H, s); 7.02 (4H, d, J=7.8 Hz); 7.14 (4H, d, J=7.8 Hz); 7.15 (2H, s); 8.02 (2H, s).

Example 1

Copper(II) tetrakis[6,7-(4'-methoxyphenoxy)]naphthalocyanine (5)

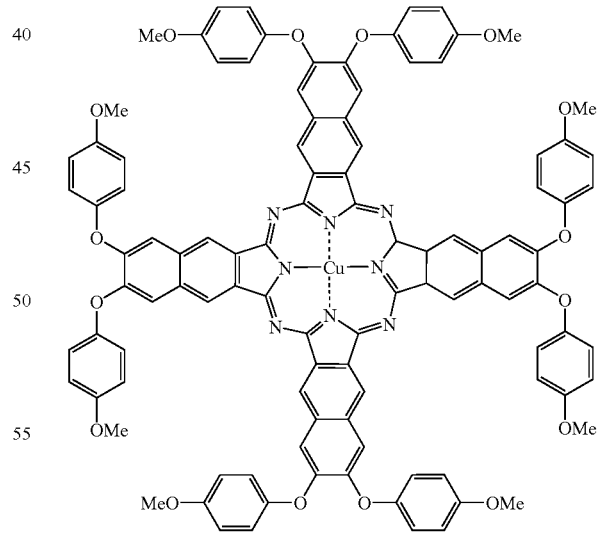

A mixture of the dinitrile 4 (240 mg, 0.568 mmol), copper (I) chloride and DBU (135 μL, 135 mg, 0.888 mmol) in 1-pentanol (2 mL) was heated at reflux overnight. The reaction mixture was cooled to room temperature and diluted with methanol (20 mL) and the resulting solid was filtered off and washed with methanol, water and acetone to give 5 as a reddish-brown powder (201 mg, 81%).

UV-Vis-NIR (DMSO): 773 nm.

Example 2

Sulfonation of Copper(II) tetrakis[6,7-(4'-methoxyphenoxy)]naphthalocyanine

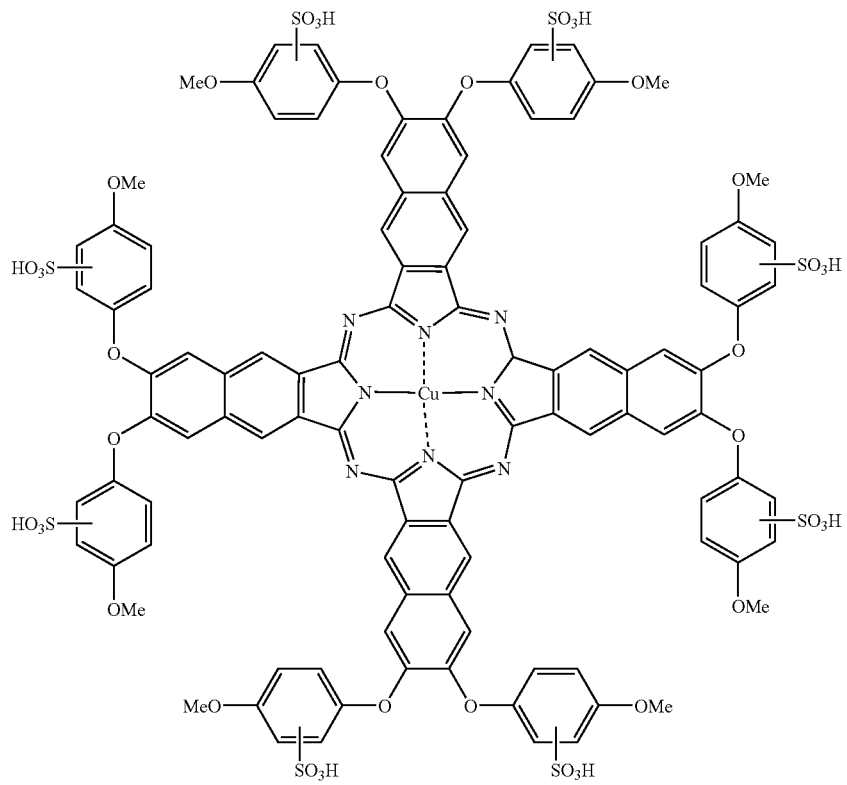

(6)

A solution of the copper(II) naphthalocyanine 5 (110 mg, 62.7 μmol) in sulfuric acid (98%, 1 mL) was stirred at 45° C. for 45 min. The reaction mixture was added dropwise to ether/chloroform (9:1, 150 mL) to precipitate the product. The supernatant was decanted off and the solid was resuspended in ether/chloroform (9:1, 100 mL). Filtration, followed by washing with chloroform, ether and acetone gave the sulfonic acid 6 (144 mg, 96%) as a red-brown powder.

UV-Vis-NIR (DMSO): 775 nm, 690 nm.

Example 3

Vanadyl tetrakis[6,7-(4'-methoxyphenoxy)]naphthalocyanine (7)

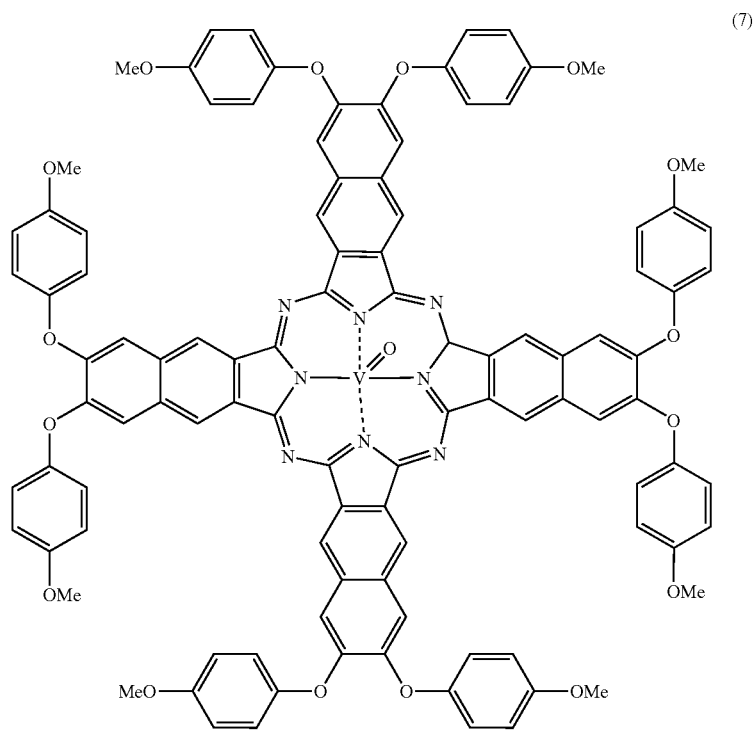

A mixture of the dinitrile 4 (213 mg, 0.503 mmol), vanadyl acetylacetonate (45 mg, 0.169 mmol) and DBU (130 μL, 130 mg, 0.854 mmol) in 1-pentanol (2 mL) was heated at reflux overnight. The reaction mixture was cooled to room temperature and diluted with methanol (20 mL). The resulting solid was filtered off and washed with methanol, water and acetone to give 7 as a dark reddish-brown powder (185 mg, 84%).

UV-Vis-NIR (DMSO, 10.8 μM): 808 nm ($\epsilon$=84,000); 718 ($\epsilon$=19,500).

Example 4

Sulfonation of vanadyl tetrakis[6,7-(4'-methoxyphenoxy)]naphthalocyanine

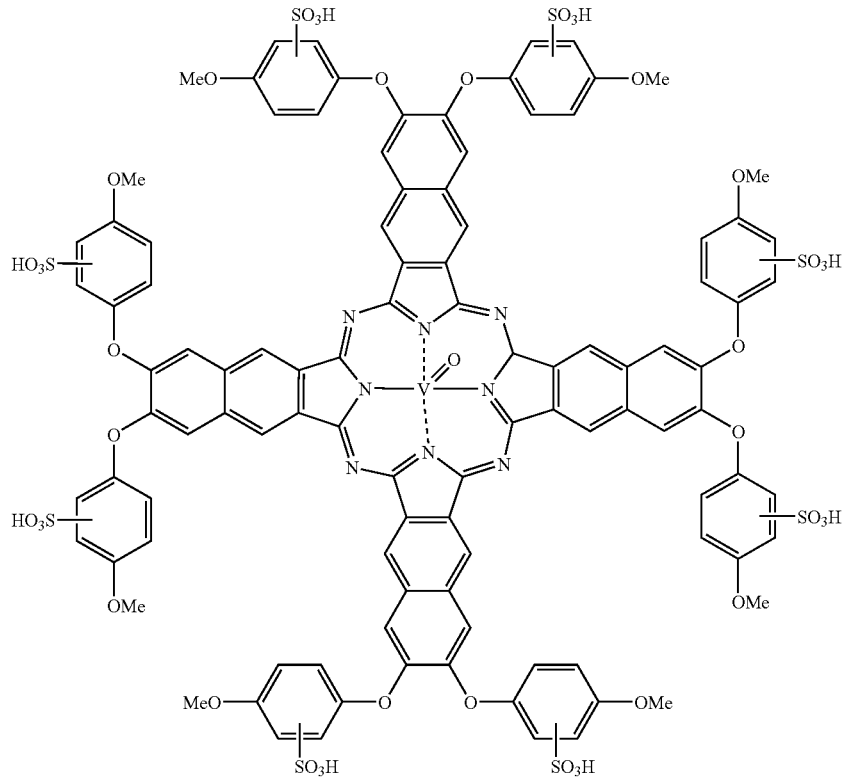

(8)

A solution of the vanadyl naphthalocyanine 7 (237 mg, 0.135 mmol) in sulfuric acid (98%, 2 mL) was stirred at 50° C. for 45 min. The reaction mixture was added dropwise to ether/chloroform (9:1, 150 mL) to precipitate the product. The supernatant liquid was decanted off and the solid was resuspended in ether/chloroform (9:1, 150 mL). Filtration, followed by washing with chloroform, ether and acetone gave 8 (247 mg, 81%) as a black-green powder.

UV-Vis-NIR (DMSO): 808 nm, 720 nm.

The invention claimed is:
1. A naphthalocyanine dye of formula (I):

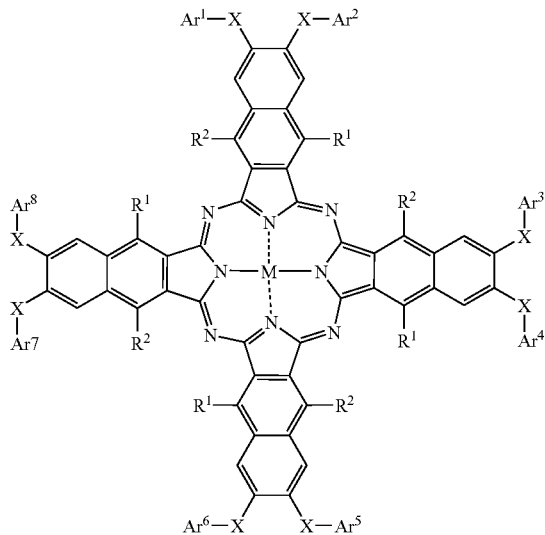

wherein
M is a metal group or is absent;
$R^1$ and $R^2$ are independently selected from the group consisting of: hydrogen and $C_{1-12}$ alkoxy;
X is selected from the group consisting of: O, S and —NH—;
$Ar^1, Ar^2, Ar^3, Ar^4, Ar^5, Ar^6, Ar^7$ and $Ar^8$ are selected from the group consisting of: phenyl, naphthyl, pyridyl, furanyl, pyrollyl and thiophenyl, each of $Ar^1, Ar^2, Ar^3, Ar^4, Ar^5, Ar^6, Ar^7$ and $Ar^8$ being optionally substituted with 1, 2, 3, 4 or 5 groups, each group being independently selected from the group consisting of: $C_{1-12}$ alkyl, $C_{1-12}$ alkoxy, $C_{1-12}$ arylalkyl, $C_{1-12}$ arylalkoxy, —(OCH$_2$CH$_2$)$_d$OR$^d$, cyano, halogen, amino, hydroxyl, thiol, —SR$^v$, —NR$^u$R$^v$, nitro, phenyl, phenoxy, —CO$_2$R$^v$, —C(O)R$^v$, —OCOR$^v$, —SO$_2$R$^v$, —OSO$_2$R$^v$, —NHC(O)R$^v$, —CONR$^u$R$^v$, —CONR$^u$R$^v$, sulfonic acid, sulfonic acid salt and sulfonamide;
d is an integer from 2 to 5000;
$R^d$ is H, $C_{1-8}$ alkyl or $C(O)C_{1-8}$ alkyl; and
$R^u$ and $R^v$ are independently selected from the group consisting of: hydrogen, $C_{1-12}$ alkyl, phenyl or phenyl-$C_{1-8}$ alkyl;
and wherein at least one of $Ar^1, Ar^2, Ar^3, Ar^4, Ar^5, Ar^6, Ar^7$ and $Ar^8$ is substituted with a sulfonic acid or a sulfonic acid salt.

2. The dye of claim 1, wherein at least one of $Ar^1, Ar^2, Ar^3, Ar^4, Ar^5, Ar^6, Ar^7$ and $Ar^8$ is substituted with —SO$_3$Z; wherein:
Z is H, Li, Na, K or N$^+$ (R$^m$)(R$^n$)(R$^s$)(R$^t$); and
R$^m$, R$^n$, R$^s$, R$^t$ may be the same or different and are independently selected from the group consisting of: H, $C_{1-8}$ alkyl, $C_{6-12}$ arylalkyl and $C_{6-12}$ aryl.

3. The dye of claim 1, wherein each of $Ar^1, Ar^2, Ar^3, Ar^4, Ar^5, Ar^6, Ar^7$ and $Ar^8$ is substituted with a sulfonic acid or a sulfonic acid salt.

4. The dye of claim 3, which is of formula (III):

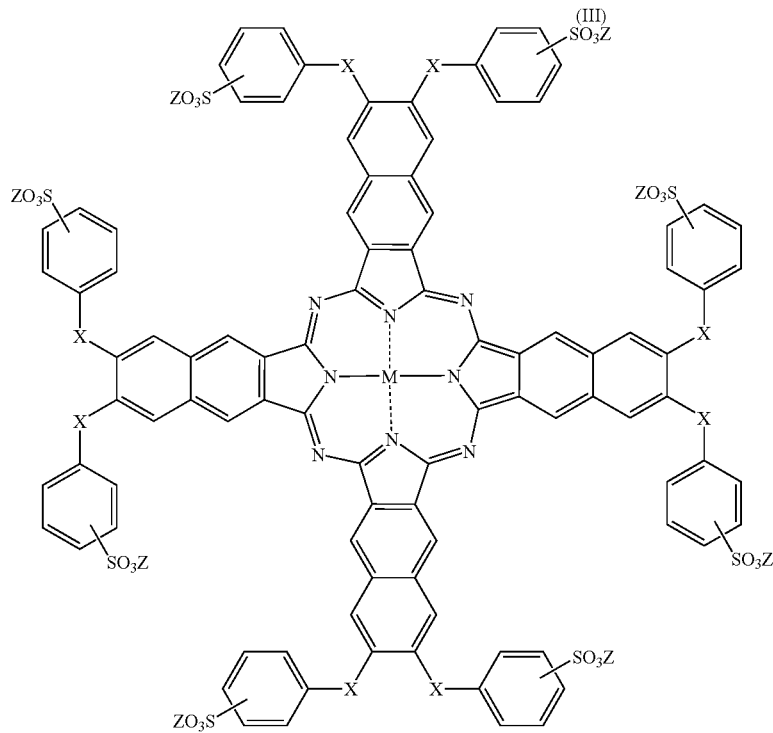

wherein:
Z is H, Li, Na, K or N$^+$ (R$^m$)(R$^n$)(R$^s$)(R$^t$); and
R$^m$, R$^n$, R$^s$, R$^t$ may be the same or different and are independently selected from the group consisting of: H, $C_{1-8}$ alkyl, $C_{6-12}$ arylalkyl and $C_{6-12}$ aryl.

5. The dye of claim 4, wherein each —SO$_3$Z group is at a para position.

6. The dye of claim 1, which is of formula (IV[d2]):

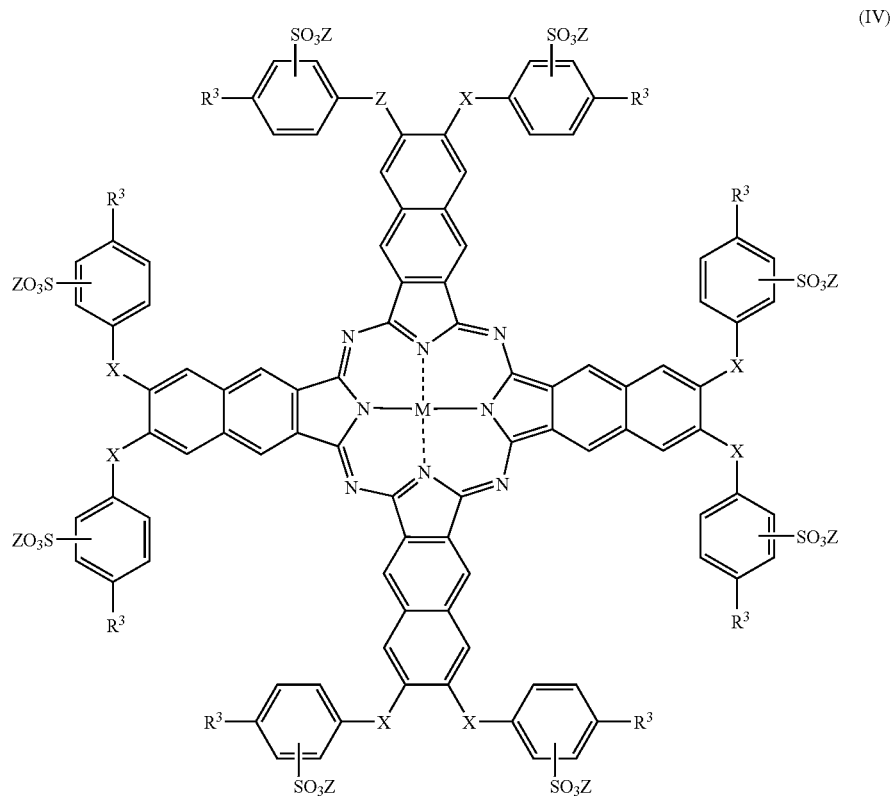

wherein:
Z is H, Li, Na, K or $N^+(R^m)(R^n)(R^s)(R^t)$;
$R^m$, $R^n$, $R^s$, $R^t$ may be the same or different and are independently selected from the group consisting of: H, $C_{1-8}$ alkyl, $C_{6-12}$ arylalkyl and $C_{6-12}$ aryl; and
$R^3$ is selected from the group consisting of: $C_{1-12}$ alkyl, $C_{1-12}$ alkoxy, $C_{1-12}$ arylalkyl, $C_{1-12}$ arylalkoxy, $-(OCH_2CH_2)_dOR^d$, cyano, halogen, amino, hydroxyl, thiol, $-SR^v$, $-NR^uR^v$, nitro, phenyl, phenoxy, $-CO_2R^v$, $-C(O)R^v$, $-OCOR^v$, $-NHC(O)R^v$, $-CONR^uR^v$ and $-CONR^uR^v$.

7. The dye of claim 6, wherein $R^3$ is $C_{1-6}$ alkyl or $C_{1-6}$ alkoxy.

8. The dye of claim 1, wherein M is $SnCl_2$, Cu, V=O, or Ga(OH).

9. An inkjet ink comprising a dye according to claim 1.

* * * * *